(12) United States Patent
Kaufman et al.

(10) Patent No.: US 7,194,117 B2
(45) Date of Patent: Mar. 20, 2007

(54) SYSTEM AND METHOD FOR PERFORMING A THREE-DIMENSIONAL VIRTUAL EXAMINATION OF OBJECTS, SUCH AS INTERNAL ORGANS

(75) Inventors: Arie E. Kaufman, Plainview, NY (US); Zhengrong Liang, Stony Brook, NY (US); Mark R. Wax, Greenlawn, NY (US); Ming Wan, Stony Brook, NY (US); Dongqing Chen, Lake Ronkonkoma, NY (US); Bin Li, Lake Grove, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 0 days.

(21) Appl. No.: 09/777,120

(22) Filed: Feb. 5, 2001

(65) Prior Publication Data
US 2001/0031920 A1    Oct. 18, 2001

Related U.S. Application Data

(63) Continuation-in-part of application No. 09/493,559, filed on Jan. 28, 2000, now Pat. No. 6,343,936, and a continuation-in-part of application No. 09/343,012, filed on Jun. 29, 1999, now Pat. No. 6,331,116.

(51) Int. Cl.
*G06K 9/00*        (2006.01)

(52) U.S. Cl. .................... 382/128; 382/285; 378/41

(58) Field of Classification Search ............... 382/100, 382/128, 129, 130, 131–134, 181, 194, 199, 382/203, 216, 221, 285, 286, 291, 316, 274, 382/154, 168; 250/455, 458.1, 453.11; 345/418, 345/419, 424, 444, 442, 420, 426, 581, 589, 345/773, 421; 378/28, 41, 46, 90; 600/411, 600/425; 377/10, 11; 356/38, 39
See application file for complete search history.

(56) References Cited

U.S. PATENT DOCUMENTS

| 4,367,216 A | 1/1983 | Mutzel et al. |
| 4,391,280 A | 7/1983 | Miller |

(Continued)

FOREIGN PATENT DOCUMENTS

| WO | 9613207 | 5/1996 |

(Continued)

OTHER PUBLICATIONS

Hong et al., "3D Virtual Colonoscopy," 1995 Biomedical Visualization Proceedings, pp. 26-32 and 83 (1995).

(Continued)

*Primary Examiner*—Jingge Wu
*Assistant Examiner*—Seyed Azarian
(74) *Attorney, Agent, or Firm*—Dorsey & Whitney LLP

(57) ABSTRACT

Methods for generating a three-dimensional visualization image of an object, such as an internal organ, using volume visualization techniques are provided. The techniques include a multi-scan imaging method; a multi-resolution imaging method; and a method for generating a skeleton of a complex three dimension object. The applications include virtual cystoscopy, virtual laryngoscopy, virtual angiography, among others.

20 Claims, 27 Drawing Sheets

U.S. PATENT DOCUMENTS

| | | | |
|---|---|---|---|
| 4,630,203 A | 12/1986 | Szirtes | |
| 4,710,876 A | 12/1987 | Cline et al. | |
| 4,719,585 A | 1/1988 | Cline et al. | |
| 4,729,098 A | 3/1988 | Cline et al. | |
| 4,737,921 A | 4/1988 | Goldwasser et al. | |
| 4,751,643 A | 6/1988 | Lorensen et al. | |
| 4,791,567 A | 12/1988 | Cline et al. | |
| 4,823,129 A | 4/1989 | Nelson | |
| 4,831,528 A | 5/1989 | Crawford et al. | |
| 4,874,362 A | 10/1989 | Wiest et al. | |
| 4,879,668 A | 11/1989 | Cline et al. | |
| 4,984,157 A | 1/1991 | Cline et al. | |
| 4,985,834 A | 1/1991 | Cline et al. | |
| 4,985,856 A | 1/1991 | Kaufman | |
| 4,987,554 A | 1/1991 | Kaufman | |
| 4,991,092 A * | 2/1991 | Greensite | 382/131 |
| 4,993,415 A | 2/1991 | Long | |
| 5,006,109 A | 4/1991 | Douglas et al. | |
| 5,023,072 A | 6/1991 | Cheng | |
| 5,038,302 A | 8/1991 | Kaufman | |
| 5,047,772 A | 9/1991 | Ribner | |
| 5,056,020 A | 10/1991 | Feldman et al. | |
| 5,095,521 A * | 3/1992 | Trousset et al. | 345/421 |
| 5,101,475 A * | 3/1992 | Kaufman et al. | 345/424 |
| 5,127,037 A | 6/1992 | Bynum | |
| 5,166,876 A | 11/1992 | Cline et al. | |
| 5,170,347 A | 12/1992 | Tuy et al. | |
| 5,187,658 A | 2/1993 | Cline et al. | |
| 5,204,625 A | 4/1993 | Cline et al. | |
| 5,229,935 A | 7/1993 | Yamagishi et al. | |
| 5,245,538 A | 9/1993 | Lis | |
| 5,261,404 A | 11/1993 | Mick et al. | |
| 5,265,012 A | 11/1993 | Amans et al. | |
| 5,270,926 A | 12/1993 | Tam | |
| 5,283,837 A | 2/1994 | Wood | |
| 5,295,488 A | 3/1994 | Lloyd et al. | |
| 5,299,288 A | 3/1994 | Glassman et al. | |
| 5,319,549 A * | 6/1994 | Katsuragawa et al. | 382/108 |
| 5,322,070 A | 6/1994 | Goodman et al. | |
| 5,345,490 A | 9/1994 | Finnigan et al. | |
| 5,361,763 A * | 11/1994 | Kao et al. | 600/410 |
| 5,365,927 A | 11/1994 | Roemer et al. | |
| 5,371,778 A | 12/1994 | Yanof et al. | |
| 5,442,733 A | 8/1995 | Kaufman et al. | |
| 5,458,111 A * | 10/1995 | Coin | 600/560 |
| 5,611,025 A | 3/1997 | Lorensen et al. | |
| 5,623,586 A | 4/1997 | Höhne | |
| 5,630,034 A | 5/1997 | Oikawa et al. | |
| 5,699,799 A | 12/1997 | Xu et al. | |
| 5,734,384 A | 3/1998 | Yanof et al. | |
| 5,782,762 A | 7/1998 | Vining | |
| 5,920,319 A * | 7/1999 | Vining et al. | 345/420 |
| 5,971,767 A | 10/1999 | Kaufman | |
| 5,986,662 A | 11/1999 | Argiro et al. | |
| 6,125,194 A * | 9/2000 | Yeh et al. | 382/132 |
| 6,130,671 A | 10/2000 | Argiro | |
| 6,219,059 B1 | 4/2001 | Argiro | |
| 6,272,366 B1 | 8/2001 | Vining | |

FOREIGN PATENT DOCUMENTS

| | | |
|---|---|---|
| WO | 9811524 | 3/1998 |
| WO | 9837517 | 8/1998 |
| WO | 0055812 | 9/2000 |
| WO | 0055814 | 9/2000 |

OTHER PUBLICATIONS

Hong et al., "3D Reconstruction and Visualization of the Inner Surface of the Colon from Spiral CT Data," IEEE, pp. 1506-1510 (1997).

William E. Lorensen, "The Exploration of Cross-Sectional Data with a Virtual Endoscope," Interactive Technology and the New Health Paradigm, IOS Press, pp. 221-230 (1995).

Adam L. Penenberg, "From Stony Brook, a New Way to Examine Colons, Externally," The New York Times, p. 6 (1996).

David J. Vining, "Virtual Colonoscopy," Advance for Administrators in Radiology, pp. 50-52 (1998).

Zhou et al., "Three-Dimensional Skeleton and Centerline Generation Based on an Approximate Minimum Distance Field," The Visual Computer, 14:303-314 (1998).

Liang Z et al., "Inclusion of a priori information in segmentation of colon lumen for 3D virtual colonscopy", 1997 IEEE Nuclear Science Symposium Conference Record, pp. 1423-1427, vol. 2.

Valev et al., "Techniques of CT colongraphy (virtual colonscopy)", Critical Reviews in Biomedical Engineering, 1999, Begall House, vol. 27, No. 1-2, pp. 1-25.

Shibolet O et al., "Coloring voxel-based objects for virtual endoscopy", IEEE Symposium on Volume Visualization, Research Triangle, Oct. 1998.

Kaufman A., Wan M., "Disobstruction of Colon Wall Collapse", Project Description, online www.cs.sunysb.edu, Jan. 1999.

Holzapfel G A, et al., "Large strain analysis of soft biological membranes: formulation and finite element analysis", Computer Methods in Applied Mechanics and Engineering, vol. 132, No. 1-2, pp. 45-61, 1996.

Kaye J. et al., "A 3D virtual environment for modeling mechanical cardiopulmonary interactings", CVRMED-MRCA '97, pp. 389-398, 1997.

Burgard W. et al., "Active mobile robot localization by entropy minimization", Proceedings second euromicro workshop on advanced mobile robots, pp. 155-162, 1997.

Suya You et al., "Interactive volume rendering for virtual colonoscopy", Proceedings Visualization '97, pp. 433-436, 571.

Pai D.K. et al., "Multiresolution Rough Terrain Motion Planning", IEEE Transactions on Robotics and Automatic, vol. 14, No. 1, pp. 19-33, 1998.

Hagen H. et al., "Methods for Surface Interrogation", Proceedings of the Conference on Visualization, vol. CONF 1, pp. 187-193, 1990.

Chen et al., "A tree-branch searching, multiresolution approach to skeletonization for virtual endoscopy".

Liang Z. et al., "Feasibility Studies on Extracting Bladder Wall from MR Images for Virtual Cytoscopy".

Chen et al., "Virtual Laryngoscopy: Feasibility Studies by CT and MRI", IEEE Medical Imaging Conference, Nov. 1999.

Chen et al., "A multi-scan MRI-based virtual cytoscopy".

Chen et al., "MRI-Based Virtual Cytoscopy: The image segmentation and visualization", SPIE Conference, Feb. 12-18, 2000.

Chen et al., "A Fast Algorithm to Generate Centerline for Virtual Colonoscopy", SPIE Conference, Feb. 12-18, 2000.

Richard Robb, "Virtual (Computed) Endoscopy: Development and Evaluation Using the Visible Human Datasets", Oct. 7-8, 1996. www.mayo.edu.

I. Bitter et al., "Penalized-Distance Volumetric Skeleton Algorithm", IEEE Transactions on Visualization and Computer Graphics, vol. 7, No. 3, Jul.-Sep. 2001, pp. 195-206.

M. Wan et al., "Distance-Field Based Skeletons for Virtual Navigation", *Visualization 2000*, San Diego, CA, Oct. 2001.

M. Sato et al., "An automatic colon segmentation for 3D virtual colonoscopy", IEICE Trans. Information and Systems, vol. E84-D, No. 1, Jan. 2001, pp. 201-208.

D. Chen et al., "A Novel Approach to Extract Colon Lumen from CT Images for Virtual Colonoscopy" IEEE Transactions on Medical Imaging, vol. 19, No. 12, Dec. 2000, pp. 1220-1226.

M. Wax et al., "Virtual Colonoscopy—CT Contrast Agent", Second International Symposium on Virtual Colonoscopy, Boston, MA, Oct. 2000.

K. Kreeger, et al., "Volume Rendering for Virtual Colonoscopy on an Affordable PC", Second International Symposium on Virtual Colonoscopy, Boston, MA, Oct. 2000.

S. Lakare et al., "3D Digital Cleansing Using Segmentation Rays", IEEE Visualization 2000 Conference Proceedings, ACM/SIGGRAPH Press, pp. 37-44, Oct. 2000.

S. Lakare et al., "Automated Pre-navigation Processing for Virtual Colonoscopy", Second International Symposium on Vitual Colonoscopy, pp., Oct. 2000.

K. Kreeger et al., "Perspective Virtual Endoscopy with VolumePro Parallel Rendering", Center for Visual Computing and Department of Computer Science, pp. 1-8.

D. Chen et al. "A tree-branch searching, multi-resolution approach to skeletonization for virtual endoscopy", SPIE Medical Imaging 2000, Feb. 2000.

M. Wan et al., "3D Virtual Colonoscopy with Real-time Volume Rendering", SPIE Medical Imaging 2000, Feb. 2000.

M. Wax et al., "Advancing Virtual Colonoscopy to Practice", International Workshop on 3D Imaging and Virtual Endoscopy, Feb. 2000.

W. Li et al., "Virtual Colonoscopy Powered by VolumePro", pp. 1-13, month unavailable 1999.

M. Wan et al., "Volume Rendering Based Interactive Navigation within the Human Colon", IEEE Visualization '99 conference, San Francisco, CA, Oct. 1999, pp. 397-400.

R. Chiou et al., "Interactive Fly-Path Planning Using Potential Fields and Cell Decomposition for Virtual Endoscopy", IEEE Trans. Nuclear Sciences, vol. 46, No. 4, Aug. 1999, pp. 1045-1049.

D. Chen et al., "MR Imaging and Segmentation of the Colon Wall for Virtual Colonoscopy", Soc. Magn. Reson. Medicine, vol. 3, pp. 2203.

R. Chiou et al., "Volume Segmentation and Rendering of Mixtures of Materials for Virtual Colonoscopy", SPIE Medical Imaging '99, Feb. 1999, pp. 133-138.

Z. Liang et al., "On Segmentation of Colon Lumen for Virtual Colonoscopy", SPIE Medical Imaging, Feb. 1999, pp. 270-278.

Z. Liang et al., "Virtual Endoscopy in Early Detection of Cancers", Biomedical Imaging Symposium: Visualizing the Future of Biology amd Medicine, Washington, D.C., Feb. 1999.

R. Chiou et al., "Unified Analysis, Modeling, Matching and Synthesis for CT Color Texture Mapping from the Visible Human Dataset", The Second Visible Human Project Conf., Bethesda, MD, Oct. 1998.

M. Wan et al., "Boundary Cell-Based Acceleration for Volume Ray Casting", Computer & Gaphices, vol. 22, No. 6, 1998, pp. 715-721.

R. Chiou et al., "Interactive Path Planning for Virtual Endoscopy", Conf. Record IEEE NSS-MIC, Nov. 1998.

M. Wax et al., "Electronic Colon Cleansing for Virtual Colonoscopy", Presentation at the first Int'l . Conf. on Virtual Colonoscopy, Boston, MA, Oct. 1998.

L. Hong et al., "Virtual Voyage: Interactive Navigation in the Human Colon", Proc. ACM SIGGRAPH '97, Aug. 1997, pp. 27-34.

A. Viswambharan et al., "Virtual Colonoscopy: Three-dimensional Reconstruction of the Mucosal Surface of the Colon", Conf. of Radiological Society of North America (RSNA), Dec. 1996, pp. 565 (Scientific Merit Award).

L. Hong et al., "Physically-Based Interactive Navigation", Technical report TR.96.01.09, Computer Science Department, SUNY at Stony Brook, Jan. 1996.

L. Hong et al., "Visible Human Virtual Colonoscopy", Conference of National Library of Medicine Visible Human Project, Oct. 1996, pp. 29-30.

80th Scientific Assembly and Annual Meeting Nov. 27-Dec. 2, 1994, Radiology Society of North America Founded in, InfoRAD Exhibits.

* cited by examiner

RENDERED NODES {I}
SKIPPED NODE { }

RENDERED NODES: {I, F}
SKIPPED NODES: { }

RENDERED NODES: {I, F}
SKIPPED NODES: {A, B}

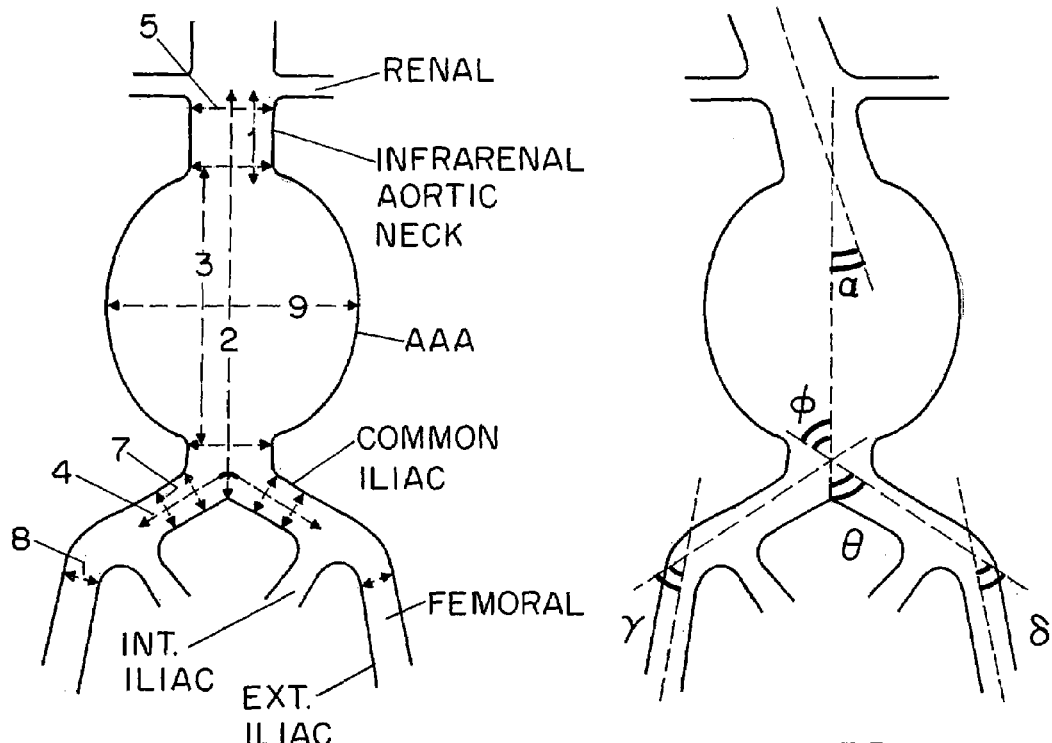
FIG. 33A
FIG. 33B
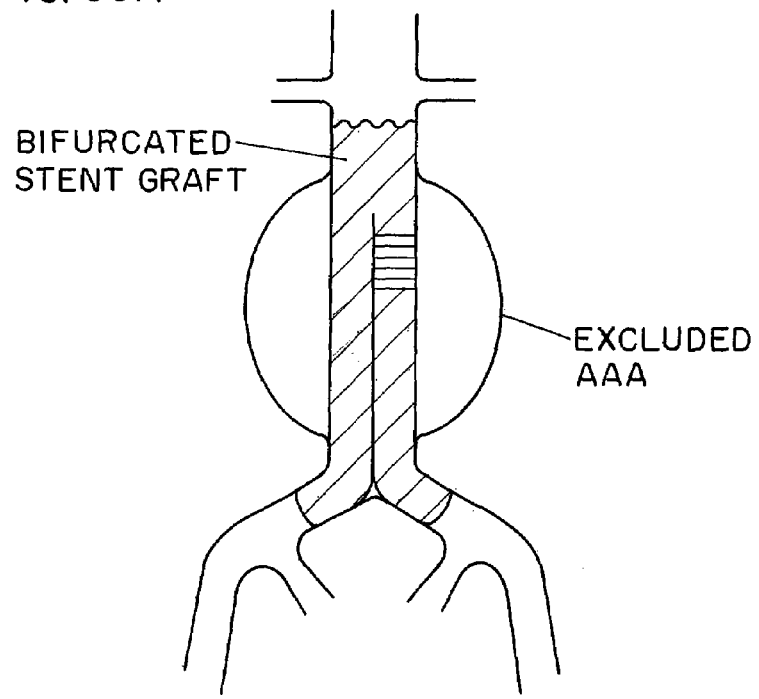
FIG. 33C

1) Label root voxel with integer 0;
2) Construct a queue and line up the root in the queue;
3) If (There is at least one voxel in the queue)
    Serve the voxel x on the top of the queue:
    For (each of x's 26-connected neighbor voxel y) {
       If (y in the volume and has not been labeled yet) {
          Line up the y in the queue;

/* label the voxel y */
          Set dist = 999999;
          For (each of y's 26-connected neighbor voxel z) {
             If (z in the volume and has been already labeled with an integer of $n_z$) {

$d_z \equiv n_z + d(y, z)$;
                where $d(y,z)$ is 10, 14 or 17 if the Euclidean distance between y and z is 1, $\sqrt{2}$, or $\sqrt{3}$, respectively;
             }
             If ($dist > d_z$) {
                label y with integer dist;
                dist = $d_z$;
             }
          }
       }
    }
    x leaves the quere;
}
Else {
    end of calculating the distance map.
}

FIG. 36 ized its volume in three-dimensional space would be ben-

SYSTEM AND METHOD FOR PERFORMING A THREE-DIMENSIONAL VIRTUAL EXAMINATION OF OBJECTS, SUCH AS INTERNAL ORGANS

This application is a continuation-in-part of U.S. patent application, Ser. No. 09/493,559, filed on Jan. 28, 2000, now U.S. Pat. No. 6,343,936 entitled "System And Method For Performing a Three-dimensional Virtual Examination, Navigation and Visualization" and is a continuation-in-part of U.S. patent application, Ser. No. 09/343,012, filed on Jun. 29, 1999, now U.S. Pat. No. 6,331,116 entitled "System And Method For Performing a Three-dimensional Virtual Segmentation And Examination," both of which are a continuation in part of U.S. application Ser. No. 08/714,697, filed Sept. 16, 1996, now U.S. Pat. No. 5,971,767, entitled "System and Method for Performing a Three Dimensional Virtual Examination."

STATEMENT REGARDING FEDERALLY SPONSORED RESEARCH

The invention described herein was funded in part by grants from the National Institutes of Health (NIH), namely, NIH grants HL 54166, NS 53833, NS 33859, and CA 79180. The United States government may have certain rights under the invention.

TECHNICAL FIELD

The present invention relates to a system and method for performing a volume based three-dimensional virtual examination, and more particularly relates to a system which offers enhanced visualization and navigation properties.

BACKGROUND OF THE INVENTION

Colon cancer continues to be a major cause of death throughout the world. Early detection of cancerous growths, which in the human colon initially manifest themselves as polyps, can greatly improve a patient's chance of recovery. Presently, there are two conventional ways of detecting polyps or other masses in the colon of a patient. The first method is a colonoscopy procedure, which uses a flexible fiber-optic tube called a colonoscope to visually examine the colon by way of physical rectal entry with the scope. The doctor can manipulate the tube to search for any abnormal growths in the colon. The colonoscopy, although reliable, is both relatively costly in money and time, and is an invasive, uncomfortable painful procedure for the patient.

The second detection technique is the use of a barium enema and two-dimensional X-ray imaging of the colon. The barium enema is used to coat the colon with barium, and a two-dimensional X-ray image is taken to capture an image of the colon. However, barium enemas may not always provide a view of the entire colon, require extensive pre-treatment and patient manipulation, is often operator-dependent when performing the operation, exposes the patient to excessive radiation and can be less sensitive than a colonoscopy. Due to deficiencies in the conventional practices described above, a more reliable, less intrusive and less expensive way to examine the colon for polyps is desirable. A method to examine other human organs, such as the lungs, for masses in a reliable, cost effective way and with less patient discomfort is also desirable.

Another leading cause of cancer deaths in the United States is bladder cancer. In 1995, there were 50,000 new cases of bladder cancer reported and 11,000 deaths were reported as a result of this disease. The most common test for bladder cancer is the use of a urine "dipstick" or conventional urinalysis. However, such tests are generally only effective at detecting bladder cancer in its later developed stages and does not provide any information regarding the size or location of a cancerous growth. Cystoscopy, the main method of investigating bladder abnormalities at present, provides accurate results and can provide information regarding the relative size and location of any abnormalities. However, cystoscopy is an invasive procedure which offers a physician a limited field of view and lacks an objective indication of size. In addition, cystoscopy is contra-indicated for those patients who have severe urethral strictures or active vesical bleeding. Thus, it is desirable to develop alternative procedures for screening patients for bladder cancer, especially at early stages of cancer development.

Two-dimensional ("2D") visualization of human organs employing currently available medical imaging devices, such as computed tomography and MRI (magnetic resonance imaging), has been widely used for patient diagnosis. Three-dimensional images can be formed by stacking and interpolating between two-dimensional pictures produced from the scanning machines. Imaging an organ and visualeficial due to its lack of physical intrusion and the ease of data manipulation. However, the exploration of the three-dimensional volume image must be properly performed in order to fully exploit the advantages of virtually viewing an organ from the inside.

When viewing the three dimensional ("3D") volume virtual image of an environment, a functional model must be used to explore the virtual space. One possible model is a virtual camera which can be used as a point of reference for the viewer to explore the virtual space. Camera control in the context of navigation within a general 3D virtual environment has been previously studied. There are two conventional types of camera control offered for navigation of virtual space. The first gives the operator full control of the camera which allows the operator to manipulate the camera in different positions and orientations to achieve the view desired. The operator will in effect pilot the camera. This allows the operator to explore a particular section of interest while ignoring other sections. However, complete control of a camera in a large domain would be tedious and tiring, and an operator might not view all the important features between the start and finishing point of the exploration.

The second technique of camera control is a planned navigation method, which assigns the camera a predetermined path to take and which cannot be changed by the operator. This is akin to having an engaged "autopilot". This allows the operator to concentrate on the virtual space being viewed, and not have to worry about steering into walls of the environment being examined. However, this second technique does not give the viewer the flexibility to alter the course or investigate an interesting area viewed along the flight path.

It would be desirable to use a combination of the two navigation techniques described above to realize the advantages of both techniques while minimizing their respective drawbacks. It would be desirable to apply a flexible navigation technique to the examination of human or animal organs which are represented in virtual 3D space in order to perform a non-intrusive painless thorough examination. The desired navigation technique would further allow for a complete examination of a virtual organ in 3D space by an operator allowing flexibility while ensuring a smooth path and complete examination through and around the organ. It would be additionally desirable to be able to display the exploration of the organ in a real time setting by using a technique which minimizes the computations necessary for viewing the organ. The desired technique should also be equally applicable to exploring any virtual object.

It is another object of the invention to assign opacity coefficients to each volume element in the representation in order to make particular volume elements transparent or translucent to varying degrees in order to customize the visualization of the portion of the object being viewed. A section of the object can also be composited using the opacity coefficients.

SUMMARY OF THE INVENTION

The invention generates a three-dimensional visualization image of an object such as a human organ using volume visualization techniques and explores the virtual image using a guided navigation system which allows the operator to travel along a predefined flight path and to adjust both the position and viewing angle to a particular portion of interest in the image away from the predefined path in order to identify polyps, cysts or other abnormal features in the organ.

A method for performing virtual examination of an object includes performing at least one imaging scan of an object with the object distended by the presence of a contrast agent. In addition, at least one imaging scan of the object is acquired with the object relieved of the contrast agent. The scans are converted to corresponding volume datasets formed with a plurality of voxels. Image segmentation is then performed to classify the voxels of each scan into a plurality of categories. The volume datasets of each scan are registered to a common coordinate system. A displaying operation can then be performed where corresponding images at least two of the volume datasets are substantially simultaneously displayed. Virtual navigation operations performed in one of the volume datasets results in having the corresponding navigation operations take place in at least one other volume dataset.

Preferably, the at least one scan of the distended object includes a transverse scan and a coronal scan of the object. Similarly, it is preferable that the at least one scan of the relieved object includes a transverse scan and a coronal scan of the object. This procedure is particularly well suited for performing virtual cystoscopy, where the object is the bladder. In this case, the scan generally takes the form of a magnetic resonance imaging scan and the contrast agent can be urine.

Another method in accordance with the present invention is for performing virtual examination of an object. In this method, an imaging scan of the object is performed to acquire image scan data. The acquired image scan data is converted to a plurality of volume units, or voxels. By interpolating between the voxels, an expanded dataset is generated. Image segmentation can then be performed to classify the voxels into a plurality of categories. A volume of the object interior is extracted from the expanded dataset, such as by using a region growing algorithm from a seed voxel within the object lumen. A reduced resolution dataset is then generated from the expanded dataset. To efficiently store and recall the data from the expanded data set, this data is stored in a tree data structure. Images can then be rendered for both the expanded dataset and reduced resolution dataset. One of these images is then selected for viewing. Generally, the reduced resolution dataset is selected during navigation or image interaction whereas the expanded dataset is selected for high resolution, static display.

A method of performing virtual angiography is also provided. In this method, imaging scan data is acquired of at least a portion of the aorta. The imaging scan data is converted to a volume representation including a plurality of voxels. The volume representation is segmented to classify the voxels into one of a plurality of categories. The segmented volume representation is then analyzed to identify voxels indicative of at least a portion of an aneurysm in the aortic wall. From the portions of the aneurysm which are identified, at least one closing surface is generated around the voxels indicative of at least a portion of an aneurysm. The closing surface provides an estimate of the contour of the aneurysm. A navigation path can be established through the aortic lumen and characteristics of the aneurysm, such as length, diameter, volume and composition, can be determined.

The method of performing virtual angiography can be used to detect and monitor the progression of aneurysms and can also be used in determining the characteristics needed to place a stent graft.

Also provided is a method of defining a skeleton for a three dimensional image representation of a hollow object formed with a plurality of voxels. A root voxel is first identified within the hollow object. A distance map is then generated for all voxels within the hollow object. The distance map is formed using a 26-connected cubic plate having Euclidian weighted distances. Those voxels having a local maxima in the distance map are identified as endpoints of branches in the hollow object. For each local maxima voxel, a shortest connected path to either the root voxel or a previously defined shortest path, is determined. The collection of shortest paths is the rough skeleton of the object. This technique is particularly well suited for multibranch structures such as the respiratory system and cardio vascular system.

BRIEF DESCRIPTION OF THE DRAWINGS

Further objects, features and advantages of the invention will become apparent from the following detailed description taken in conjunction with the accompanying figures showing a preferred embodiment of the invention, on which:

FIGS. 33A–C are pictorial views of a portion of the aorta illustrating the presence of an abdominal aortic aneurysm.

FIG. 36 is a diagram illustrating pseudo-code of a process for generating a distance map for use in the method of FIG. 34.

DETAILED DESCRIPTION OF PREFERRED EMBODIMENTS

While the methods and systems described in this application can be applied to any object to be examined, the preferred embodiment which will be described is the examination of an organ in the human body, specifically the colon. The colon is long and twisted which makes it especially suited for a virtual examination saving the patient both money and the discomfort and danger of a physical probe. Other examples of organs which can be examined, without limitation, include the lungs, stomach and portions of the gastro-intestinal system, the heart and blood vessels.

Figure 1:
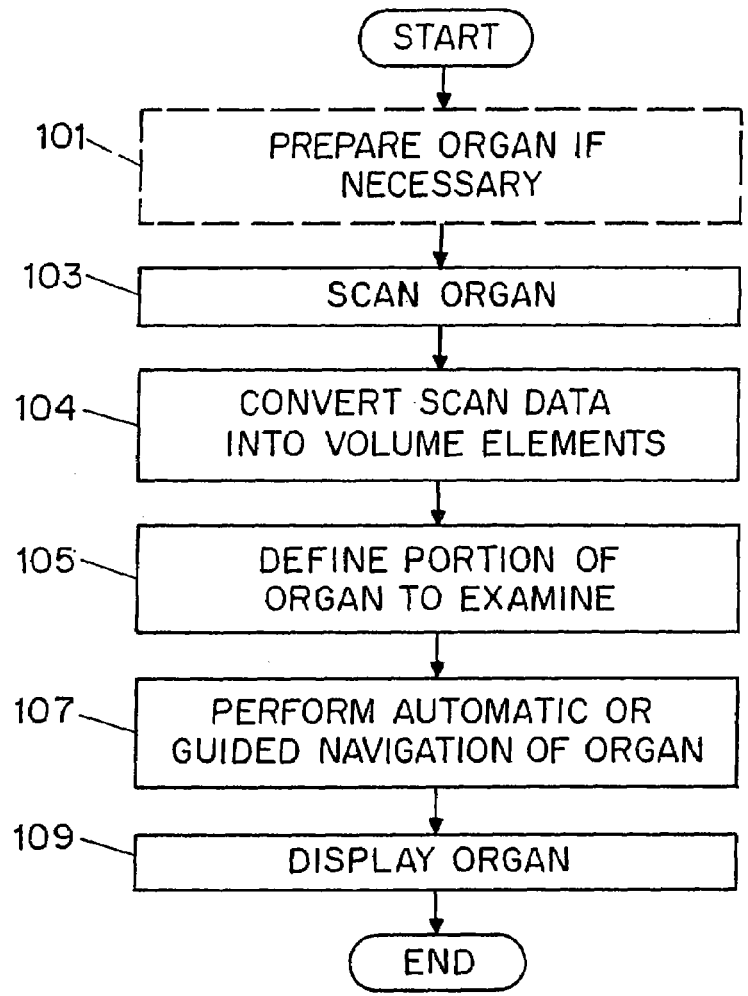
FIG. 1 is a flow chart of the steps for performing a virtual examination of an object, specifically a colon, in accordance with the invention.

FIG. 1 illustrates the steps necessary to perform a virtual colonoscopy using volume visualization techniques. Step 101 prepares the colon to be scanned in order to be viewed for examination if required by either the doctor or the particular scanning instrument. This preparation could include cleansing the colon with a "cocktail" or liquid which enters the colon after being orally ingested and passed through the stomach. The cocktail forces the patient to expel waste material that is present in the colon. One example of a substance used is Golytely. Additionally, in the case of the colon, air or $CO_2$ can be forced into the colon in order to expand it to make the colon easier to scan and examine. This is accomplished with a small tube placed in the rectum with approximately 1,000 cc of air pumped into the colon to distend the colon. Depending upon the type of scanner used, it may be necessary for the patient to drink a contrast substance such as barium to coat any unexpunged stool in order to distinguish the waste in the colon from the colon walls themselves. Alternatively, the method for virtually examining the colon can remove the virtual waste prior to or during the virtual examination as explained later in this specification. Step 101 does not need to be performed in all examinations as indicated by the dashed line in FIG. 1.

Step 103 scans the organ which is to be examined. The scanner can be an apparatus well known in the art, such as a spiral CT-scanner for scanning a colon or a Zenita MRI machine for scanning a lung labeled for example with xenon gas. The scanner must be able to take multiple images from different positions around the body during suspended respiration, in order to produce the data necessary for the volume visualization. An example of a single CT-image would use an X-ray beam of 5 mm width, 1:1 to 2:1 pitch, with a 40 cm field-of-view being performed from the top of the splenic flexure of the colon to the rectum.

Discrete data representations of said object can be produced by other methods besides scanning. Voxel data representing an object can be derived from a geometric model by techniques described in U.S. Pat. No. 5,038,302 entitled "Method of Converting Continuous Three-Dimensional Geometrical Representations into Discrete Three-Dimensional Voxel-Based Representations Within a Three-Dimensional Voxel-Based System" by Kaufman, issued Aug. 8, 1991, filed Jul. 26, 1988, which is hereby incorporated by reference. Additionally, data can be produced by a computer model of an image which can be converted to three-dimension voxels and explored in accordance with this invention. One example of this type of data is a computer simulation of the turbulence surrounding a space shuttle craft.

Step 104 converts the scanned images into three-dimensional volume elements (Voxels). In the preferred embodiment for examining a colon, the scan data is reformatted into 5 mm thick slices at increments of 1 mm or 2.5 mm and reconstructed in 1 mm slices, with each slice represented as a matrix of 512 by 512 pixels. By doing this, voxels of approximately 1 cubic mm are created. Thus a large number of 2D slices are generated depending upon the length of the scan. The set of 2D slices is then reconstructed to 3D voxels. The conversion process of 2D images from the scanner into 3D voxels can either be performed by the scanning machine itself or by a separate machine such as a computer with techniques which are well known in the art (for example, see U.S. Pat. No. 4,985,856 entitled "Method and Apparatus for Storing, Accessing, and Processing Voxel-based Data" by Kaufman et al.; issued Jan. 15, 1991, filed Nov. 11, 1988; which is hereby incorporated by reference).

Step 105 allows the operator to define the portion of the selected organ to be examined. A physician may be interested in a particular section of the colon likely to develop polyps. The physician can view a two dimensional slice overview map to indicate the section to be examined. A starting point and finishing point of a path to be viewed can be indicated by the physician/operator. A conventional computer and computer interface (e.g., keyboard, mouse or spaceball) can be used to designate the portion of the colon which is to be inspected. A grid system with coordinates can be used for keyboard entry or the physician/operator can "click" on the desired points. The entire image of the colon can also be viewed if desired.

Step 107 performs the planned or guided navigation operation of the virtual organ being examined. Performing a guided navigation operation is defined as navigating through an environment along a predefined or automatically predetermined flight path which can be manually adjusted by an operator at any time. After the scan data has been converted to 3D voxels, the inside of the organ must be traversed from the selected start to the selected finishing point. The virtual examinations is modeled on having a tiny camera traveling through the virtual space with a lens pointing towards the finishing point. The guided navigation technique provides a level of interaction with the camera, so that the camera can navigate through a virtual environment automatically in the case of no operator interaction, and at the same time, allow the operator to manipulate the camera when necessary. The preferred embodiment of achieving guided navigation is to use a physically based camera model which employs potential fields to control the movement of the camera and which are described in detail in FIGS. 2 and 3.

Figure 9:
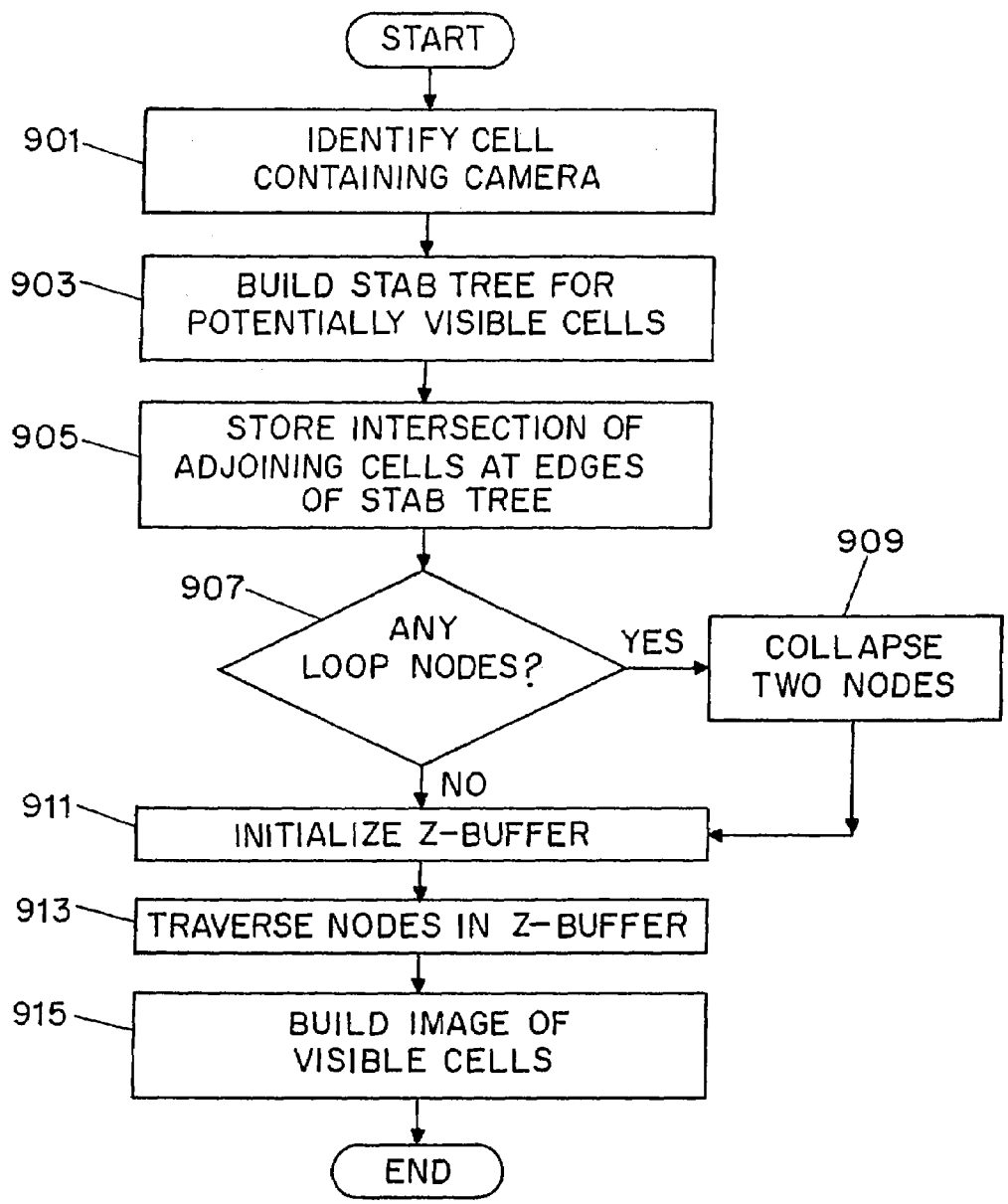
FIG. 9 is a flow chart of the steps of generating a volume visualization of the scanned organ.

Step 109, which can be performed concurrently with step 107, displays the inside of the organ from the viewpoint of the camera model along the selected pathway of the guided navigation operation. Three-dimensional displays can be generated using techniques well known in the art such as the marching cubes technique. However, in order to produce a real time display of the colon, a technique is required which reduces the vast number of computations of data necessary for the display of the virtual organ. FIG. 9 describe this display step in more detail.

The method described in FIG. 1 can also be applied to scanning multiple organs in a body at the same time. For example, a patient may be examined for cancerous growths in both the colon and lungs. The method of FIG. 1 would be modified to scan all the areas of interest in step 103 and to select the current organ to be examined in step 105. For example, the physician/operator may initially select the colon to virtually explore and later explore the lung. Alternatively, two different doctors with different specialties may virtually explore different scanned organs relating to their respective specialties. Following step 109, the next organ to be examined is selected and its portion will be defined and explored. This continues until all organs which need examination have been processed.

The steps described in conjunction with FIG. 1 can also be applied to the exploration of any object which can be represented by volume elements. For example, an architectural structure or inanimate object can be represented and explored in the same manner.

Figure 2:
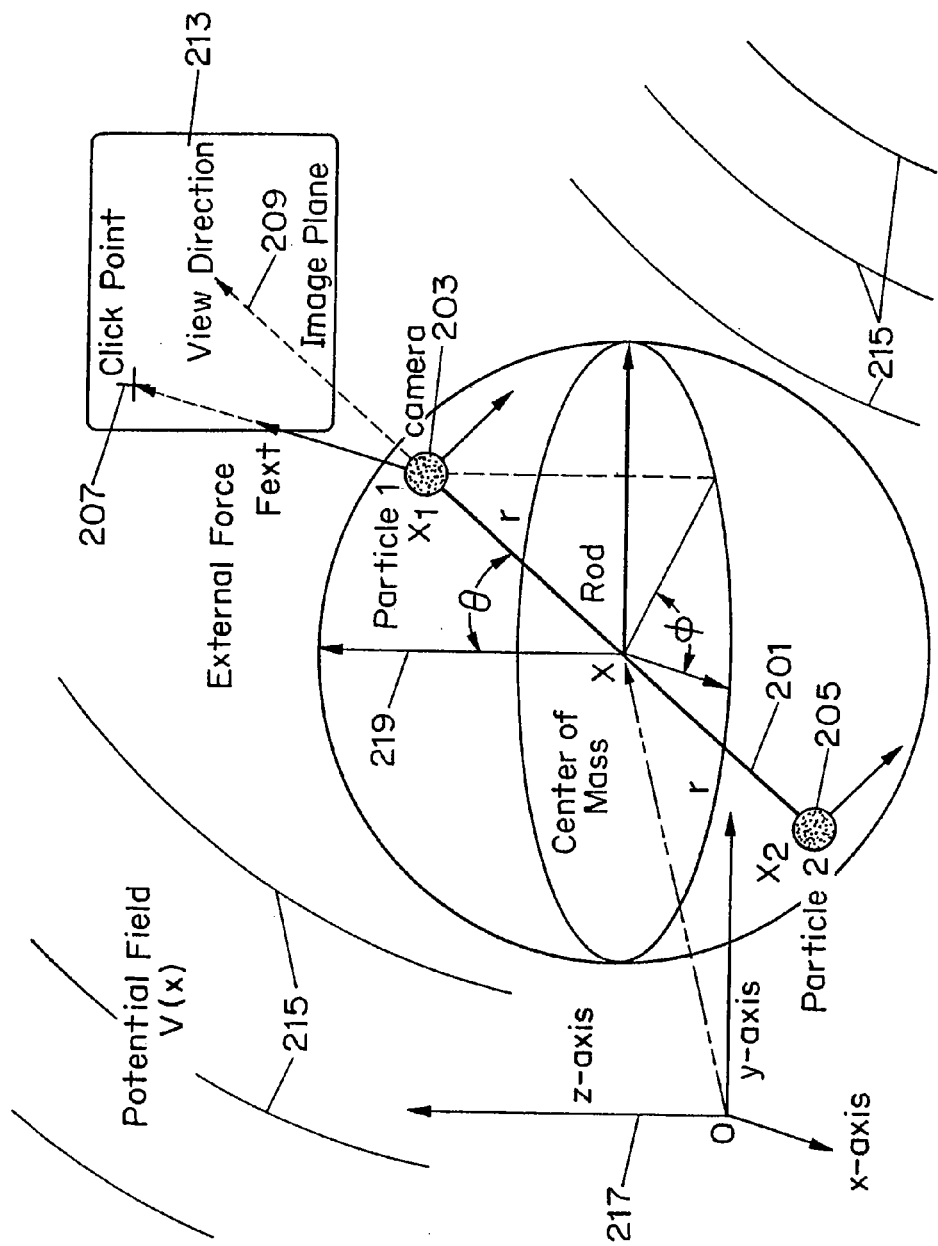
FIG. 2 is an illustration of a "submarine" camera model which performs guided navigation in the virtual organ.

FIG. 2 depicts a "submarine" camera control model which performs the guided navigation technique in step 107. When there is no operator control during guided navigation, the default navigation is similar to that of planned navigation which automatically directs the camera along a flight path from one selected end of the colon to another. During the planned navigation phase, the camera stays at the center of the colon for obtaining better views of the colonic surface. When an interesting region is encountered, the operator of the virtual camera using guided navigation can interactively bring the camera close to a specific region and direct the motion and angle of the camera to study the interesting area in detail, without unwillingly colliding with the walls of the colon. The operator can control the camera with a standard interface device such as a keyboard, mouse or non-standard device such as a spaceball. In order to fully operate a camera in a virtual environment, six degrees of freedom for the camera is required. The camera must be able to move in the horizontal, vertical, and Z direction (axes 217), as well as being able to rotate in another three degrees of freedom (axes 219) to allow the camera to move and scan all sides and angles of a virtual environment. The camera model for guided navigation includes an inextensible, weightless rod 201 connecting two particles $x_1$ 203 and $X_2$ 205, both particles being subjected to a potential field 215. The potential field is defined to be highest at the walls of the organ in order to push the camera away from the walls.

The positions of the particles are given by $x_1$ and $x_2$, and they are assumed to have the same mass m. A camera is attached at the head of the submarine $x_1$ 203, whose viewing direction coincides with $x_2 x_1$. The submarine can perform translation and rotation around the center of mass x of the model as the two particles are affected by the forces from the potential field $V(x)$ which is defined below, any friction forces, and any simulated external force. The relations between $x_1$, $x_2$, and x are as follows:

$$x = (x, y, z),$$
$$r = (r \sin \theta \cos \phi, r \sin \theta \sin \phi, r \cos \theta),$$
$$x_1 = x + r,$$
$$x_2 = x - r, \quad (1)$$

where r, $\theta$ and $\phi$ are the polar coordinates of the vector $xx_1$. The kinetic energy of the model, T, is defined as the summation of the kinetic energies of the movements of $x_1$ and $X_2$:

$$T = \frac{m}{2}(\dot{x}_1^2 + \dot{x}_2^2) \quad (2)$$
$$= m\dot{x}^2 + m\dot{r}^2$$
$$= m(\dot{x}^2 + \dot{y}^2 + \dot{z}^2) + mr^2(\dot{\theta}^2 + \dot{\phi}^2 \sin^2\theta).$$

Then, the equations for the motion of the submarine model are obtained by using LaGrange's equation:

$$\frac{d}{dt}\left(\frac{\partial T}{\partial \dot{q}_j}\right) - \frac{\partial T}{\partial q_j} = \sum_{i=1}^{2}\left(F_i \cdot \frac{\partial x_i}{\partial q_j}\right), \quad (3)$$

where the $q_j$s are the generalized coordinates of the model and can be considered as the variables of time t as:

$$(q_1, q_2, q_3, q_4, q_5, q_6) = (x, y, z, \theta, \phi, \psi) = q(t), \quad (4)$$

with $\psi$ denoting the roll angle of our camera system, which will be explained later. The $F_i$s are called the generalized forces. The control of the submarine is performed by applying a simulated external force to $x_1$, $$F_{ext} = (F_x, F_y, F_z),$$

and it is assumed that both $x_1$ and $x_2$ are affected by the forces from the potential field and the frictions which act in the opposite direction of each particle's velocity. Consequently, the generalized forces are formulated as follows:

$$F_1 = -m\nabla V(x_1) - k\dot{x}_1 + F_{ext},$$
$$F_2 = -m\nabla V(x_2) - k\dot{x}_2, \quad (5)$$

where k denotes the friction coefficient of the system. The external force $F_{ext}$ is applied by the operator by simply clicking the mouse button in the desired direction 207 in the generated image, as shown in FIG. 2. This camera model would then be moved in that direction. This allows the operator to control at least five degrees of freedom of the camera with only a single click of the mouse button. From Equations (2), (3) and (5), it can be derived that the accelerations of the five parameters of our submarine model as:

$$\ddot{x} = -\frac{1}{2}\left(\frac{\partial V(x_1)}{\partial x} + \frac{\partial V(x_2)}{\partial x}\right) - \frac{k\dot{x}}{m} + \frac{F_x}{2m}, \quad (6)$$
$$\ddot{y} = -\frac{1}{2}\left(\frac{\partial V(x_1)}{\partial y} + \frac{\partial V(x_2)}{\partial y}\right) - \frac{k\dot{y}}{m} + \frac{F_y}{2m},$$

-continued
$$\ddot{z} = -\frac{1}{2}\left(\frac{\partial V(x_1)}{\partial z} + \frac{\partial V(x_2)}{\partial z}\right) - \frac{kz}{m} + \frac{F_z}{2m},$$
$$\ddot{\theta} = \dot{\phi}^2 \sin\theta\cos\theta - \frac{1}{2r}\Big[\cos\theta\Big\{\cos\phi\Big(\frac{\partial V(x_1)}{\partial x} - \frac{\partial V(x_2)}{\partial x}\Big) +$$
$$\sin\phi\Big(\frac{\partial V(x_1)}{\partial y} - \frac{\partial V(x_2)}{\partial y}\Big)\Big\} -$$
$$\sin\theta\Big(\frac{\partial V(x_1)}{\partial z} - \frac{\partial V(x_2)}{\partial z}\Big)\Big] - \frac{k}{m}\dot{\theta} +$$
$$\frac{1}{2mr}(F_x \cos\theta\cos\phi + F_y \cos\theta\sin\phi - F_z \sin\theta),$$
$$\ddot{\phi} = \frac{1}{\sin\theta}\Big[-2\dot{\theta}\dot{\phi}\cos\theta - \frac{1}{2r}\Big\{-\sin\phi\Big(\frac{\partial V(x_1)}{\partial x} - \frac{\partial V(x_2)}{\partial x}\Big) +$$
$$\cos\phi\Big(\frac{\partial V(x_1)}{\partial y} - \frac{\partial V(x_2)}{\partial y}\Big)\Big\} -$$
$$\frac{k}{m}\dot{\phi}\sin\theta + \frac{1}{2mr}(-F_x \sin\phi + F_y \cos\phi)\Big],$$

where $\dot{x}$ and $\ddot{x}$ denote the first and the second derivative of x, respectively, and $$\left(\frac{\partial V(x)}{\partial x}, \frac{\partial V(x)}{\partial y}, \frac{\partial V(x)}{\partial z}\right)$$

denotes the gradient of the potential at a point x. The terms $\dot{\phi}^2 \sin\theta \cos\theta$ of $\ddot{\theta}$ and $$-\frac{2\dot{\theta}\dot{\phi}\cos\theta}{\sin\theta}$$

of $\ddot{\phi}$ are called the centrifugal force and the Coriolis force, respectively, and they are concerned with the exchange of angular velocities of the submarine. Since the model does not have the moment of inertia defined for the rod of the submarine, these terms tend to cause an overflow of the numeric calculation of $\phi$. Fortunately, these terms become significant only when the angular velocities of the submarine model are significant, which essentially means that the camera moves too fast. Since it is meaningless to allow the camera to move so fast because the organ could not be properly viewed, these terms are minimized in our implementation to avoid the overflow problem.

From the first three formulas of Equation (6), it is known that the submarine cannot be propelled by the external force against the potential field if the following condition is satisfied:

$$|\nabla V(x_1) + \nabla V(x_2)| > \frac{|F_{ext}|}{m}.$$

Since the velocity of the submarine and the external force $F_{ext}$ have upper limits in our implementation, by assigning sufficiently high potential values at the boundary of the objects, it can be guaranteed that the submarine never bumps against the objects or walls in the environment.

Figure 3:
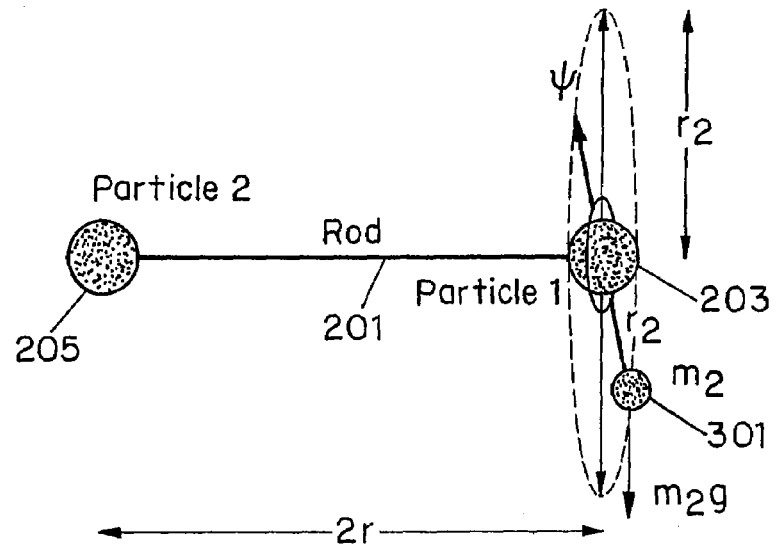
FIG. 3 is an illustration of a pendulum used to model pitch and roll of the "submarine" camera.

As mentioned previously, the roll angle $\psi$ of the camera system needs to be considered. One possible option allows the operator full control of the angle ψ. However, although the operator can rotate the camera freely around the rod of the model, he or she can easily become disoriented. The preferred technique assumes that the upper direction of the camera is connected to a pendulum with mass $m_2$ 301, which rotates freely around the rod of the submarine, as shown in FIG. 3. The direction of the pendulum, $r_2$, is expressed as:

$$r_2 = r_2(\cos\theta\cos\phi\sin\psi + \sin\phi\cos\psi\cos\theta\sin\phi\sin\psi - \cos\phi\cos\psi, -\sin\theta\sin\psi).$$

although it is possible to calculate the accurate movement of this pendulum along with the movement of the submarine, it makes the system equations too complicated. Therefore, it is assumed that all the generalized coordinates except the roll angle ψ are constants, and thus define the independent kinetic energy for the pendulum system as:

$$T_p = \frac{m_2}{2}\dot{r}_2^2 = \frac{m_2 r_2^2}{2}\dot{\psi}^2.$$

This simplifies the model for the roll angle. Since it is assumed in this model that the gravitational force $$F_g = m_2 g = (m_w g_x, m_2 g_y, m_2 g_z)$$

acts at the mass point $m_2$, the acceleration of ψ can be derived using LaGrange's equation as:

$$\ddot{\psi} = \frac{1}{r_2}\{g_x(\cos\theta\cos\phi\cos\psi - \sin\phi\sin\psi) + g_y(\cos\theta\sin\phi\cos\psi + \cos\phi\sin\psi) + g_z(-\sin\theta\cos\psi)\} - \frac{k_2}{m_2}\dot{\psi}. \quad (7)$$

From Equations (6) and (7), the generalized coordinates q(t) and their derivatives q(t) are calculated asymptotically by using Taylor series as:

$$q(t+h) = q(t) + h\dot{q}(t) + \frac{h^2}{2}\ddot{q}(t) + O(h^3),$$

$$\dot{q}(t+h) = \dot{q}(t) + h\ddot{q}(t) + O(h^2),$$

to freely move the submarine. To smooth the submarine's motion, the time step h is selected as an equilibrium value between being as small as possible to smooth the motion but as large as necessary to reduce computation cost.

Definition of the Potential Field

The potential field in the submarine model in FIG. 2 defines the boundaries (walls or other matter) in the virtual organ by assigning a high potential to the boundary in order to ensure that the submarine camera does not collide with the walls or other boundary. If the camera model is attempted to be moved into a high potential area by the operator, the camera model will be restrained from doing so unless the operator wishes to examine the organ behind the boundary or inside a polyp, for example. In the case of performing a virtual colonoscopy, a potential field value is assigned to each piece of volumetric colon data (volume element).

When a particular region of interest is designated in step 105 of FIG. 1 with a start and finish point, the voxels within the selected area of the scanned colon are identified using conventional blocking operations. Subsequently, a potential value is assigned to every voxel x of the selected volume based on the following three distance values: the distance from the finishing point dt(x), the distance from the colon surface ds(x) and the distance from the center-line of the colon space dc(x). dt(x) is calculated by using a conventional growing strategy. The distance from the colon surface, ds(x), is computed using a conventional technique of growing from the surface voxels inwards. To determine dc(x), the center-line of the colon from the voxel is first extracted, and then dc(x) is computed using the conventional growing strategy from the center-line of the colon.

To calculate the center-line of the selected colon area defined by the user-specified start point and the user-specified finish point, the maximum value of ds(x) is located and denoted dmax. Then for each voxel inside the area of interest, a cost value of dmax−ds(x) is assigned. Thus the voxels which are close to the colon surface have high cost values and the voxels close to the center line have relatively low cost values. Then, based on the cost assignment, the single-source shortest path technique which is well known in the art is applied to efficiently compute a minimum cost path from the source point to the finish point. This low cost line indicates the center-line or skeleton of the colon section which is desired to be explored. This technique for determining the center-line is the preferred technique of the invention.

To compute the potential value V(x) for a voxel x inside the area of interest, the following formula is employed:

$$V(x) = C_1 d_t(x)^\mu + C_2\left(\frac{d_s(x)}{d_c(x) + d_s(x)}\right)^{-\nu}, \quad (8)$$

where $C_1$, $C_2$, μ and ν are constants chosen for the task. In order to avoid any collision between the virtual camera and the virtual colonic surface, a sufficiently large potential value is assigned for all points outside the colon. The gradient of the potential field will therefore become so significant that the submarine model camera will never collide with the colonic wall when being run.

Another technique to determine the center-line of the path in the colon is called the "peel-layer" technique and is shown in FIG. 4 through FIG. 8.

Figure 4:
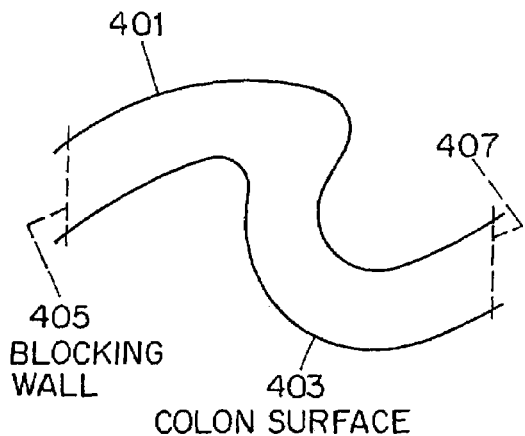
FIG. 4 is a diagram illustrating a two dimensional cross-section of a volumetric colon which identifies two blocking walls.

FIG. 4 shows a 2D cross-section of the volumetric colon, with the two side walls 401 and 403 of the colon being shown. Two blocking walls are selected by the operator in order to define the section of the colon which is of interest to examine. Nothing can be viewed beyond the blocking walls. This helps reduce the number of computations when displaying the virtual representation. The blocking walls together with side walls identify a contained volumetric shape of the colon which is to be explored.

Figure 5:
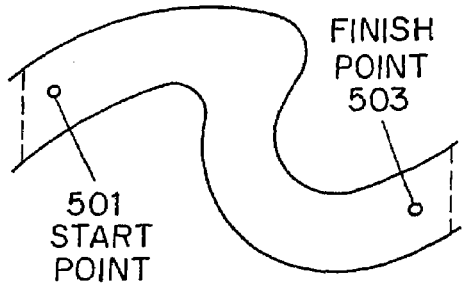
FIG. 5 is a diagram illustrating a two dimensional cross-section of a volumetric colon upon which start and finish volume elements are selected.

FIG. 5 shows two end points of the flight path of the virtual examination, the start volume element 501 and the finish volume element 503. The start and finish points are selected by the operator in step 105 of FIG. 1. The voxels between the start and finish points and the colon sides are identified and marked, as indicated by the area designated with "x"s in FIG. 6. The voxels are three-dimensional representations of the picture element.

Figure 6:
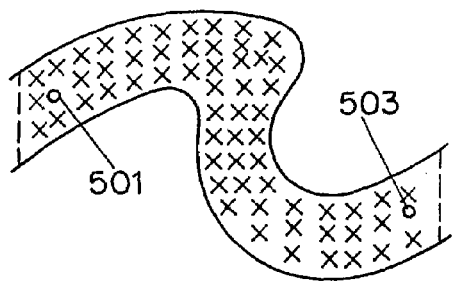
FIG. 6 is a diagram illustrating a two dimensional cross-section of a volumetric colon which shows a discrete sub-volume enclosed by the blocking walls and the colon surface.
Figure 7:
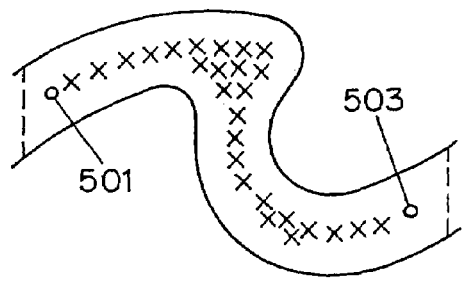
FIG. 7 is a diagram illustrating a two dimensional cross-section of a volumetric colon which has multiple layers peeled away.
Figure 8:
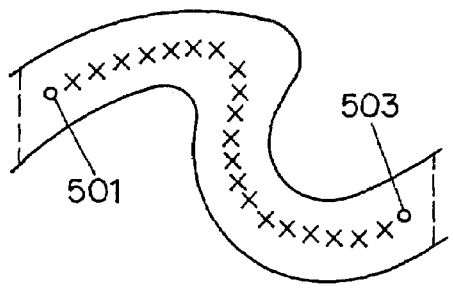
FIG. 8 is a diagram illustrating a two dimensional cross-section of a volumetric colon which contains the remaining flight path.

The peel-layer technique is then applied to the identified and marked voxels in FIG. 6. The outermost layer of all the voxels (closest to the colon walls) is peeled off step-by-step, until there is only one inner layer of voxels remaining. Stated differently, each voxel furthest away from a center point is removed if the removal does not lead to a disconnection of the path between the start voxel and the finish voxel. FIG. 7 shows the intermediate result after a number of iterations of peeling the voxels in the virtual colon are complete. The voxels closest to the walls of the colon have been removed. FIG. 8 shows the final flight path for the camera model down the center of the colon after all the peeling iterations are complete. This produces essentially a skeleton at the center of the colon and becomes the desired flight path for the camera model.

Z-Buffer Assisted Visibility

FIG. 9 describes a real time visibility technique to display of virtual images seen by the camera model in the virtual three-dimensional volume representation of an organ. FIG. 9 shows a display technique using a modified Z buffer which corresponds to step 109 in FIG. 1. The number of voxels which could be possibly viewed from the camera model is extremely large. Unless the total number of elements (or polygons) which must be computed and visualized is reduced from an entire set of voxels in the scanned environment, the overall number of computations will make the visualization display process exceedingly slow for a large internal area. However, in the present invention only those images which are visible on the colon surface need to be computed for display. The scanned environment can be subdivided into smaller sections, or cells. The Z buffer technique then renders only a portion of the cells which are visible from the camera. The Z buffer technique is also used for three-dimensional voxel representations. The use of a modified Z buffer reduces the number of visible voxels to be computed and allows for the real time examination of the virtual colon by a physician or medical technician.

Figure 10:
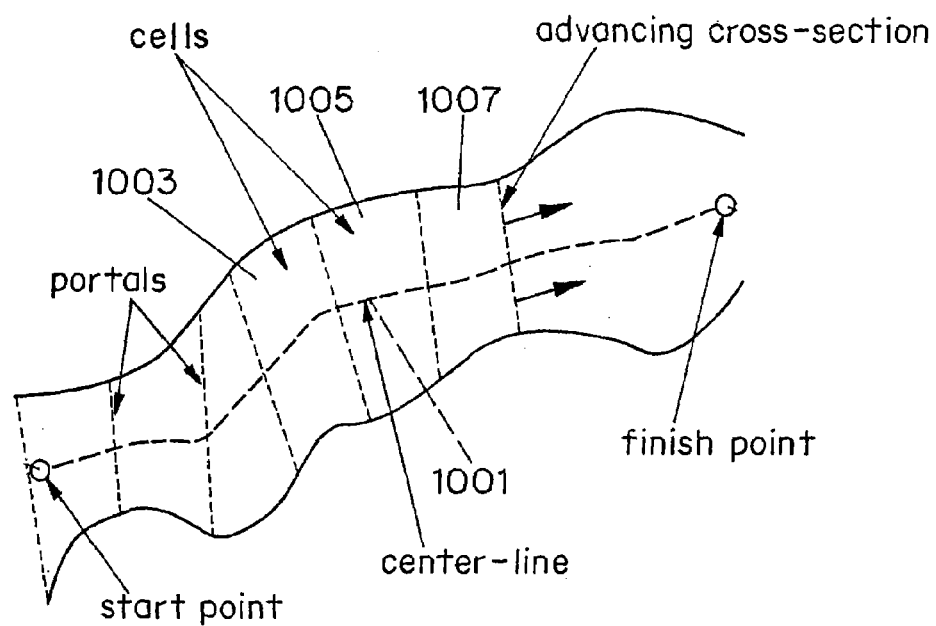
FIG. 10 is an illustration of a virtual colon which has been sub-divided into cells.

The area of interest from which the center-line has been calculated in step 107 is subdivided into cells before the display technique is applied. Cells are collective groups of voxels which become a visibility unit. The voxels in each cell will be displayed as a group. Each cell contains a number of portals through which the other cells can be viewed. The colon is subdivided by beginning at the selected start point and moving along the center-line 1001 towards the finish point. The colon is then partitioned into cells (for example, cells 1003, 1005 and 1007 in FIG. 10) when a predefined threshold distance along the center-path is reached. The threshold distance is based upon the specifications of the platform upon which the visualization technique is performed and its capabilities of storage and processing. The cell size is directly related to the number of voxels which can be stored and processed by the platform. One example of a threshold distance is 5 cm, although the distance can greatly vary. Each cell has two cross-sections as portals for viewing outside of the cell as shown in FIG. 10.

Step 901 in FIG. 9 identifies the cell within the selected organ which currently contains the camera. The current cell will be displayed as well as all other cells which are visible given the orientation of the camera. Step 903 builds a stab tree (tree diagram) of hierarchical data of potentially visible cells from the camera (through defined portals), as will be described in further detail hereinbelow. The stab tree contains a node for every cell which may be visible to the camera. Some of the cells may be transparent without any blocking bodies present so that more than one cell will be visible in a single direction. Step 905 stores a subset of the voxels from a cell which include the intersection of adjoining cell edges and stores them at the outside edge of the stab tree in order to more efficiently determine which cells are visible.

Step 907 checks if any loop nodes are present in the stab tree. A loop node occurs when two or more edges of a single cell both border on the same nearby cell. This may occur when a single cell is surrounded by another cell. If a loop node is identified in the stab tree, the method continues with step 909. If there is no loop node, the process goes to step 911.

Step 909 collapses the two cells making up the loop node into one large node. The stab tree is then corrected accordingly. This eliminates the problem of viewing the same cell twice because of a loop node. The step is performed on all identified loop nodes. The process then continues with step 911.

Step 911 then initiates the Z-buffer with the largest Z value. The Z value defines the distance away from the camera along the skeleton path. The tree is then traversed to first check the intersection values at each node. If a node intersection is covered, meaning that the current portal sequence is occluded (which is determined by the Z buffer test), then the traversal of the current branch in the tree is stopped. Step 913 traverses each of the branches to check if the nodes are covered and displays them if they are not.

Step 915 then constructs the image to be displayed on the operator's screen from the volume elements within the visible cells identified in step 913 using one of a variety of techniques known in the art, such as volume rendering by compositing. The only cells shown are those which are identified as potentially visible. This technique limits the number of cells which requires calculations in order to achieve a real time display and correspondingly increases the speed of the display for better performance. This technique is an improvement over prior techniques which calculate all the possible visible data points whether or not they are actually viewed.

Figure 11A:
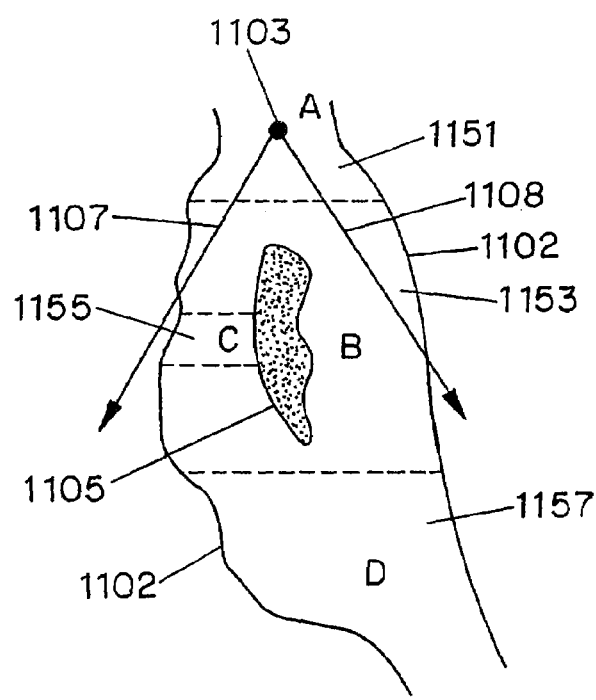
FIG. 11A is a graphical depiction of an organ which is being virtually examined.

FIG. 11A is a two dimensional pictorial representation of an organ which is being explored by guided navigation and needs to be displayed to an operator. Organ 1101 shows two side walls 1102 and an object 1105 in the center of the pathway. The organ has been divided into four cells A 1151, B 1153, C 1155 and D 1157. The camera 1103 is facing towards cell D 1157 and has a field of vision defined by vision vectors 1107, 1108 which can identify a cone-shaped field. The cells which can be potentially viewed are cells B 1153, C 1155 and D 1157. Cell C 1155 is completely surrounded by Cell B and thus constitutes a node loop.

Figures 11B, 11C:
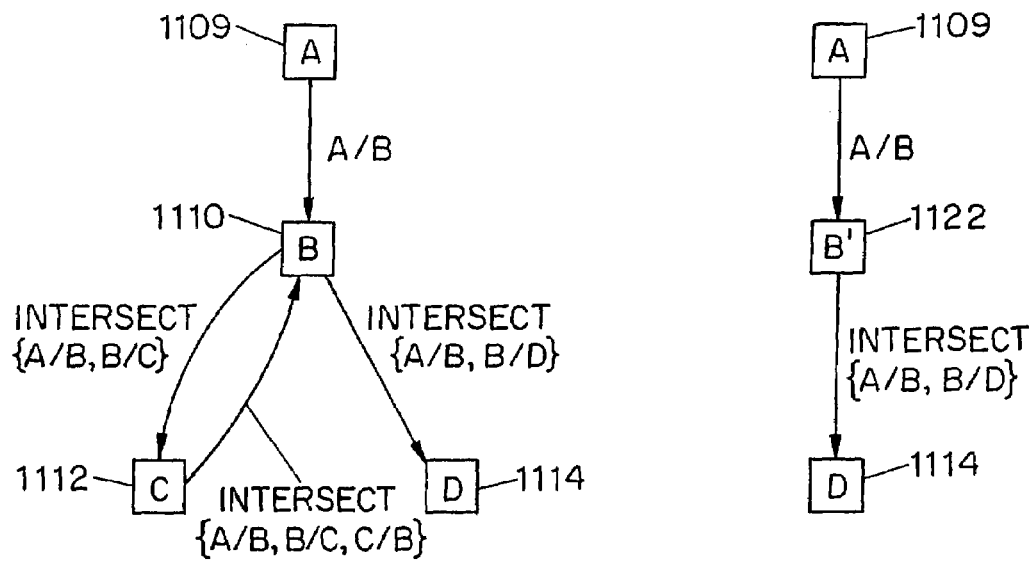
FIG. 11B is a graphical depiction of a stab tree generated when depicting the organ in FIG. 11A.
FIG. 11C is a further graphical depiction of a stab tree generated while depicting the organ in FIG. 11A.

FIG. 11B is a representation of a stab tree built from the cells in FIG. 11A. Node A 1109 which contains the camera is at the root of the tree. A sight line or sight cone, which is a visible path without being blocked, is drawn to node B 1110. Node B has direct visible sight lines to both node C 1112 and node D 1114 and which is shown by the connecting arrows. The sight line of node C 1112 in the direction of the viewing camera combines with node B 1110. Node C 1112 and node B 1110 will thus be collapsed into one large node B' 1122 as shown in FIG. 11C.

FIG. 11C shows node A 1109 containing the camera adjacent to node B' 1122 (containing both nodes B and node C) and node D 1114. The nodes A, B' and D will be displayed at least partially to the operator.

Figure 12A:
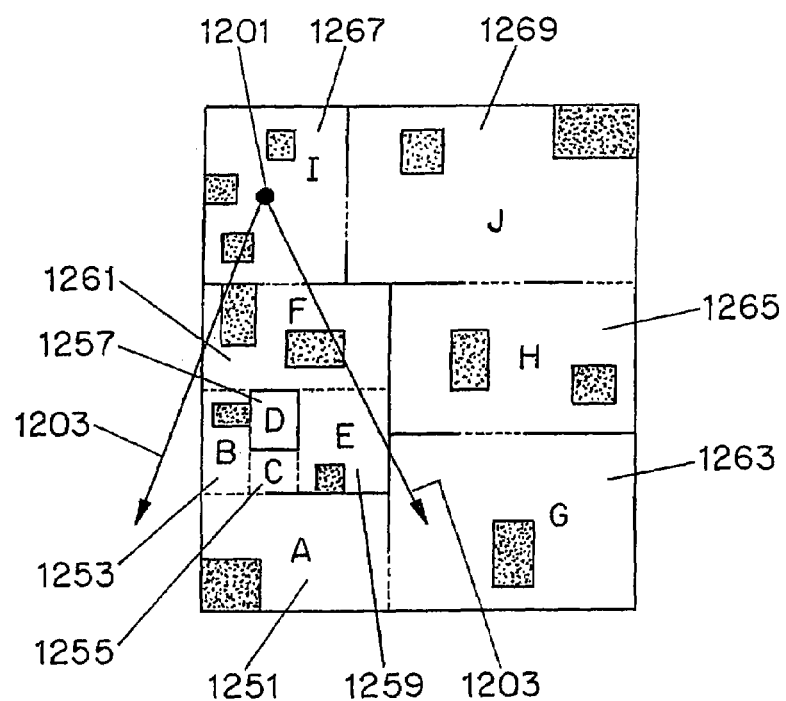
FIG. 12A is a graphical depiction of a scene to be rendered with objects within certain cells of the scene.
Figure 12B:
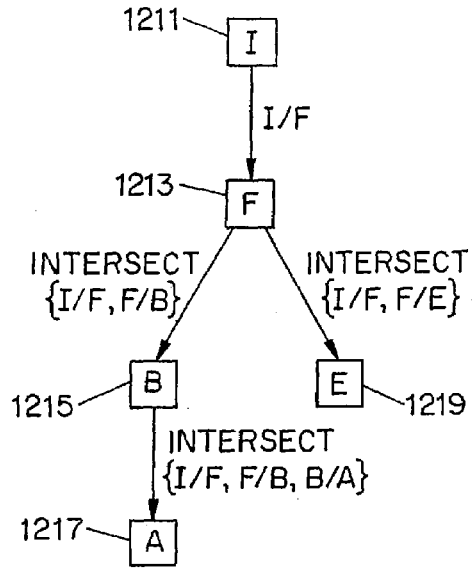
FIG. 12B is a graphical depiction of a stab tree generated while depicting the scene in FIG. 12A.

FIGS. 12A–12E illustrate the use of the modified Z buffer with cells that contain objects which obstruct the views. An object could be some waste material in a portion of the virtual colon. FIG. 12A shows a virtual space with 10 potential cells: A 1251, B 1253, C 1255, D 1257, E 1259, F 1261, G 1263, H 1265, 11267 and J 1269. Some of the cells contain objects. If the camera 1201 is positioned in cell I 1267 and is facing toward cell F 1261 as indicated by the vision vectors 1203, then a stab tree is generated in accordance with the technique illustrated by the flow diagram in FIG. 9. FIG. 12B shows the stab tree generated with the intersection nodes showing for the virtual representation as shown in FIG. 12A. FIG. 12B shows cell I 1267 as the root node of the tree because it contains the camera 1201. Node I 1211 is pointing to node F 1213 (as indicated with an arrow), because cell F is directly connected to the sight line of the camera. Node F 1213 is pointing to both node B 1215 and node E 1219. Node B 1215 is pointing to node A 1217. Node C 1202 is completely blocked from the line of sight by camera 1201 so is not included in the stab tree.

Figure 12C:
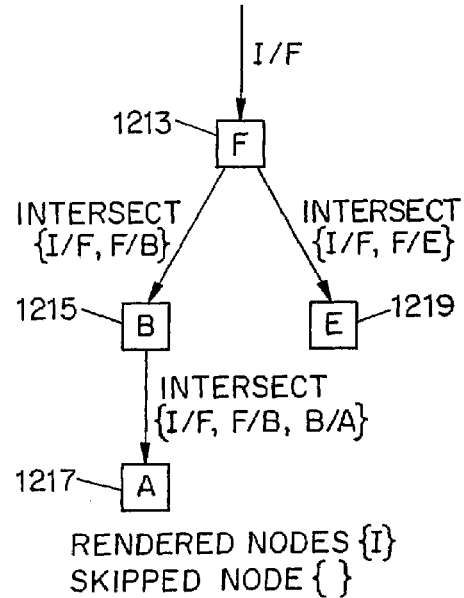
FIGS. 12C–12E are further graphical depictions of stab trees generated while depicting the image in FIG. 12A.
Figure 12D:
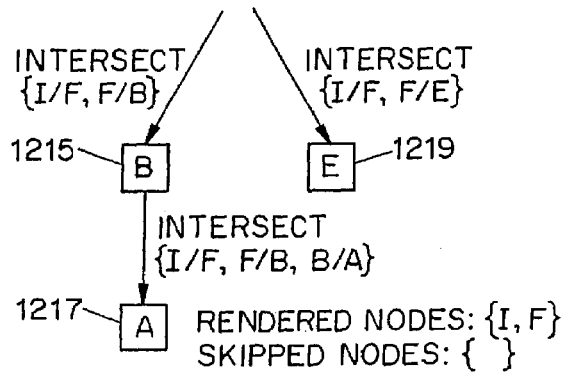

FIG. 12C shows the stab tree after node I 1211 is rendered on the display for the operator. Node I 1211 is then removed from the stab tree because it has already been displayed and node F 1213 becomes the root. FIG. 12D shows that node F 1213 is now rendered to join node I 1211. The next nodes in the tree connected by arrows are then checked to see if they are already covered (already processed). In this example, all of the intersected nodes from the camera positioned in cell I 1267 has been covered so that node B 515 (and therefore dependent node A) do not need to be rendered on the display.

Figure 12E:
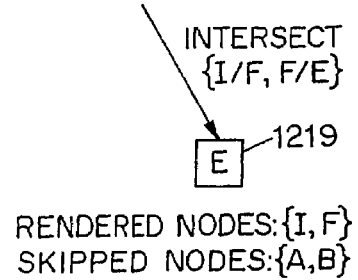

FIG. 12E shows node E 515 being checked to determine if its intersection has been covered. Since it has, the only rendered nodes in this example of FIG. 12A–12E are nodes I and F while nodes A, B and E are not visible and do not need to have their cells prepared to be displayed.

The modified Z buffer technique described in FIG. 9 allows for fewer computations and can be applied to an object which has been represented by voxels or other data elements, such as polygons.

Figure 13:
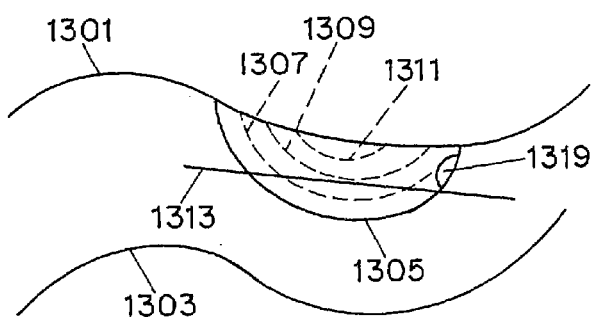
FIG. 13 is a two dimensional representation of a virtual colon containing a polyp whose layers can be removed.

FIG. 13 shows a two dimensional virtual view of a colon with a large polyp present along one of its walls. FIG. 13 shows a selected section of a patient's colon which is to be examined further. The view shows two colon walls 1301 and 1303 with the growth indicated as 1305. Layers 1307, 1309, and 1311 show inner layers of the growth. It is desirable for a physician to be able to peel the layers of the polyp or tumor away to look inside of the mass for any cancerous or other harmful material. This process would in effect perform a virtual biopsy of the mass without actually cutting into the mass. Once the colon is represented virtually by voxels, the process of peeling away layers of an object is easily performed in a similar manner as described in conjunction with FIGS. 4 through 8. The mass can also be sliced so that a particular cross-section can be examined. In FIG. 13, a planar cut 1313 can be made so that a particular portion of the growth can be examined. Additionally, a user-defined slice 1319 can be made in any manner in the growth. The voxels 1319 can either be peeled away or modified as explained below.

A transfer function can be performed to each voxel in the area of interest which can make the object transparent, semi-transparent or opaque by altering coefficients representing the translucently for each voxel. An opacity coefficient is assigned to each voxel based on its density. A mapping function then transforms the density value to a coefficient representing its translucency. A high density scanned voxel will indicate either a wall or other dense matter besides simply open space. An operator or program routine could then change the opacity coefficient of a voxel or group of voxels to make them appear transparent or semi-transparent to the submarine camera model. For example, an operator may view a tumor within or outside of an entire growth. Or a transparent voxel will be made to appear as if it is not present for the display step of FIG. 9. A composite of a section of the object can be created using a weighted average of the opacity coefficients of the voxels in that section.

If a physician desires to view the various layers of a polyp to look for a cancerous areas, this can be performed by removing the outer layer of polyp 1305 yielding a first layer 1307. Additionally, the first inner layer 1307 can be stripped back to view second inner layer 1309. The second inner layer can be stripped back to view third inner layer 1311, etc. The physician could also slice the polyp 1305 and view only those voxels within a desired section. The slicing area can be completely user-defined.

Adding an opacity coefficient can also be used in other ways to aid in the exploration of a virtual system. If waste material is present and has a density as other properties within a certain known range, the waste can be made transparent to the virtual camera by changing its opacity coefficient during the examination. This will allow the patient to avoid ingesting a bowel cleansing agent before the procedure and make the examination faster and easier. Other objects can be similarly made to disappear depending upon the actual application. Additionally, some objects like polyps could be enhanced electronically by a contrast agent followed by a use of an appropriate transfer function.

Figure 14:
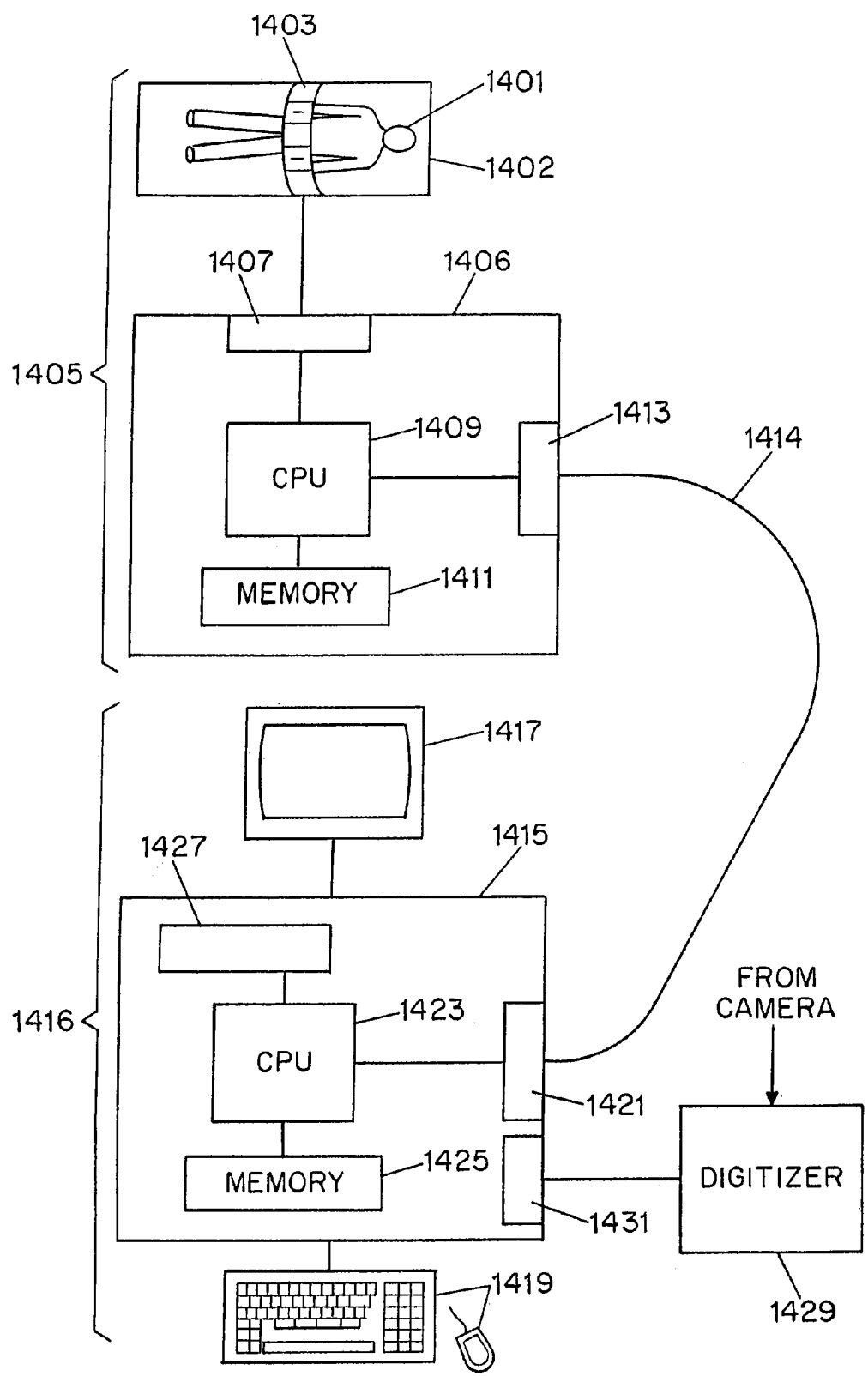
FIG. 14 is a diagram of a system used to perform a virtual examination of a human organ in accordance with the invention.

FIG. 14 shows a system for performing the virtual examination of an object such as a human organ using the techniques described in this specification. Patient 1401 lies down on a platform 1402 while scanning device 1405 scans the area that contains the organ or organs which are to be examined. The scanning device 1405 contains a scanning portion 1403 which actually takes images of the patient and an electronics portion 1406. Electronics portion 1406 comprises an interface 1407, a central processing unit 1409, a memory 1411 for temporarily storing the scanning data, and a second interface 1413 for sending data to the virtual navigation platform. Interface 1407 and 1413 could be included in a single interface component or could be the same component. The components in portion 1406 are connected together with conventional connectors.

In system 1400, the data provided from the scanning portion of device 1403 is transferred to portion 1405 for processing and is stored in memory 1411. Central processing unit 1409 converts the scanned 2D data to 3D voxel data and stores the results in another portion of memory 1411. Alternatively, the converted data could be directly sent to interface unit 1413 to be transferred to the virtual navigation terminal 1416. The conversion of the 2D data could also take place at the virtual navigation terminal 1416 after being transmitted from interface 1413. In the preferred embodiment, the converted data is transmitted over carrier 1414 to the virtual navigation terminal 1416 in order for an operator to perform the virtual examination. The data could also be transported in other conventional ways such as storing the data on a storage medium and physically transporting it to terminal 1416 or by using satellite transmissions.

The scanned data may not be converted to its 3D representation until the visualization rendering engine requires it to be in 3D form. This saves computational steps and memory storage space.

Virtual navigation terminal 1416 includes a screen for viewing the virtual organ or other scanned image, an electronics portion 1415 and interface control 1419 such as a keyboard, mouse or spaceball. Electronics portion 1415 comprises a interface port 1421, a central processing unit 1423, other components 1427 necessary to run the terminal and a memory 1425. The components in terminal 1416 are connected together with conventional connectors. The converted voxel data is received in interface port 1421 and stored in memory 1425. The central processor unit 1423 then assembles the 3D voxels into a virtual representation and runs the submarine camera model as described in FIGS. 2 and 3 to perform the virtual examination. As the submarine camera travels through the virtual organ, the visibility technique as described in FIG. 9 is used to compute only those areas which are visible from the virtual camera and displays them on screen 1417. A graphics accelerator can also be used in generating the representations. The operator can use interface device 1419 to indicate which portion of the scanned body is desired to be explored. The interface device 1419 can further be used to control and move the submarine camera as desired as discussed in FIG. 2 and its accompanying description. Terminal portion 1415 can be the Cube-4 dedicated system box, generally available from the Department of Computer Science at the State University of New York at Stony Brook.

Scanning device 1405 and terminal 1416, or parts thereof, can be part of the same unit. A single platform would be used to receive the scan image data, connect it to 3D voxels if necessary and perform the guided navigation.

An important feature in system 1400 is that the virtual organ can be examined at a later time without the presence of the patient. Additionally, the virtual examination could take place while the patient is being scanned. The scan data can also be sent to multiple terminals which would allow more than one doctor to view the inside of the organ simultaneously. Thus a doctor in New York could be looking at the same portion of a patient's organ at the same time with a doctor in California while discussing the case. Alternatively, the data can be viewed at different times. Two or more doctors could perform their own examination of the same data in a difficult case. Multiple virtual navigation terminals could be used to view the same scan data. By reproducing the organ as a virtual organ with a discrete set of data, there are a multitude of benefits in areas such as accuracy, cost and possible data manipulations.

The above described techniques can be further enhanced in virtual colonoscopy applications through the use of an improved electronic colon cleansing technique which employs modified bowel preparation operations followed by image segmentation operations, such that fluid and stool remaining in the colon during a computed tomographic (CT) or magnetic resonance imaging (MRI) scan can be detected and removed from the virtual colonoscopy images. Through the use of such techniques, conventional physical washing of the colon, and its associated inconvenience and discomfort, is minimized or completely avoided.

Figure 15:
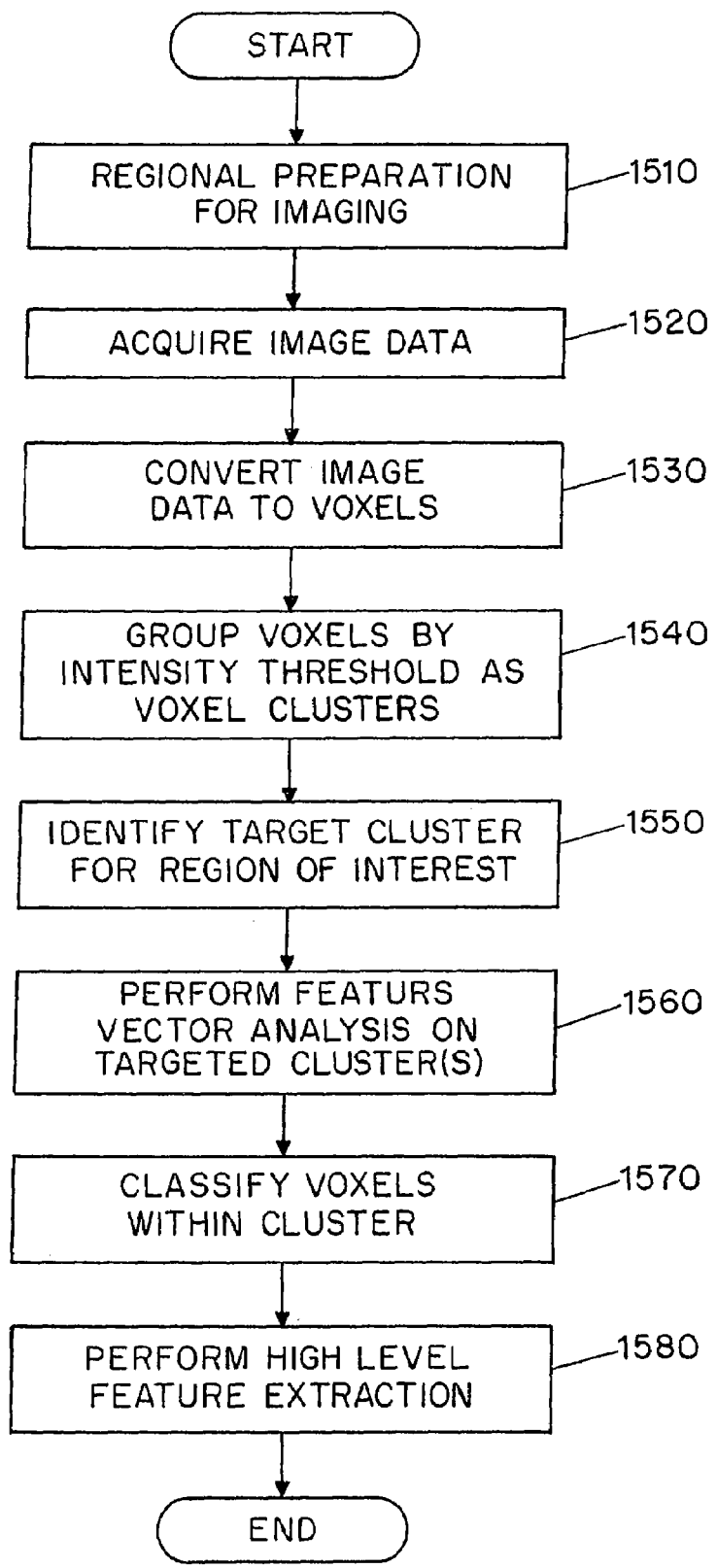
FIG. 15 is a flow chart depicting an improved image segmentation method.

Referring to FIG. 15, the first step in electronic colon cleansing is bowel preparation (step 1510), which takes place prior to conducting the CT or magnetic resonance imaging (MRI) scan and is intended to create a condition where residual stool and fluid remaining in the colon present significantly different image properties from that of the gas-filled colon interior and colon wall. An exemplary bowel preparation operation includes ingesting three 250 cc doses of Barium Sulfate suspension of 2.1% W/V, such as manufactured by E-Z-EM, Inc.,of Westbury, N.Y., during the day prior the CT or MRI scan. The three doses should be spread out over the course of the day and can be ingested along with three meals, respectively. The Barium Sulfate serves to enhance the images of any stool which remains in the colon. In addition to the intake of Barium Sulfate, fluid intake is preferably increased during the day prior to the CT or MRI scan. Cranberry juice is known to provide increased bowel fluids and is preferred, although water can also be ingested. In both the evening prior to the CT scan and the morning of the CT scan, 60 ml of a Diatrizoate Meglumine and Diaztrizoate Sodium Solution, which is commercially available as MD-Gastroview, manufactured by Mallinckrodt, Inc. of St. Louis, Mo., can be consumed to enhance image properties of the colonic fluid. Sodium phosphate can also be added to the solution to liquidize the stool in the colon, which provides for more uniform enhancement of the colonic fluid and residual stool.

The above described exemplary preliminary bowel preparation operation can obviate the need for conventional colonic washing protocols, which can call for the ingestion of a gallon of Golytely solution prior to a CT scan.

Just prior to conducting the CT scan, an intravenous injection of 1 ml of Glucagon, manufactured by Ely Lily and Company, of Indianapolis, Ind. can be administered to minimize colon collapse. Then, the colon can be inflated using approximately 1000 cc of compressed gas, such as $CO_2$, or room air, which can be introduced through a rectum tube. At this point, a conventional CT scan is performed to acquire data from the region of the colon (step 1520). For example, data can be acquired using a GE/CTI spiral mode scanner operating in a helical mode of 5 mm, 1.5–2.0:1 pitch, reconstructed in 1 mm slices, where the pitch is adjusted based upon the patient's height in a known manner. A routine imaging protocol of 120 kVp and 200–280 ma can be utilized for this operation. The data can be acquired and reconstructed as 1 mm thick slice images having an array size of 512×512 pixels in the field of view, which varies from 34 to 40 cm depending on the patient's size. the number of such slices generally varies under these conditions from 300 to 450, depending on the patient's height. The image data set is converted to volume elements or voxels (step 1530).

Image segmentation can be performed in a number of ways. In one present method of image segmentation, a local neighbor technique is used to classify voxels of the image data in accordance with similar intensity values. In this method, each voxel of an acquired image is evaluated with respect to a group of neighbor voxels. The voxel of interest is referred to as the central voxel and has an associated intensity value. A classification indicator for each voxel is established by comparing the value of the central voxel to each of its neighbors. If the neighbor has the same value as the central voxel, the value of the classification indicator is incremented. However, if the neighbor has a different value from the central voxel, the classification indicator for the central voxel is decremented. The central voxel is then classified to that category which has the maximum indicator value, which indicates the most uniform neighborhood among the local neighbors. Each classification is indicative of a particular intensity range, which in turn is representative of one or more material types being imaged. The method can be further enhanced by employing a mixture probability function to the similarity classifications derived.

Figure 16:
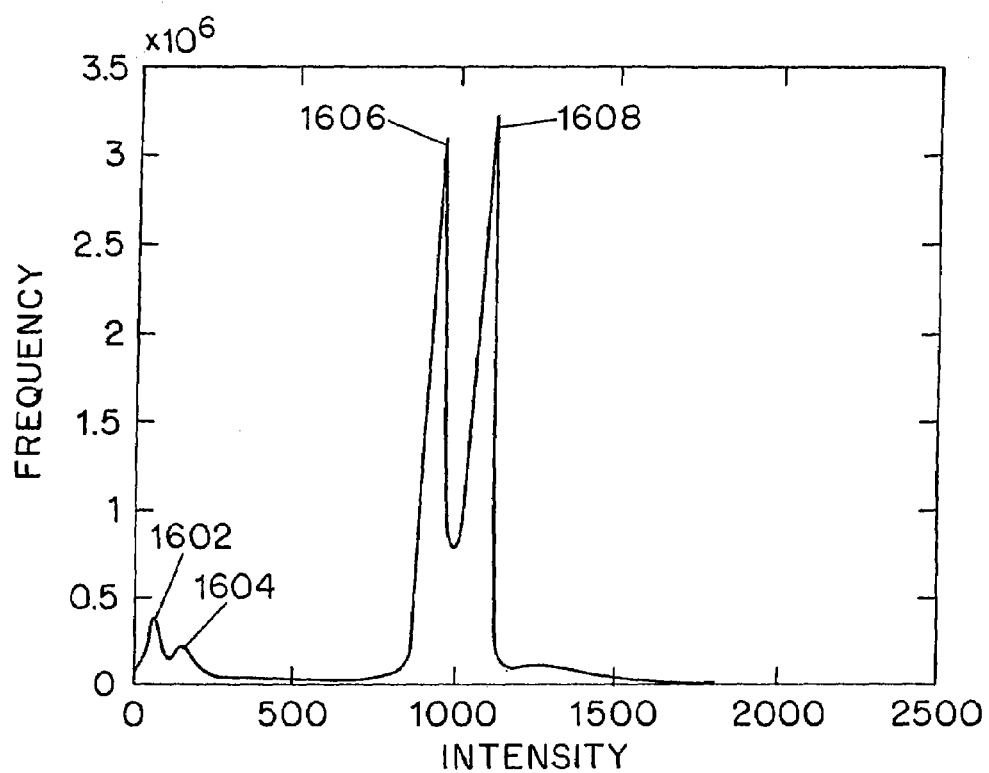
FIG. 16 is a graph of voxel intensity versus frequency of a typical abdominal CT data set.

An alternate process of image segmentation is performed as two major operations: low level processing and high level feature extraction. During low level processing, regions outside the body contour are eliminated from further processing and voxels within the body contour are roughly categorized in accordance with well defined classes of intensity characteristics. For example, a CT scan of the abdominal region generates a data set which tends to exhibit a well defined intensity distribution. The graph of FIG. 16 illustrates such an intensity distribution as an exemplary histogram having four, well defined peaks, 1602, 1604, 1606, 1608, which can be classified according to intensity thresholds.

The voxels of the abdominal CT data set are roughly classified as four clusters by intensity thresholds (step 1540). For example, Cluster 1 can include voxels whose intensities are below 140. This cluster generally corresponds to the lowest density regions within the interior of the gas filled colon. Cluster 2 can include voxels which have intensity values in excess of 2200. These intensity values correspond to the enhanced stool and fluid within the colon as well as bone. Cluster 3 can include voxels with intensities in the range of about 900 to about 1080. This intensity range generally represents soft tissues, such as fat and muscle, which are unlikely to be associated with the colon. The remaining voxels can then be grouped together as cluster 4, which are likely to be associated with the colon wall (including mucosa and partial volume mixtures around the colon wall) as well as lung tissue and soft bones.

Clusters 1 and 3 are not particularly valuable in identifying the colon wall and, therefore are not subject to substantial processing during image segmentation procedures for virtual colonoscopy. The voxels associated with cluster 2 are important for segregating stool and fluid from the colon wall and are processed further during the high-level feature extraction operations. Low level processing is concentrated on the fourth cluster, which has the highest likelihood of corresponding to colon tissue (step 1550).

Figure 17:
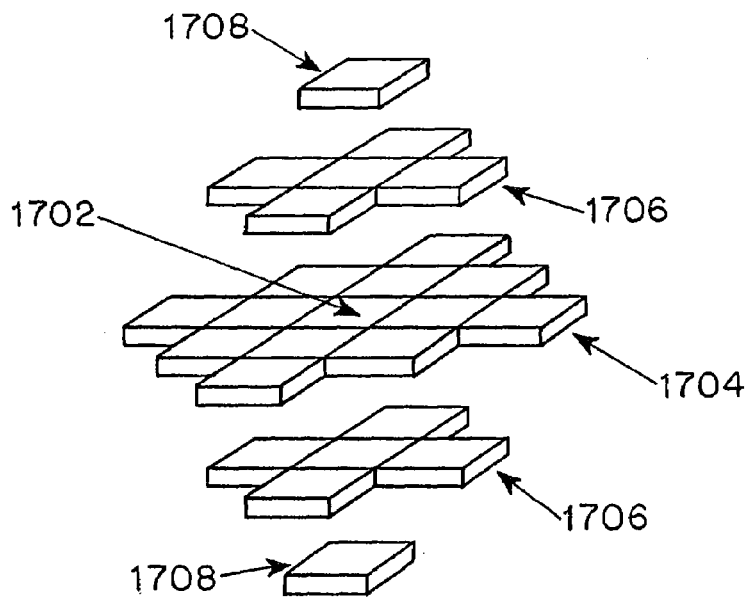
FIG. 17 is a perspective view diagram of an intensity vector structure including a voxel of interest and its selected neighbors.

For each voxel in the fourth cluster, an intensity vector is generated using itself and its neighbors. The intensity vector provides an indication of the change in intensity in the neighborhood proximate a given voxel. The number of neighbor voxels which are used to establish the intensity vector is not critical, but involves a tradeoff between processing overhead and accuracy. For example, a simple voxel intensity vector can be established with seven (7) voxels, which includes the voxel of interest, its front and back neighbors, its left and right neighbors and its top and bottom neighbors, all surrounding the voxel of interest on three mutually perpendicular axes. FIG. 17 is a perspective view illustrating an exemplary intensity vector in the form of a 25 voxel intensity vector model, which includes the selected voxel 1702 as well as its first, second and third order neighbors. The selected voxel 1702 is the central point of this model and is referred to as the fixed voxel. A planar slice of voxels, which includes 12 neighbors on the same plane as the fixed voxel, is referred to as the fixed slice 1704. On adjacent planes to the fixed slice are two nearest slices 1706, having five voxels each. Adjacent to the first nearest slices 1706 are two second nearest slices 1708, each having a single voxel. The collection of intensity vectors for each voxel in the fourth cluster is referred to as a local vector series.

Because the data set for an abdominal image generally includes more than 300 slice images, each with a 512×512 voxel array, and each voxel having an associated 25 voxel local vector, it is desirable to perform feature analysis (step 1570) on the local vector series to reduce the computational burden. One such feature analysis is a principal component analysis (PCA), which can be applied to the local vector series to determine the dimension of a feature vector series and an orthogonal transformation matrix for the voxels of cluster 4.

It has been found that the histogram (FIG. 16) of the CT image intensities tends to be fairly constant from patient to patient for a particular scanner, given equivalent preparation and scanning parameters. Relying on this observation, an orthogonal transformation matrix can be established which is a predetermined matrix determined by using several sets of training data acquired using the same scanner under similar conditions. From this data, a transformation matrix, such as a Karlhunen-Loéve (K-L) transformation, can be generated in a known manner. The transformation matrix is applied to the local vector series to generate feature vector series. Once in the feature-vector space domain, vector quantization techniques can be used to classify the feature vector series.

An analytical, self-adaptive algorithm can be used for the classification of the feature vectors. In defining this algorithm, let $\{X_i \in R^4 : i=1,2,3,\ldots,N\}$ be the series of the feature vectors, where N is the number of feature vectors; K denotes the maximum number of classes; and T is a threshold which is adaptive to the data set. For each class, a representative element is generated by the algorithm. Let $a_k$ be a representative element of class k and $n_k$ be the number of feature vectors in that class.

The algorithm can then be outlined as:
1. Set $n_1=1$; $a_1$; $\overline{K}=1$;
2. obtain the class number $\overline{K}$ and class parameters $(a_k, n_k)$

```
for (i=1; i<N; i++)
    for (j = 1; j<K̄; j++)
        calculate dⱼ = dist(Xᵢ,aⱼ);
    end for
    index=arc min dⱼ;
    if ((d_index < T)ʲ or (K̄ = K))
        update class parameters:

a_index = ─────────── × (n_index · a_index + Xᵢ);
                  n_index + 1 n_index = n_index+1;
    end if
    else
        generate new class
        a_{K̄+1} = Xᵢ;
        n_{K̄+1} = 1;
        K̄ = K̄+1;
    end else
end for
```

3. label each feature vector to a class according to the nearest neighbor rule

```
for (i = 1; i < N; i++)
    for (j = 1; j < K̄; j++)
        calculate dⱼ = dist (Xᵢ, aⱼ) ;
    end for
    index = arc min d_J,
    label voxel i to class index.
end for
```

In this algorithm, dist(x,y) is the Euclidean distance between vector x and y and arc min $d_j$ gives the integer j which realizes the minimum value of $d_j$.

The above described algorithm is dependent only on the parameters T and K. However, the value of K, which relates to the number of classes within each voxel cluster, is not critical and can be set to a constant value, such as K=18. However, T, which is the vector similarity threshold, greatly influences the classification results. If the selected value of T is too large, only a single class will be generated. On the other hand, if the value of T is too small, the resulting classes will exhibit undesirable redundancy. By setting the value of T to be equal to the maximum component variance of the feature vector series, the maximum number of distinct classes results.

As a result of the initial classification process, each voxel within the selected cluster is assigned to a class (step 1570). In the exemplary case of virtual colonoscopy, there are several classes within cluster 4. Thus, the next task is to determine which of the several classes in cluster 4 corresponds to the colon wall. The first coordinate of the feature vector, which is that coordinate of the feature vector exhibiting the highest variance, reflects the information of the average of the 3D local voxel intensities. The remaining coordinates of the feature vector contain the information of directional intensity change within the local neighbors. Because the colon wall voxels for the interior of the colon are generally in close proximity to the gas voxels of cluster 1, a threshold interval can be determined by data samples selected from typical colon wall intensities of a typical CT data set to roughly distinguish colon wall voxel candidates. The particular threshold value is selected for each particular imaging protocol and device. This threshold interval can then applied to all CT data sets (acquired from the same machine, using the same imaging protocol). If the first coordinate of the representative element is located in the threshold interval, the corresponding class is regarded as the colon wall class and all voxels in that class are labeled as colon wall-like voxels.

Each colon wall-like voxel is a candidate to be a colon wall voxel. There are three possible outcomes of not belonging to the colon wall. The first case relates to voxels which are close to the stool/liquid inside the colon. The second case occurs when voxels are in the lung tissue regions. The third case represents mucosa voxels. Clearly then, low level classification carries a degree of classification uncertainty. The causes of the low-level classification uncertainty vary. For example, a partial-volume effect resulting from voxels containing more than one material type (i.e., fluid and colon wall) leads to the first case of uncertainty. The second and the third cases of uncertainty are due to both the partial volume effect as well as the low contrast of CT images. To resolve the uncertainty, additional information is needed. Thus, a high-level feature extraction procedure is used in the present method to further distinguish candidates for the colon wall from other colon wall-like voxels, based on a priori anatomical knowledge of the CT images (step 1580).

Figure 18A:
FIG. 18A is an exemplary image slice from a CT scan of a human abdominal region, primarily illustrating a region including the lungs.
Figure 18B:
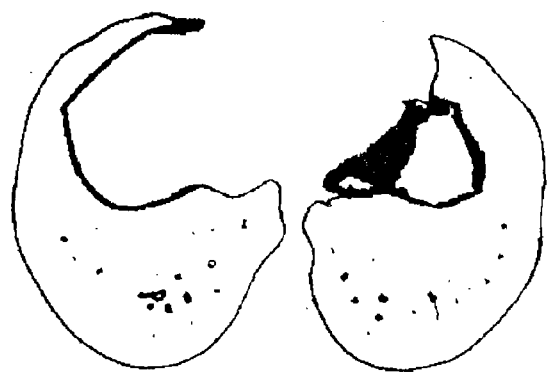
FIG. 18B is a pictorial diagram illustrating the identification of the lung region in the image slice of FIG. 18A.
Figure 18C:
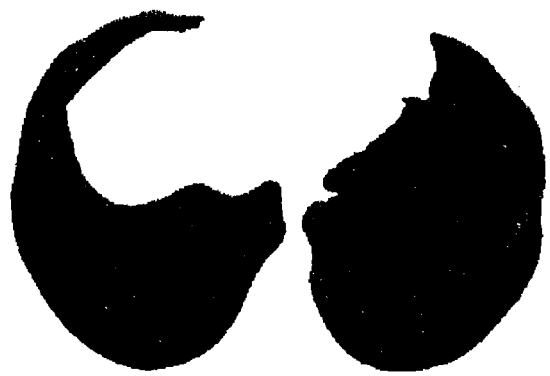
FIG. 18C is a pictorial diagram illustrating the removal of the lung volume identified in FIG. 18B.

An initial step of the high-level feature extraction procedure can be to eliminate the region of lung tissue from the low-level classification results. FIG. 18A is an exemplary slice image clearly illustrating the lung region 1802. The lung region 1802 is identifiable as a generally contiguous three dimensional volume enclosed by colon wall-like voxels, as illustrated in FIG. 18B. Given this characteristic, the lung region can be identified using a region growing strategy. The first step in this technique is to find a seed voxel within the region of growing. Preferably, the operator performing the CT imaging scan sets the imaging range such that the top most slice of the CT scan does not contain any colon voxels. As the interior of lung should be filled with air, the seed is provided by the low-level classification simply by selecting an air voxel. Once the lung region outline of FIG. 18B is determined, the lung volume can be removed from the image slice (FIG. 18C).

Figure 19A:
FIG. 19A is a exemplary image slice form a CT scan of a human abdominal region, primarily illustrating a region including a portion of the colon and bone.
Figure 19B:
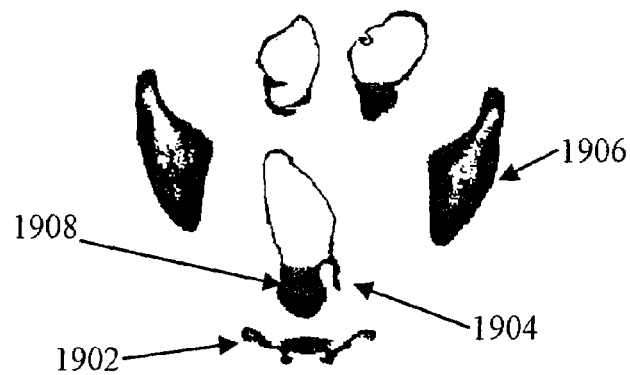
FIG. 19B is a pictorial diagram illustrating the identification of the colon and bone region from the image slice of FIG. 19A.
Figure 19C:
FIG. 19C is a pictorial diagram illustrating the image scan of FIG. 19a with the regions of bone removed.

A next step in performing high-level feature extraction can be to separate the bone voxels from enhanced stool/fluid voxels in cluster 2. The bone tissue voxels 1902 are generally relatively far away from the colon wall and resides outside the colon volume. To the contrary, the residual stool 1906 and fluid 1904 are enclosed inside the colon volume. Combining the a priori proximity information and the colon wall information obtained from the low-level classification process, a rough colon wall volume is generated. Any voxel separated by more than a predetermined number (e.g., 3) of voxel units from the colon wall, and outside the colon volume, will be labeled as bone and then removed from the image. The remaining voxels in cluster 2 can be assumed to represent stool and fluid within the colon volume (see FIGS. 19A–C).

The voxels within the colon volume identified as stool 1906 and fluid 1904 can be removed from the image to generate a clean colon lumen and colon wall image. In general, there are two kinds of stool/fluid regions. One region type is small residual areas of stool 1906 attached to the colon wall. The other region type is large volumes of fluid 1904, which collect in basin-like colonic folds (see FIGS. 19A–C).

The attached residual stool regions 1906 can be identified and removed because they are inside the rough colon volume generated during the low-level classification process. The fluid 1906 in the basin-like colon fold usually has a horizontal surface 1908 due to the effect of gravity. Above the surface is always a gas region, which exhibits a very high contrast to the fluid intensity. Thus, the surface interface of the fluid regions can be easily marked.

Using a region growing strategy, the contour of the attached stool regions 1906 can be outlined, and the part which is away from the colon wall volume can be removed. Similarly, the contour of the fluid regions 1904 can also be outlined. After eliminating the horizontal surfaces 1908, the colon wall contour is revealed and the clean colon wall is obtained.

It is difficult to distinguish the mucosa voxels from the colon wall voxels. Even though the above three dimensional processing can remove some mucosa voxels, it is difficult to remove all mucosa voxels. In optical colonoscopy, physicians directly inspect the colonic mucosa and search for lesions based on the color and texture of the mucosa. In virtual colonoscopy, most mucosa voxels on the colon wall can be left intact in order to preserve more information. This can be very useful for three dimensional volume rendering.

From the segmented colon wall volume, the inner surface, the outer surface and the wall itself of the colon can be extracted and viewed as a virtual object. This provides a distinct advantage over conventional optical colonoscopy in that the exterior wall of the colon can be examined as well as the interior wall. Furthermore, the colon wall and the colon lumen can be obtained separately from the segmentation.

Because the colon is substantially evacuated prior to imaging, a commonly encountered problem is that the colon lumen collapses in spots. While the inflation of the colon with compressed gas, such as air or $CO_2$, reduces the frequency of collapsed regions, such areas still occur. In performing a virtual colonoscopy, it is desirable to automatically maintain a flight path through the collapsed regions and it is also desirable to use the scanned image data to at least partially recreate the colon lumen in the collapsed regions. Since the above described image segmentation methods effectively derive both the interior and exterior of the colon wall, this information can be used to enhance the generation of the fly path through the collapsed regions.

In extending the flight path through collapsed regions of the colon or expanding a collapsed region of the colon, the first step is to detect a collapsed region. Using the premise that the grayscale values of the image data from around the outside of the colon wall change much more dramatically than the greyscale values within the colon wall itself, as well as in other regions such as fat, muscle and other kinds of tissue, an entropy analysis can be used to detect areas of colon collapse.

The degree of change in greyscale value, for example along the centerline, can be expressed and measured by an entropy value. To calculate an entropy value, voxels on the outer surface of the colon wall are selected. Such points are identified from the above described image segmentation techniques. A 5×5×5 cubic window can be applied to the pixels, centered on the pixel of interest. Prior to calculating the entropy value, a smaller (3×3×3) window can be applied to the pixels of interest in order to filter out noise from the image data. The entropy value of a selected window about the pixel can then be determined by the equation:

$$E = \sum_1 C(i)\ln(C(i))$$

where E is the entropy and C(i) is the number of points in the window with the grayscale of i (i=0,1,2, . . . , 255). The calculated entropy values for each window are then compared against a predetermined threshold value. For regions of air, the entropy values will be fairly low, when compared to regions of tissue. Therefore, along the centerline of the colon lumen, when the entropy values increase and exceed the predetermined threshold value, a collapsed region is indicated. The exact value of the threshold is not critical and will depend in part on the imaging protocol and particulars of the imaging device.

Once a collapsed region is detected, the previously determined centerline flight path can be extended through the region by piercing through the center of the collapse with a one voxel wide navigation line.

In addition to automatically continuing the flight path of the virtual camera through the colon lumen, the region of colon collapse can be virtually opened using a physical modeling technique to recover some of the properties of the collapsed region. In this technique, a model of the physical properties of the colon wall is developed. From this model, parameters of motion, mass density, damping density, stretching and bending coefficients are estimated for a Lagrange equation. Then, an expanding force model (i.e., gas or fluid, such as air, pumped into the colon) is formulated and applied in accordance with the elastic properties of the colon, as defined by the Lagrange equation, such that the collapsed region of the colon image is restored to its natural shape.

To model the colon, a finite-element model can be applied to the collapsed or obstructed regions of the colon lumen. This can be performed by sampling the elements in a regular grid, such as an 8 voxel brick, and then applying traditional volume rendering techniques. Alternatively, an irregular volume representation approach, such as tetrahedrons can be applied to the collapsed regions.

In applying the external force (air pumping) model to the colon model, the magnitude of the external force is first determined to properly separate the collapsed colon wall regions. A three dimensional growing model can be used to trace the internal and external colon wall surfaces in a parallel manner. The respective surfaces are marked from a starting point at the collapsed region to a growing source point, and the force model is applied to expand the surfaces in a like and natural manner. The region between the internal and external surfaces, i.e., the colon wall, are classified as sharing regions. The external repulsive force model is applied to these sharing regions to separate and expand the collapsed colon wall segments in a natural manner.

To more clearly visualize the features of a virtual object, such as the colon, which is subjected to virtual examination, it is advantageous to provide a rendering of the various textures of the object. Such textures, which can be observed in the color images presented during optical colonoscopy, are often lost in the black and white, grey scale images provided by the CT image data. Thus a system and method for texture imaging during virtual examination is required.

Figure 20:
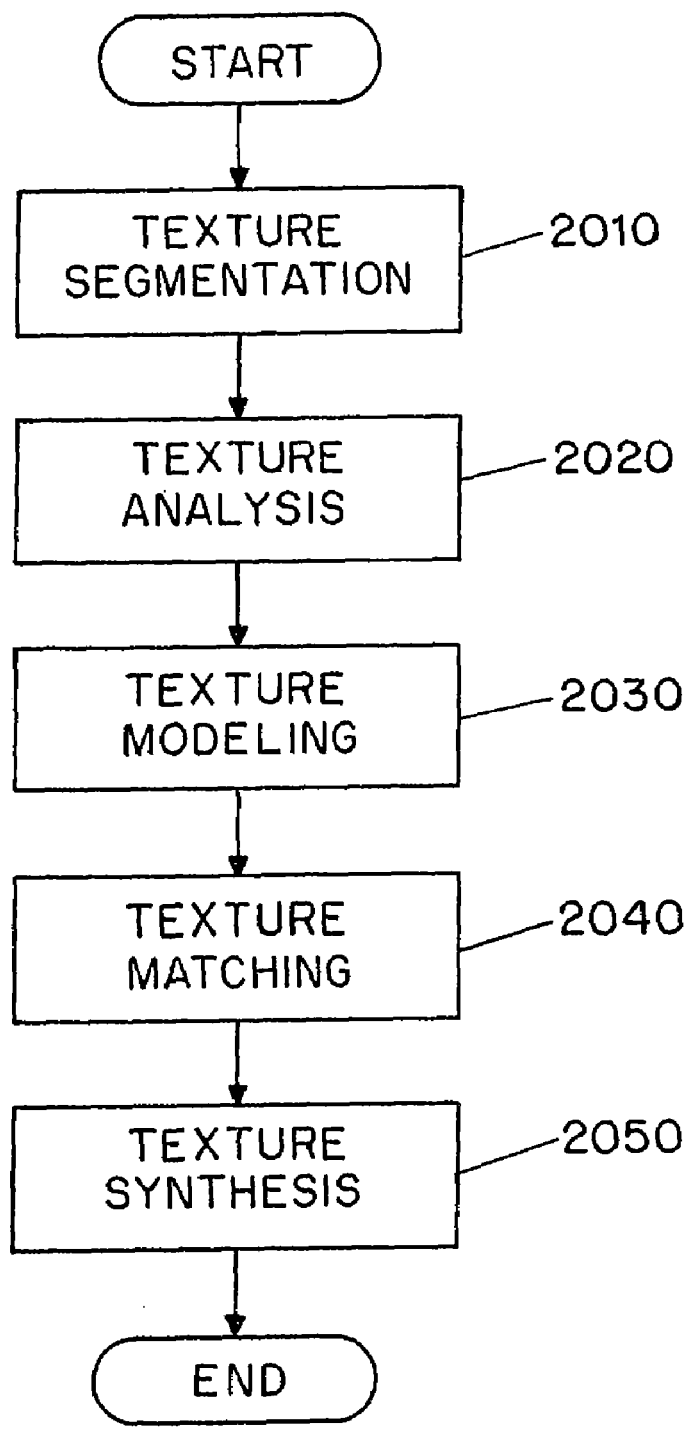
FIG. 20 is a flowchart illustrating a method for applying texture to monochrome image data.

FIG. 20 is a flow chart depicting a present method for generating virtual objects having a texture component. The purpose of this method is to map textures obtained by optical colonoscopy images in the red-green-blue (RGB) color space, as for example from the Visible Human, onto the gray scale monochrome CT image data used to generate virtual objects. The optical colonoscopy images are acquired by conventional digital image acquisition techniques, such as by a digital "frame grabber" 1429 which receives analog optical images from a camera, such as a video camera, and converts the image to digital data which can be provided to CPU 1423 via interface port 1431 (FIG. 14). The first step in this process is to segment the CT image data (step 2010). The above described image segmentation techniques can be applied to choose intensity thresholds in the grey scale image to classify the CT image data into various tissue types, such as bone, colon wall tissue, air, and the like.

In addition to performing image segmentation on the CT image data, the texture features of the optical image need to be extracted from the optical image data (step 2020). To do this, a gausian filter can be applied to the optical image data followed by sub-sampling to decompose the data into a multiresolutional pyramid. A laplacian filter and steerable filter can also be applied to the multiresolutional pyramid to obtain oriented and non-oriented features of the data. While this method is effective at extracting and capturing the texture features, the implementation of this approach requires a large amount of memory and processing power.

An alternative approach to extracting the texture features from the optical image is to utilize a wavelet transform. However, while wavelet transformations are generally computationally efficient, conventional wavelet transforms are limited in that they only capture features with orientations parallel to the axes and cannot be applied directly to a region of interest. To overcome these limitations, a non-separable filter can be employed. For example, a lifting scheme can be employed to build filter banks for wavelets transform in any dimension using a two step, prediction and updating approach. Such filter banks can be synthesized by the Boor-Rom algorithm for multidimensional polynomial interpolation.

After the textural features are extracted from the optical image data, models must be generated to describe these features (step 2030). This can be performed, for example, by using a non-parametric multi-scale statistical model which is based on estimating and manipulating the entropy of non-Gaussian distributions attributable to the natural textures.

Once texture models are generated from the optical image data, texture matching must be performed to correlate these models to the segmented CT image data (step 2050). In regions of the CT image data where the texture is continuous, corresponding classes of texture are easily matched. However, in boundary regions between two or more texture regions, the process is more complex. Segmentation of the CT data around a boundary region often leads to data which is fuzzy, i.e., the results reflect a percentage of texture from each material or tissue and vary depending on the various weighting of each. The weighting percentage can be used to set the importance of matching criteria.

In the case of the non-parametric multi-scale statistical model, the cross entropy or a Kullback-Leiber divergence algorithm can be used to measure the distribution of different textures in a boundary region.

After texture matching, texture synthesis is performed on the CT image data (step 2050). This is done by fusing the textures from the optical image data in to the CT image data. For isotropic texture patterns, such as presented by bone, the texture can be sampled directly from the optical data to the segmented CT image data. For anisotropic texture regions, such as colon mucosa, a multiresolution sampling procedure is preferred. In this process, selective re-sampling for homogenous and heterogenous regions is employed.

Alternatively, pseudocolor texture can be created directly from the CT data. For each voxel, multiple CT values, comprising a local area neighborhood, can be evaluated to determine a pseudocolor for the given voxel. For each voxel the local neighborhood consists of the voxels that are within some given distance of the center voxel. For example a 5×5×5 voxel cubic shaped region, or the double pyramid which represents all voxels within 3 units measured by Manhattan distance. This vector of scalar values is then evaluated to map to a color to be displayed for this voxel during subsequent volume rendering. The evaluation of the local neighborhood vector of values can compute such things as local curvature, homo/heterogeneity, or other geometric or spatial functions.

Volume Rendering

Figure 21:
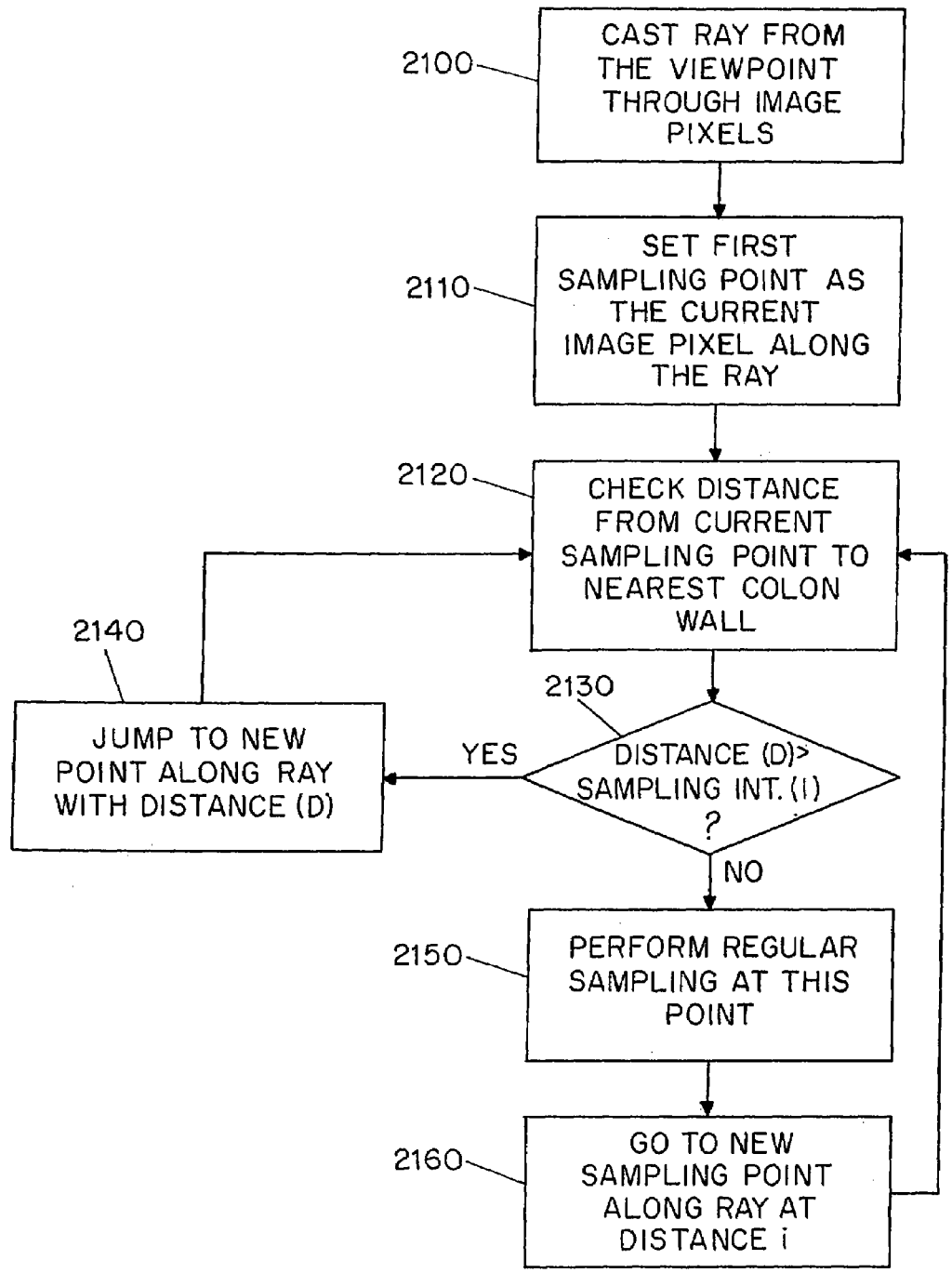
FIG. 21 is a flowchart illustrating a method for volume rendering employing a fast perspective ray casting technique.
Figure 22:
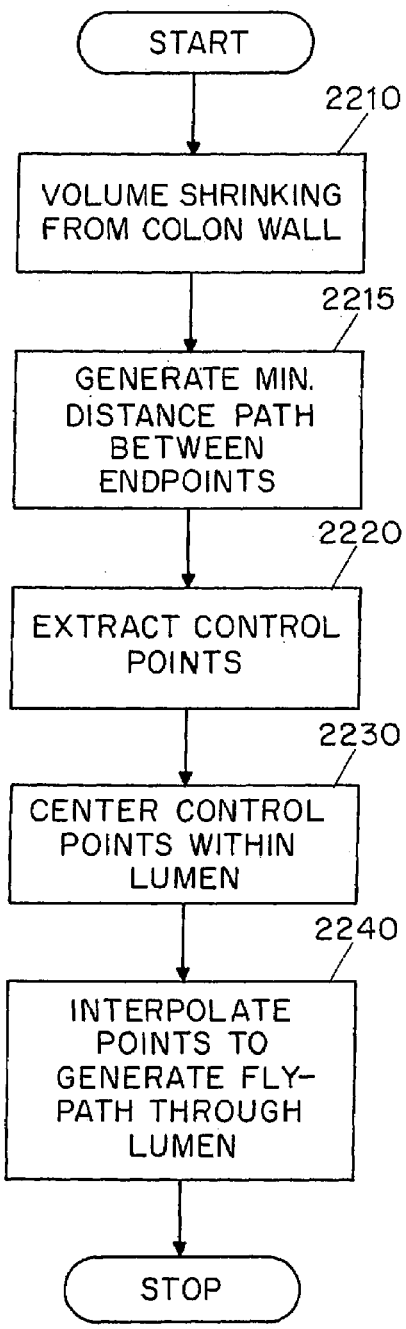
FIG. 22 is a flowchart illustrating a method for determining the central flight path through a colon lumen employing a volume shrinking technique.

In addition to image segmentation and texture mapping described above, volume rendering techniques can be used in connection with virtual colonoscopy procedures to further enhance the fidelity of the resulting image. FIG. 21 illustrates a perspective volume ray-casting method which can be used for volume rendering in accordance with the present invention. From a selected virtual viewpoint, e.g., camera position, such as within the colon lumen, rays are cast through each of the proximate image pixels (step 2100). For each ray, the first sampling point is set as the current image pixel along the ray (step 2110). The distance (d) between the current sampling point and the nearest colon wall is then determined (step 2120). The current distance (d) is compared to a predetermined sampling interval (i) (step 2130). If the distance (d) is greater than the sampling interval (i) then no sampling occurs and the next sampling point along the ray is determined by jumping the distance d along the ray (step 2140). If the distance is less than or equal to the sampling interval (i) then conventional sampling is performed on this point (step 2150) and the next sampling point is selected in accordance with the sampling interval (i) (step 2160). For example, trilinear interpolation between the density values of 8 neighboring voxels can be performed to determine the new density value at the sampling point.

The method of FIG. 21 effectively accelerates ray-casting because a space leaping technique is used to quickly skip over empty space along the ray of the image plane to the colon wall. In this method, a distance from a sample point to the nearest colon wall is determined along each ray. If the distance is larger than a predetermined sampling interval (i), a jump to the next sampling point along the ray is performed. Since the closest distance information is already available from the potential field which is used for virtual camera control, no additional distance coding calculations are required. In this case, neither surface rendering nor Z-buffer transform is required, which results in savings in preprocessing time and memory space.

Alternatively, a space leaping method can derive distance information for each ray from the Z-buffer of the corresponding surface rendering image. If the surface rendering image and volume rendering image will both be generated, this approach provides minimal processing overhead burden as the Z-buffer information is provided as a result of the surface rendering methods. Thus, this form of space leaping method only requires additional processing to perform a depth transformation from the image space domain to the world space domain.

For those regions along the ray where the distance (d) was traversed in step 2140, the region along the ray corresponds to open space and can be assigned a value according to an open space transfer function. Typically, open space will have no contribution on the final pixel value. For each point where sampling takes place, one or more defined transfer functions can be assigned to map different ranges of sample values of the original volume data to different colors and opacities and possibly other displayable parameters. For example, four independent transfer functions have been used to determine different material by mapping ranges of CT density values into specified colors of red, green, blue and opacity, each in the range of 0 to 255.

Virtual Biopsy

The above described techniques can also form the basis of a system for performing virtual electronic biopsy of a region being examined to effect a flexible and non-invasive biopsy. As noted above, volume rendering techniques use one or more defined transfer functions to map different ranges of sample values of the original volume data to different colors, opacities and other displayable parameters for navigation and viewing. During navigation, the selected transfer function generally assigns maximum opacity to the colon wall such that the outer surface is easily viewed. Once a suspicious area is detected during virtual examination, the physician can interactively change the transfer function assigned during the volume rendering procedure such that the outer surface being viewed becomes substantially transparent, allowing the region information to be composited and thus the interior structure of the region to be viewed. Using a number of predetermined transfer functions, the suspicious area can be viewed at a number of different depths, with varying degrees of opacity assigned throughout the process.

Polyp Detection

The present system and methods can be used to perform automated polyp detection. With reference to FIG. 13, polyps 1305, which occur, for example, within the colon, generally take the form of small convex hill-like structures extending from the colon wall 1301. This geometry is distinct from the fold of the colon wall. Thus, a differential geometry model can be used to detect such polyps on the colon wall.

The surface of the colon lumen can be represented as a continuously second differentiable surface in three dimensional Euclidean space, such as by using a C-2 smoothness surface model. Such a model is described in "Modem Geometry Methods and Applications" by B. A. Dubrovin et al, published by Springer-Verlag 1994, which is hereby incorporated by reference in its entirety. In this model, each voxel on the surface of the colon has an associated geometrical feature which has a Gauss curvature, referred to as Gauss curvature fields. A convex hill on the surface, which may be indicative of a polyp, possesses a unique local feature in the Gauss curvature fields. Accordingly, by searching the Gauss curvature fields for specific local features, polyps can be detected. Once detected, the suspected polyps can be highlighted and thus brought to the attention of the physician where the physician can measure the suspected polyp and use the above described virtual biopsy methods to further investigate the suspicious region.

Central Fly-Path Generation

In the case of virtual colonoscopy, determining a proper navigation line, or fly-path, through the colon lumen is an important aspect of the described systems and methods. While certain techniques for determining the fly-path of the virtual camera model were discussed with respect to FIGS. 4–8, FIG. 22 illustrates an alternate method of generating the central fly-path through the colon lumen. After the colon wall is identified, such as by the image segmentation methods described herein, a volume shrinking algorithm can be employed to emphasize the trend of the colon lumen and reduce subsequent searching time within the lumen volume (step 2310).

Figure 23:
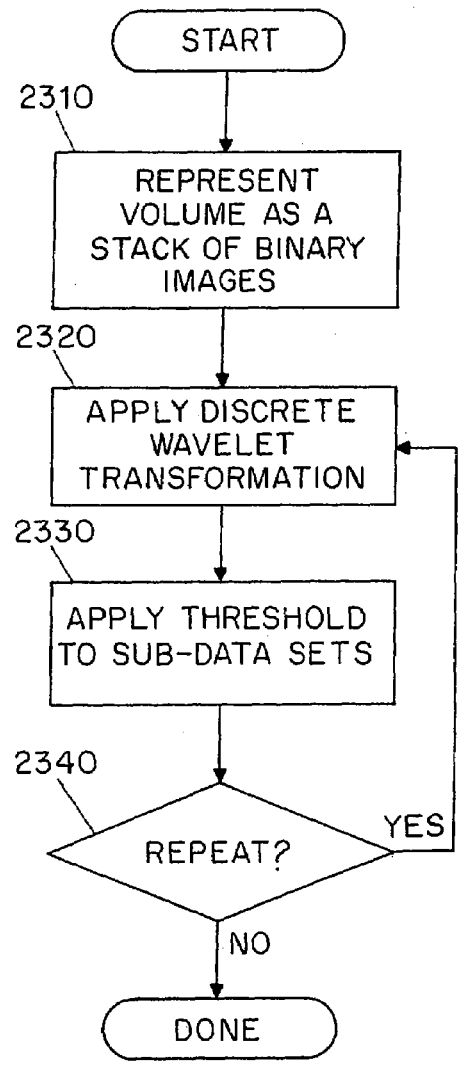
FIG. 23 is a flowchart further illustrating a volume shrinking technique for use in the method illustrated in FIG. 22.

FIG. 23 further illustrates the steps of an exemplary volume shrinking algorithm, which is based on a multiresolution analysis model. In this procedure, the three dimensional volume is represented by a stack of binary images which have the same matrix size (step 2310). Collectively, these images form a binary data set. A discrete wavelet transformation can be applied to the binary data set which results in a number of sub-data sets representing different time-frequency components of the binary data set (step 2320). For example, the discrete wavelet transformation may yield eight (8) sub-data sets. The sub-data sets are compared against predetermined threshold values such that the lowest frequency component is identified (step 2330). This component forms the binary data set for subsequent discrete wavelet transformation and thresholding steps, which are recursively applied in a multi-resolution structure (step 2340). In the case of virtual colonoscopy, the discrete wavelet transformation and associated thresholding can be applied three times recursively on the subsequent sub-dataset that represents the lowest frequency component (a 3-level multi-resolution decomposition).

Returning to FIG. 22, from the reduced colon volume model, a distance map technique can be employed to generate a minimum distance path between the two ends of the colon, e.g., from the rectum to the cecum (step 2215). The resulting path preserves the global trend information of the colon lumen, but ignores the trends exhibited by local folds. Control points within the global colon can then be determined by mapping the minimum distance path back to the original data space (Step 2220). For example, in the case of a 3-level multi-resolution decomposition, the reduced volume is three times smaller than the original volume and an affine transformation, which is well known, can be used to map the reduced volume model exactly back to the original scale volume. The minimum distance path of the reduced value can also be mapped back into the original scale volume as a series of points, which can be used as the control points within the colon.

The preferred fly path is one which is on the centerline of the colon lumen. However, the initial control points may not be exactly located in the center of the colon lumen. Thus, the initial control points can be centered, such as by the use of a bi-section plane algorithm (step 2230). For example, at each selected control point, a bi-section plane can be defined as a plane normal to the trend direction and cutting across the colon lumen. A centralization algorithm, such as a maximum disk algorithm, can then be performed on each bi-section plane. Such an algorithm is discussed in the article "On the Generation of Skeletons from Discrete Euclidean Distance Maps" by Ge et al., IEEE Transactions on PAMI, Vol. 18, pp. 1055–1066, 1996 which is hereby incorporated by reference.

Once the control points are centralized, the flight path can be determined by interpolating a line connecting these points (step 2240). In the case of virtual colonoscopy, it is desirable that the interpolated flight path take the form of a smooth curve which is substantially centered within the colon lumen. A constrained cubic B-spline interpolation algorithm based on Serret-Frenet Theorem in differential geometry theory can be used to establish a suitable smooth curved flight path, such as is described in "Numerical Recipes in C: The Art of Scientific Computing," by Press et al., Second Edition, Cambridge University Press, 1992.

Figure 24:
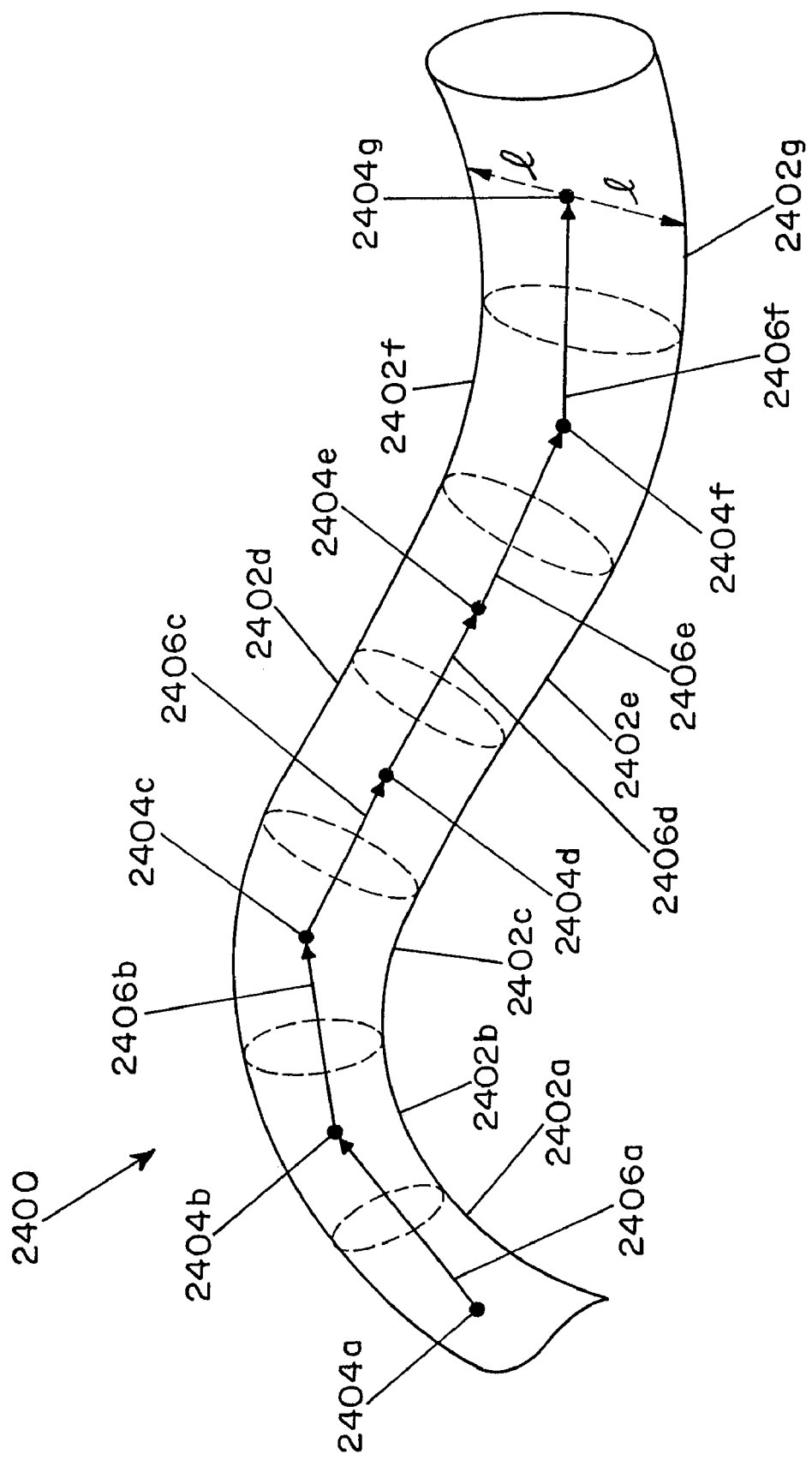
FIG. 24 is a three dimensional pictorial representation of a segmented colon lumen with a central fly-path generated therein.
Figures 25, 27:
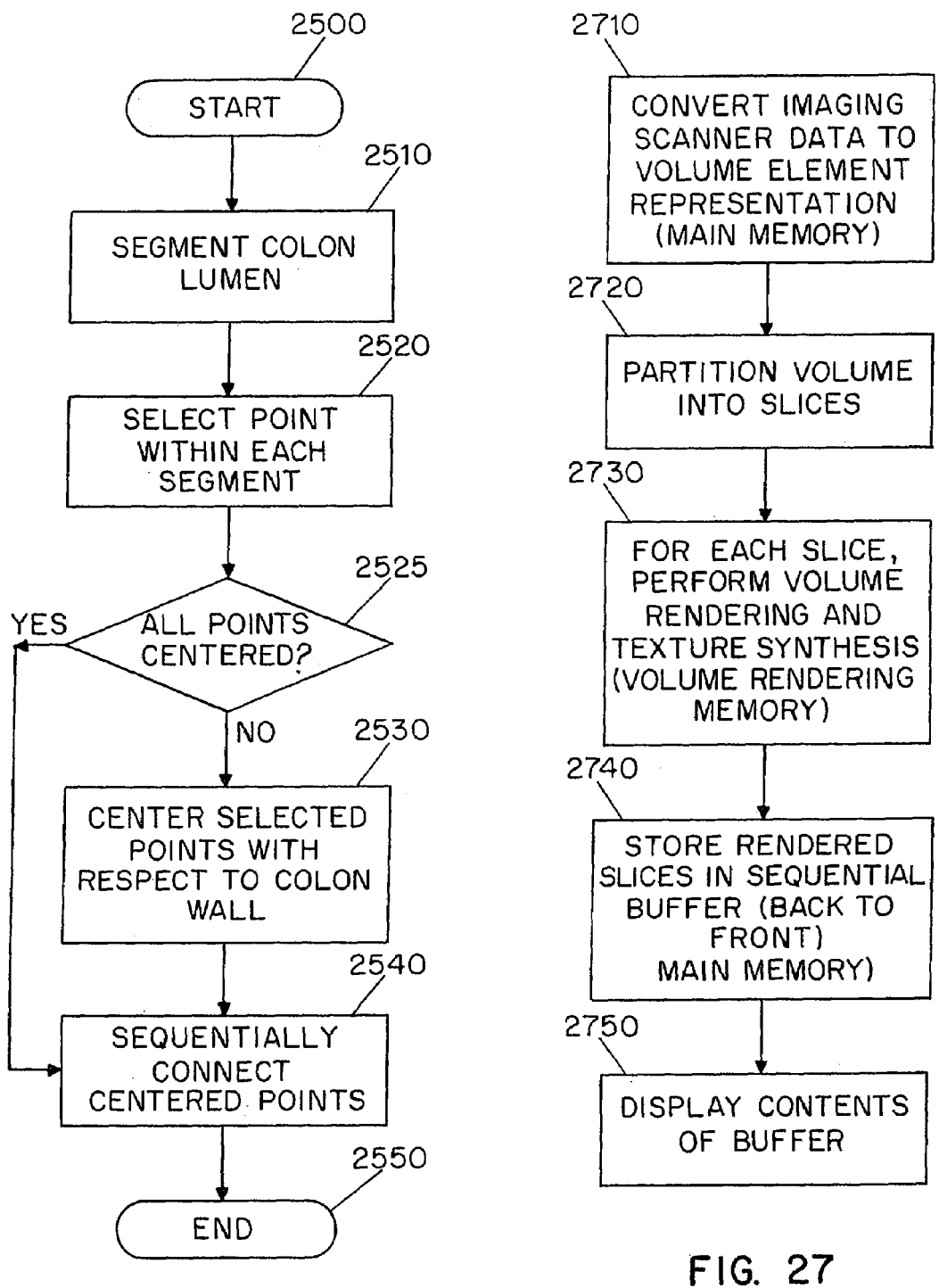
FIG. 25 is a flow chart illustrating a method of generating a central flight path through a colon lumen employing a segmentation technique.
FIG. 27 is a flow chart illustrating a method of performing volume imaging using the system of FIG. 26.

The pictorial representation of a segmented colon lumen in FIGS. 24 and the flow chart of FIG. 25 set forth yet another alternate fly-path generation method in accordance with the present invention. In this alternate method, the representation of the colon lumen 2400 is first partitioned into a number of segments 2402 a–g along the length of the lumen 2400 (step 2500). From within each segment 2402 a representative point is selected 2404 a–g (step 2520). Each representative point 2404 a–g is then centered with respect to the colon wall (step 2530), such as by the use of a physically-based deformable model which is used to push the points to the center of the respective segment. After the representative points are centered, the points are sequentially joined to establish the center-line fly-path for the virtual camera model (step 2540). If the segments are sufficiently small in length, the centered points can be connected with straight line segments 2406 a–f. However, when linear curve fitting techniques are applied to join the centered points, a smoother, continuous flight path is established.

Each of the foregoing methods can be implemented using a system as illustrated in FIG. 14, with appropriate software being provided to control the operation of CPU 1409 and CPU 1423.

Figure 26:
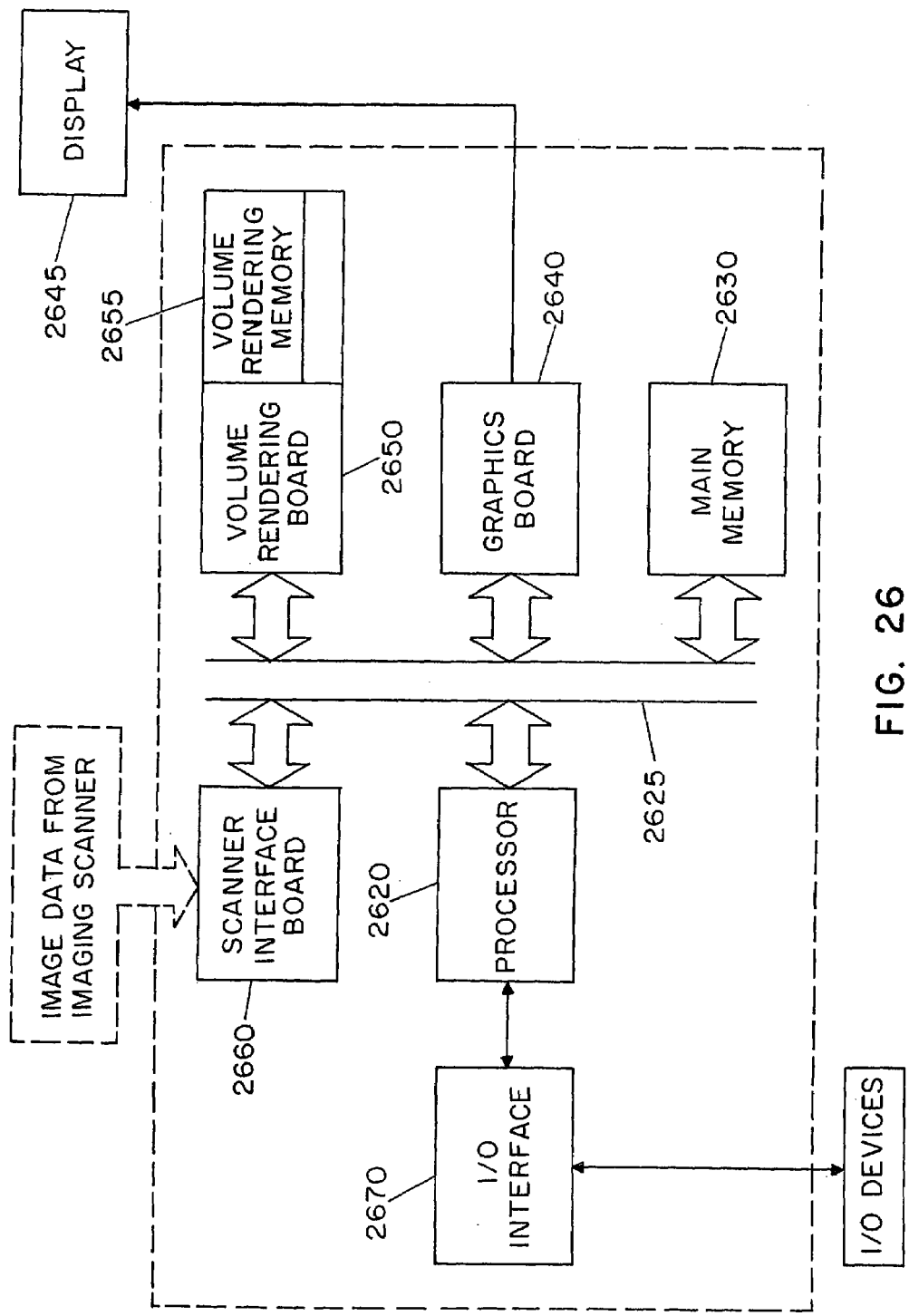
FIG. 26 is a block diagram of a system embodiment based on a personal computer bus architecture.

An alternate hardware embodiment, suitable for deployment on a personal computer, is illustrated in FIG. 26. The system includes a processor 2600 which should take the form of a high speed, multitasking processor such as a Pentium III processor operating at a clock speed in excess of 400 MHZ. The processor 2600 is coupled to a conventional bus structure 2620 which provides for high speed parallel data transfer. Also coupled to the bus structure 2620 are main memory 2630, a graphics board 2640, and a volume rendering board 2650. The graphics board 2640 is preferably one which can perform texture mapping, such as the Diamond Viper v770 Ultra manufactured by Diamond Multimedia Systems. The volume rendering board 2650 can take the form of the VolumePro board from Mitsubishi Electric, which is based on U.S. Pat. Nos. 5,760,781 and 5,847,711, which are hereby incorporated by reference. A display device 2645, such as a conventional SVGA or RGB monitor, is operatively coupled to the graphics board 2640 for displaying the image data. A scanner interface board 2660 is also provided for receiving data from an imaging scanner, such as an MRI or CT scanner, and transmitting such data to the bus structure 2620. The scanner interface board 2660 may be an application specific interface product for a selected imaging scanner or can take the form of a general purpose input/output card. The PC based system 2600 will generally include an I/O interface 2670 for coupling I/O devices 2680, such as a keyboard, digital pointer (e.g., mouse) and the like to the processor 2620. Alternatively, the I/O interface can be coupled to the processor 2620 via the bus 2620.

In the case of three dimensional imaging, including texture synthesis and volume rendering, numerous data handling and processing operations are required. For large datasets, such as those represented by the colon lumen and its surrounding area, such processing can be very time consuming and memory intense. However, using the topology of FIG. 26 in accordance with the processing method illustrated in the flow chart of FIG. 27, such operations can be performed on a relatively low cost personal computer (PC). Imaging data is received by the processor 2620 and stored in main memory 2630 via the scanner interface board 2660 and bus structure 2620. This image data (pixels) is converted into a volume element (voxel) representation (step 2710). The volume representation, which is stored in main memory 2630, is partitioned, for example into slices, such as along a major volume axis or other portions of the region being imaged (step 2720). The volume partitions are then transferred to the volume rendering board and temporarily stored in volume rendering memory 2655 for volume rendering operations (step 2730). The use of locally resident volume rendering memory 2655 provides for enhanced speed in volume rendering as data need not be exchanged over the bus 2620 during rendering of each slice of the total volume. Once volume rendering is complete for the slice, the rendered data is transferred back to main memory 2630 or the graphics board 2640 in a sequential buffer (step 2740). After all slices of interest have been subjected to rendering, the contents of the sequential buffer are processed by the graphics board 2640 for display on the display unit 2645 (step 2750).

Multi-scan Based Virtual Examination

The techniques discussed above generally perform virtual imaging based on a dataset acquired from a single magnetic resonance imaging (MRI) or computed tomography (CT) scan. However, the techniques discussed above are also useful for performing virtual examination of a region using multiple scans of a region. By using multiple scans of a region, improved imaging of regions of pathology can be achieved and motion artifacts can be reduced. One such application of interest is in performing virtual cystoscopy to screen a patient for possible polyps or cancer of the bladder.

Figure 28:
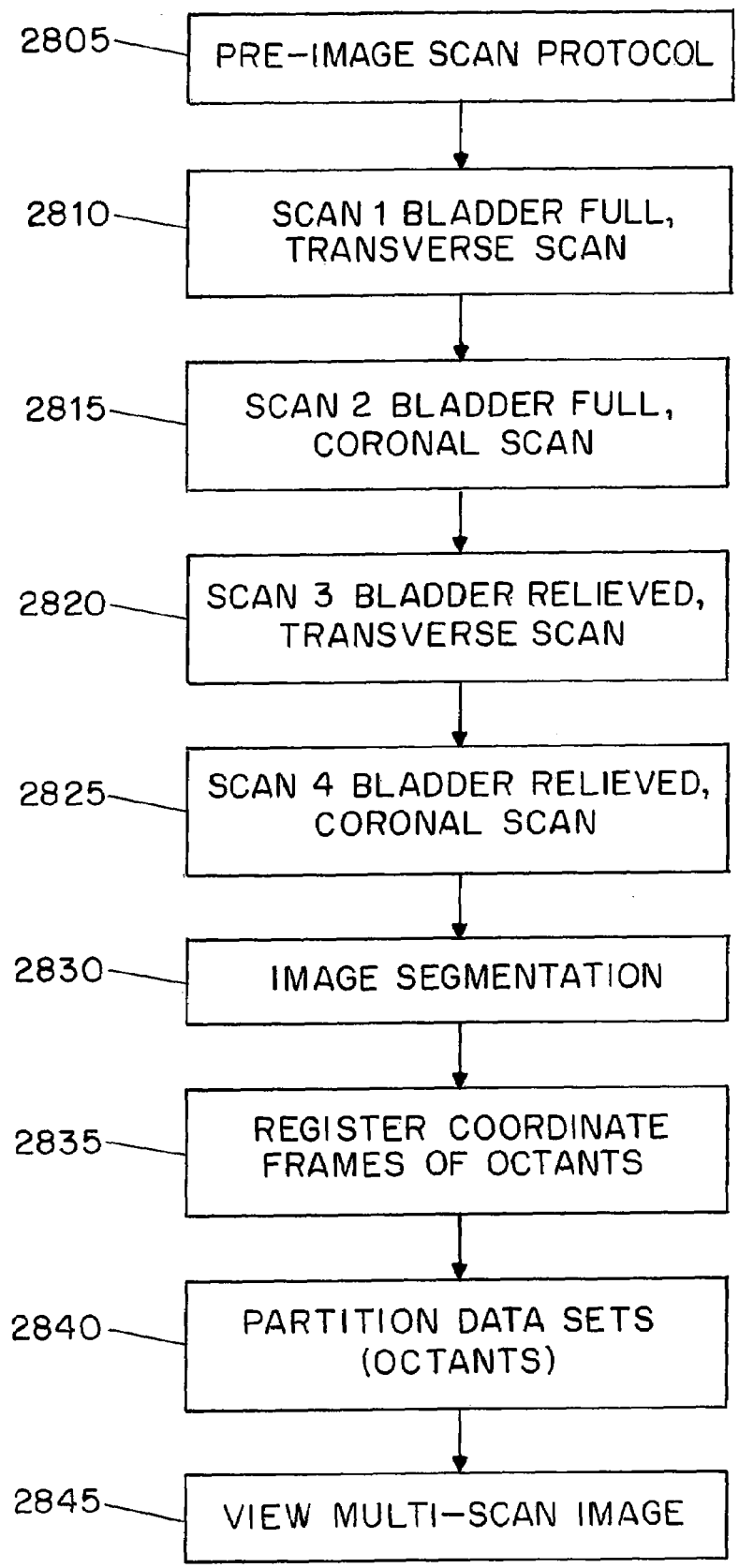
FIG. 28 is a flow chart illustrating a multi-scan method for performing virtual examination of an object, such as a bladder (virtual cystoscopy).

FIG. 28 is a flow chart which illustrates a method of employing multiple MRI scans to perform virtual examination of an object, such as virtual cystoscopy. Unlike CT images, where the bladder wall can be difficult to distinguish from urine, in MRI images, urine can be used as a natural contrast agent to delineate the inner bladder wall. To this end, a pre-image scan protocol is employed (step 2805). Approximately ½ hour prior to the first of four MRI scans, the patient is requested to empty the bladder and then consume one cup of water. After approximately ½ hour, the patient is subjected to the first of four MRI scans of the bladder region (step 2810). The first scan, with the bladder full and distended, follows protocol for T1-weighted transverse imaging. For example, when using the Picker scanner referenced above, a KJELL FASTER protocol using a 256× 256 matrix size, a 38 cm field of view (FOV), a 1.5 mm slice thickness (no gap), a 3 ms TE, a 9 ms TR, a 30 degree flip angle and one scan average can be used. Of course, these parameters tend to be scanner specific and various changes in the parameters can be used with acceptable results.

With the bladder still full, the patient is subjected to a second MRI scan, scan 2 (step 2815). The second scan follows a protocol for T1-weighted coronal imaging, such as the Picker KJELL FASTER protocol with a 256×256 matrix size, a 38 cm field of view (FOV), a 1.5 mm slice thickness (no gap), a 3 ms TE, a 9 ms TR, a 30 degree flip angle and a two-scan average.

The two image scans described above are taken along orthogonal axes with respect to one another. The advantage of this is that regions of significant motion artifacts in one scan, generally correspond to regions of minimal motion artifacts in the orthogonal scan. Accordingly, by taking a first scan in the transverse direction and a second scan in the coronal direction, the image scans can be registered and motion artifacts in the data set can be identified and compensated for.

After the scan 2, the patient is asked to relieve the bladder and is then subjected to two additional MRI scans. The third scan (step 2820) follows the same imaging protocol as the first scan (transverse imaging). The fourth scan (step 2825) follows the same imaging protocol as the second scan (coronal imaging).

The image scans can be acquired using a Picker 1.5 T Edge whole-body scanner. Although a T2 imaging protocol can be used, a T1 imaging protocol is preferred for virtual cystoscopy because this protocol provides improved delineation between fat and urine and offers a shorter acquisition period. Alternatively, the image scans can take the form of computed tomography or ultrasound imaging scans using suitable contrast agents and protocols for these imaging techniques.

During the first two scans (scan 1 and scan 2), the bladder is distended and the bladder wall is relatively thin. In this case, physiologically altered locations, such as tumors, may thin at a different rate as compared to the unaltered bladder wall and may become more apparent under these conditions. During the third and fourth scans, the bladder is substantially empty and the bladder wall is thicker. With a thicker wall, a more pronounced image contrast may result between normal tissue of the bladder wall and that of physiologically altered tissue.

After the four scans are acquired, the four corresponding datasets can then be individually processed. Initially, each scan data set is preferably subjected to image segmentation, as discussed above (step 2830), such as in connection with FIG. 15. During image segmentation, the voxels of the four datasets are classified into a number of categories, such as bladder wall, urine, fat, boundary, etc. The classification is based on the local intensity vectors of the voxels. Once the voxels are classified, the interior of the bladder lumen can be identified using a region growing algorithm beginning with a seed voxel selected from within the bladder volume, such as by selecting an air voxel or urine voxel.

Prior to clinical analysis of the segmented volume data sets, registration of the four data sets to a common coordinate system is performed (step 2835). Because the shape of the bladder varies from scan to scan, an exact voxel-voxel registration is not of practical value. Instead a flexible registration process is preferred. In the present flexible registration process, for each volume of interest (volume rendered for each corresponding scan) the center of the volume is determined, such as by averaging the three coordinates of all the voxels in the volume.

A Cartesian coordinate system can then be constructed with the origin of the system located at the center point of the volume. The axes of the system can then be oriented in a number of ways. A suitable selection of orientation corresponds to the orientation of the natural human body, e.g., with the Z-Axis running along the height of the body (e.g., from toe to head) the Y-axis oriented from back to front and the X-axis running laterally ( e.g., from left to right). The units of length in this coordinate system can be conveniently set to an arbitrary unit of one voxel length, the absolute magnitude of which will vary based on acquisition properties for the MRI scans. So long as the same pixel spacing is used in all scans to acquire all four data sets, this will result in a uniform value for each of the four data sets.

Figure 29:
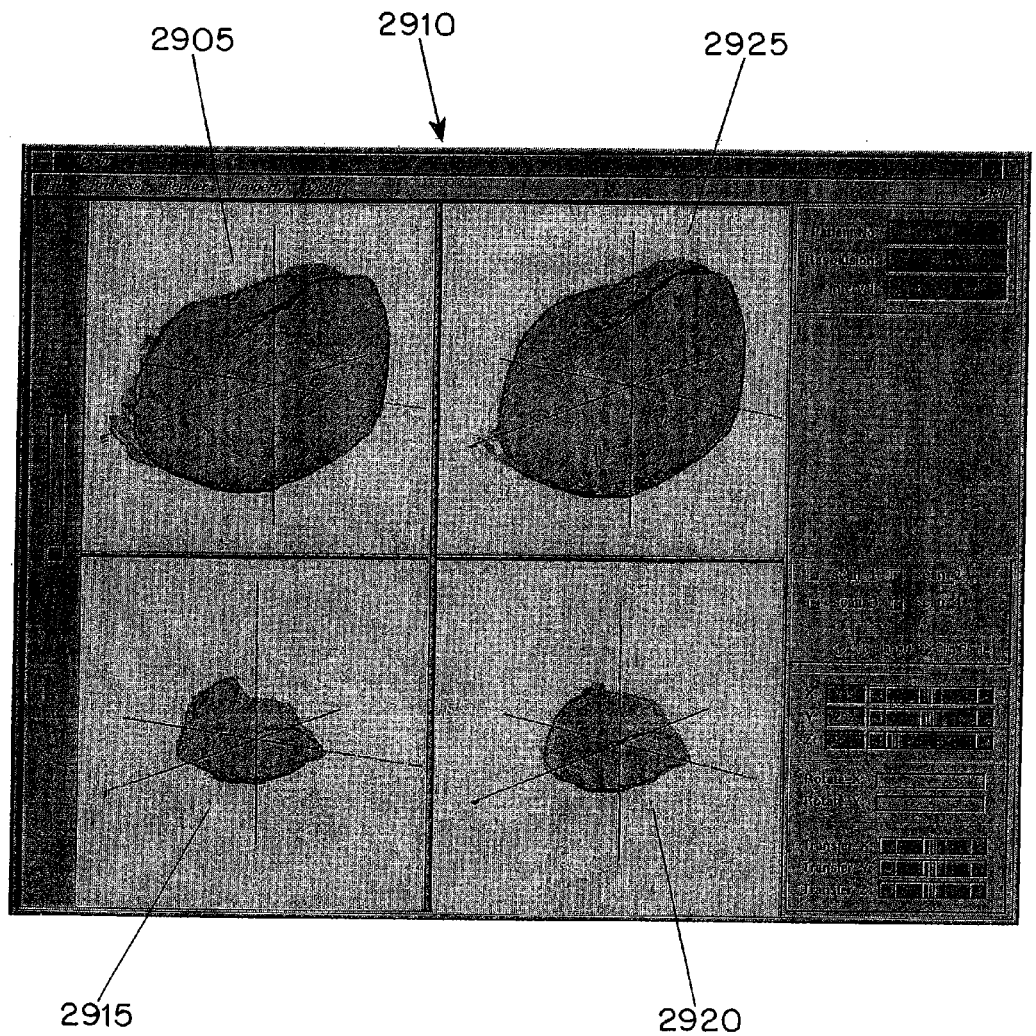
FIG. 29 is a pictorial representation of a display window suitable for presenting imaging results from the virtual cystoscopy method of FIG. 28 and providing illustrative outside views of a bladder structure.
Figure 30:
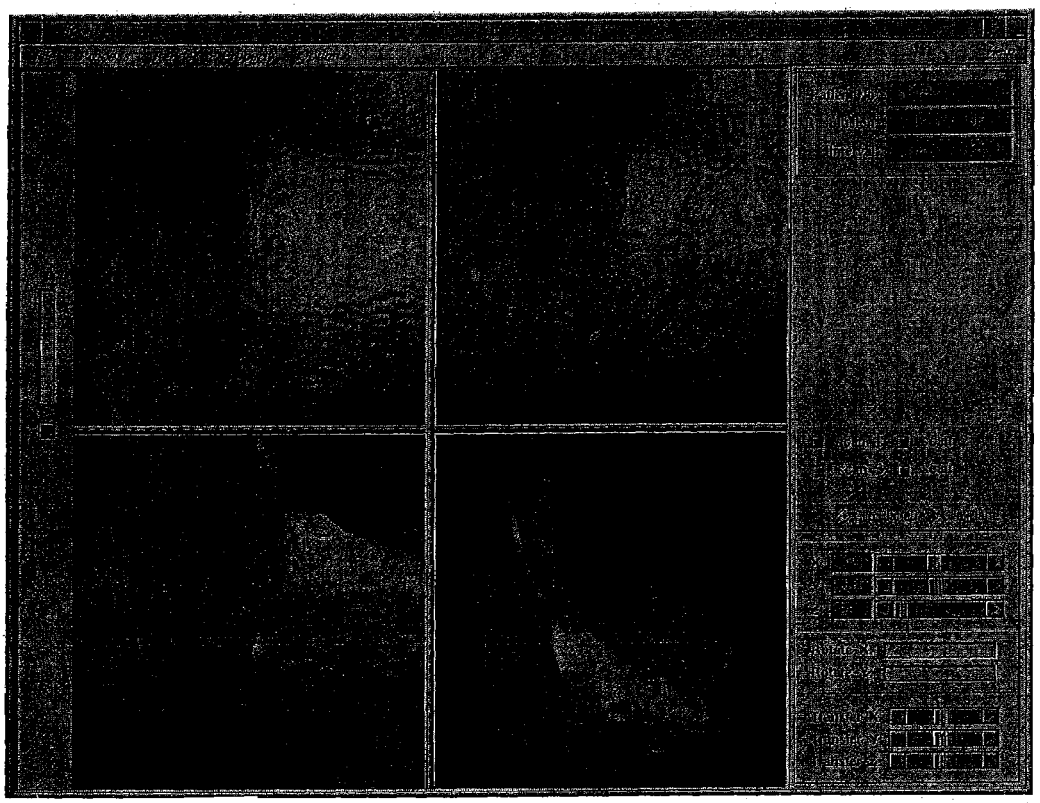
FIG. 30 is a pictorial representation of a display window suitable for presenting imaging results from the virtual cystoscopy method of FIG. 28 and providing illustrative interior views of a bladder structure.

After registration, the images from the four data sets can be viewed individually or simultaneously (step 2845). An exemplary display window is illustrated in FIGS. 29 and 30. Referring to FIG. 29, the display is partitioned into four sub windows 2905, 2910, 2915, 2920 which correspond to scan 1, scan 2, scan 3 and scan 4, respectively. A control panel section 2925 can also be provided on a portion of the display to establish a graphical user interface (GUI) to offer display and navigation functions to the user. As an operator navigates in one of the image sub windows, such as magnifying the view, the corresponding operation preferably takes place in the other sub window views as well. A user can also select one of the views for expansion to a single window display.

To reduce the amount of data which is simultaneously processed, the data sets can be partitioned, such as into 8 parts or octants (step 2840). This can be performed in a number of ways. For example, with reference to the Cartesian coordinate system illustrated in FIG. 29, the data can be portioned into the eight regions of the coordinate system: (1) X, Y, Z; (2) X, −Y, Z; (3) X, Y, −Z; (4) X, −Y, −Z; (5) −X, Y, Z; (6) −X, −Y, Z; (7) −X, Y, −Z; and (8) −X, −Y, −Z.

FIG. 29 illustrates four views of the outside of the bladder lumen taken from each of the four scans. FIG. 30 illustrates fours views of a portion of the interior of the bladder lumen also taken from each of the four scans.

Multi-Resolution Imaging and Virtual Laryngoscopy

Figure 31:
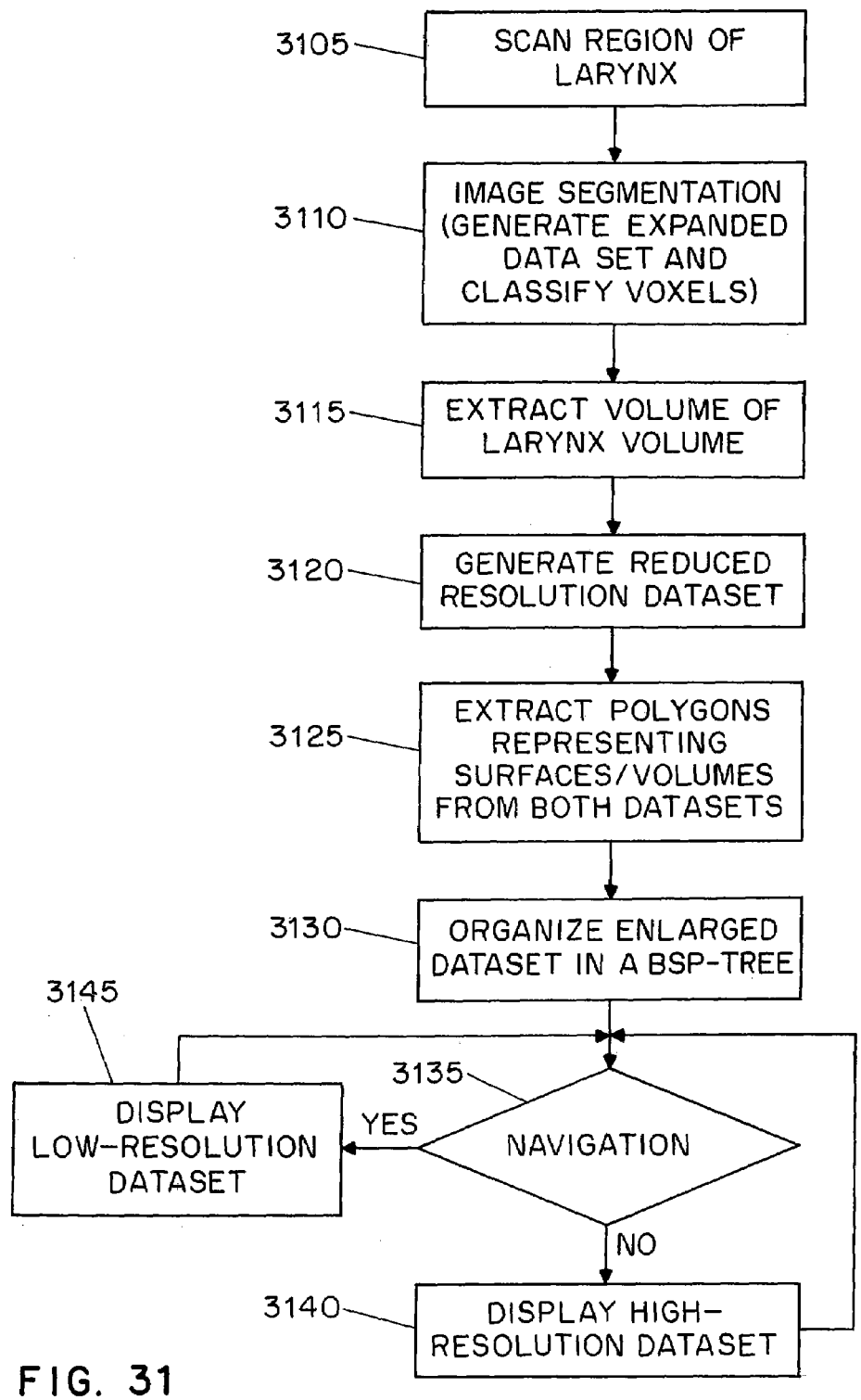
FIG. 31 is a flow chart of a method of performing virtual examination of an object, such as the larynx, using multi-resolution viewing.

The systems and methods described herein can be adapted and applied to perform multiresolution imaging which is well suited for virtual laryngoscopy. FIG. 31 is a flow chart illustrating a method for performing virtual laryngoscopy. First, an imaging scan of the region of a patient's larynx is acquired (step 3105). This can be performed using computed tomography (CT) or magnetic resonance imaging (MRI) techniques. However, because the CT scan in this region offers significantly faster acquisition time (30 seconds versus over 7 minutes for MRI) and higher resolution (0.3 mm cubic voxel compared to 1 mm cubic voxel for MRI), the CT scan is preferred. To acquire the CT scan data a GE/CTI spiral scan CT scanner can be used. A suitable scan protocol is 120 keV, 200 ma, 512×512 matrix size, 15 cm field-of-view and 3 mm/2.0:1 pitch. The scan is completed in approximately 30 seconds and results in 351 image slices of 0.3 mm thickness and results in 0.3 mm cubic voxels.

Image segmentation can be used to classify voxels into a number of categories (step 3110). In this operation, a modified self-adaptive on-line vector quantization (SOVQ) algorithm can be used. In such a case, the algorithm analyzes each voxel with respect to neighbors of up to the third order to determine local density features. Each voxel in the acquired dataset has an associated local density vector. By transforming the local density vectors using the Karhunen-Loéve (K-L) transform, feature vectors for the voxels in the volume image can be obtained. Based upon the feature vectors, the voxels can be classified and labeled. Voxel classification is dependent in part on the choice of a local voxel density vector and one preset parameter, referred to as the maximum cluster number (MCN). The MCN sets the number of voxel classifications that will be applied to the dataset. In the case of the CT images, the human eye can discern four (4) distinguishable tissue/material types. An MCN value of 5 is suitable in this case. For an MRI image, the human eye can differentiate among 6 different tissue types, and an MCN value of 7 can be used.

As part of the image segmentation process, an expanded data set is generated by interpolation between the measured data points. For example, prior to employing the SOVQ algorithm, a first order Lagrange interpolation can be applied to each slice in the dataset. This expands the 256×256 matrix size of the original slices of the data set to a 512×512 matrix size. In addition, inter-slice interpolation can be performed to further expand the dataset between actual slices. The interpolated dataset is referred to as the enlarged dataset. In addition to generating an enlarged dataset, the interpolation process also suppresses noise and reduces the partial-volume effect, as the interpolation process has a low-pass filtering effect on the data.

Using a two dimensional viewing tool, a seed voxel can be selected within the larynx lumen and a growing algorithm applied to extract the larynx volume from the dataset (step 3115). In those regions of the larynx where there may be several unconnected volume regions, multiple seed points can be selected.

With the larynx volume identified and the voxels of the regions classified through image segmentation, the next task is to manage the data in a manner which allows efficient navigation and viewing of the virtual larynx. In this case, a level-of-detail (LOD) approach is adopted and modified for use in the present method. In this LOD method, a reduced dataset is generated from the enlarged data set. For example, the 512×512×256 enlarged dataset can be reduced to a 64×64×32 reduced volume dataset using a multi-resolution decomposition with three levels of thresholding (step 3120). Next, polygons used to render the volume images in both the enlarged and reduced volume datasets can be extracted. A traditional Marching Cubes method can be used to extract polygons to fit the surface of the larynx.

One problem encountered in the prior art is managing the large number of polygons required to generate the three dimensional image for the enlarged dataset. This problem is solved in the present method by organizing the enlarged dataset in a Binary Space Partitioning (BSP) tree data structure (step 3130). The original image volume is selected as the root of the tree. The space is then partitioned into two subspaces containing an approximately equal number of polygons. This subdivision process is iteratively repeated until the number of polygons in each resulting subspace is below a threshold value. The threshold value can vary based on system performance and application requirements. The last resulting subspaces are referred to as leaf nodes of the tree. Once the subdivision process is complete, all of the voxels of the expanded dataset are stored in the leaf nodes of the BSP tree.

During navigation or viewing, polygon culling can be applied by first removing those leaf nodes that are completely outside the field-of-view from current processing operations. The remaining polygons are recalled from the BSP tree, ordered and rendered in those spaces which were not culled. Thus, the BSP tree provides an effective tool for selecting a relevant portion of the dataset for a particular navigation or display operation.

The enlarged and reduced datasets are cooperatively used in a two level LOD rendering mode. If a user is interacting with the object (step 3135), such as rotating, shifting or effecting other changes in the field of view, the polygons from the reduced dataset (64-sized) are rendered (step 3140). Because of the significantly lower number of polygons involved, interaction with the reduced dataset volume can be performed faster and with less processing overhead. The tradeoff for the increased speed is reduced image resolution. If there is no interaction from the user after a predetermined time period, the polygons of the enlarged dataset (512-sized) are selected from the BSP tree and are rendered to provide a high resolution image of the current field of view (step 3145).

Virtual Angiography

The techniques for virtual imaging and navigation can also be adapted and applied to virtual angiography. This technique can be used for detection and measurement of various abnormalities and disease of the circulatory system.

One such application of virtual angiography is the detection of abdominal aortic aneurysms, which generally start as small enlargements of the aortic vessel and exhibit a greater risk to rupture with increasing size of the aneurysm. Previously, the only effective method of treatment was open surgery, placing a graft within the aorta at the level of the aneurysm. However, this procedure has a high degree of associated morbidity and mortality. Recently developed per cutaneous placed aortic stent graft techniques have a significantly lower complication rate. Virtual angiography is an effective method to help plan these less invasive procedures and can also be an effective tool for detecting the presence of an aneurysm and tracking the growth of an aneurysm to determine if and when surgery is indicated.

Figure 32:
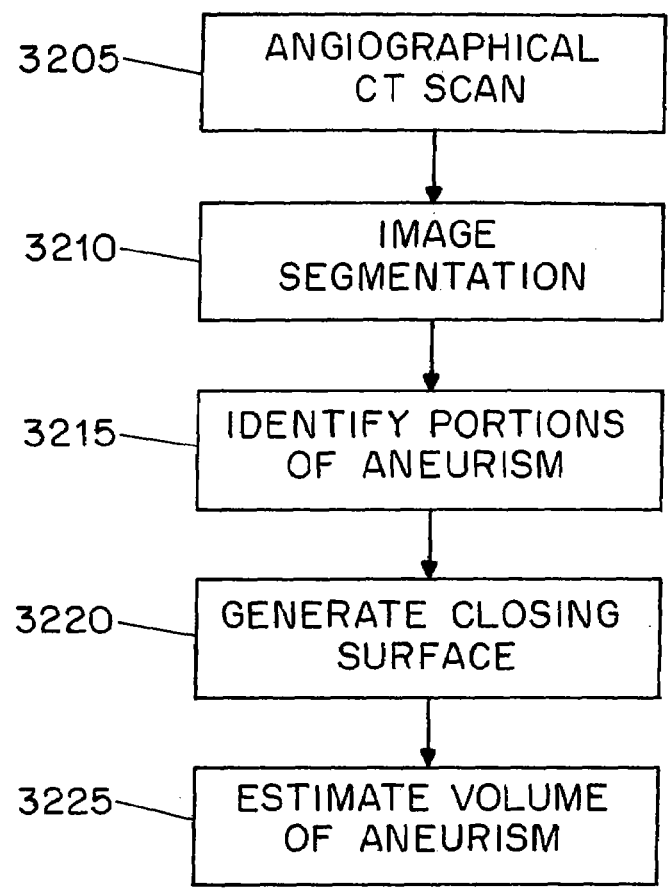
FIG. 32 is a flow chart of a method for performing virtual angiography.

FIG. 32 in a flow chart which provides an overview of the present virtual angiography method. In performing a virtual angiography, an image scan of the vessel, such as the aorta must be acquired (step 3205). Various imaging techniques can be used, such as Computed Tomography (CT), Magnetic Resonance Imaging (MRI) and ultrasound. However, an aortic CT scan is generally preferred because of the contrast between blood, soft tissue and calcium deposits which results in the CT image.

Once an image scan data set is acquired, image segmentation techniques are then applied to the data set to classify the voxels of the dataset into a number of categories (step 3210). The image segmentation techniques described above, such as in connection with FIG. 15, are generally applicable. In this case, the various feature vector values of the voxels will be grouped according to categories such as blood, soft tissue and calcium deposits. Using a blood voxel as a seed, a region growing algorithm can be used to determine the volume and extent of the aortic lumen.

In the CT image, an aneurysm has image features which closely resemble the neighboring soft tissue. As a result, the full contour of the aneurysm can be difficult to establish. However, regions with calcium deposits offer significant contrast on the CT scan and can be used to identify portions of the aneurysm, such as the endpoints of the aneurysm on the vessel wall (step 3215).

After a portion of an aneurysm is detected, one or more closing surfaces can be generated to define an estimation of the aneurysm's contour (step 3220). A convex closing surface can be established using a non-uniform, non-rational B-spline to generate a surface which runs through or near the points of the aneurysm which were identified.

After the closing surface is generated, the volume of the aneurysm can be estimated (step 3225). One method for estimating the volume is to count the number of voxels which are enclosed by the estimated closing surface. In addition, within the volume of the aneurysm, the centerline along the direction of blood flow can be determined by using a distance transform technique. Continuous local coordinate systems can then be established along this centerline and the diameter of the aneurysm determined. Virtual navigation can take place along this centerline, in a manner consistent with that described above for navigating through a lumen, such as the colon.

Referring to FIGS. 33A–C, the described method of virtual angiography can be used to assist in the generation and placement of a stent graft to bypass an abdominal aortic aneurysm. FIG. 33A illustrates a simplified diagram of an abdominal aortic aneurysm located below the renal arteries and above the bifurcation of the aorta. Because of variations from patient to patient in the specific anatomy of the aorta and the size and location of an abdominal aortic aneurysm therein, when a stent graft is to be used to bypass an aneurysm, the graft must be designed and built to specifically fit the particular aortic segment. As illustrated in FIG. 33B, this can require identifying the length of the required graft, the diameter at the points of interface on each end of the bypassed region, the angles of interface, among other variables. If the aneurysm is located near an arterial branch, the size and angles of the bifurcated ends of a bifurcated stent graft must also be determined, as illustrated in FIGS. 33B and 33C.

To date, such measurements have been performed through invasive calibrated angiograms using a catheter inserted into the aorta from an insertion made at the level of the groin region, rapid injection of a large amount of iodinated contrast and rapid radiographic imaging. This technique can be supplemented and perhaps supplanted using the present virtual angiography techniques, which can resolve such distances and angles using virtual navigation using centerlines constructed through the branches of the aortic lumen. In addition, the virtual angioscopy can be used to perform a virtual biopsy of the region where a stent graft may be inserted. This allows the operator to view beneath the arterial surface and examine the region for thrombus deposits, calcification or other factors which would contra-indicate the use of a stent graft procedure.

Another application of virtual angiography is the imaging, examination and navigation through the carotid arteries which supply blood flow to the brain. The techniques described herein with respect to virtual endoscopy are fully applicable in the case of blood vessels. For example, the vessels of interest are extracted from the acquired image data using image-segmentation techniques. Next, a navigation flight path can be established through the vessel(s). Preferably, potential fields are built up within the vessel for use in navigation. As with other organs, such as the colon, a volume-rendered model of the vessels of interest can be generated. Using the flight path and potential fields to navigate through the interior of the volume rendered blood vessel lumen, abnormalities such as vessel narrowing and plaque build up can be observed. In addition, the techniques discussed regarding virtual biopsy can be applied in this context to evaluate vessel wall and characterize build up on the wall surface, such as plaque.

Tree Branch Searching for Virtual Endoscopy

Path planning for virtual navigation through a hollow organ or object is an important task. Various techniques have been discussed, such as fly-path generation, to achieve this goal. As the geometry of the object being studied becomes more complex, such as presenting a multi-branch structure, the task of path planning becomes even more complex. It is desirable to determine not only the center line of a primary lumen, but also to identify and locate any branches extending from the primary lumen. Common examples of organs having a complex branch structure include the main airway and lungs, the cardiovascular system and, because of the presence of haustral folds, the colon. Each organ or object generally presents specific challenges for defining a path, or skeleton, for the object. However, a generalized technique for generating such a skeleton is illustrated in the flow chart of FIG. 34.

Figure 34:
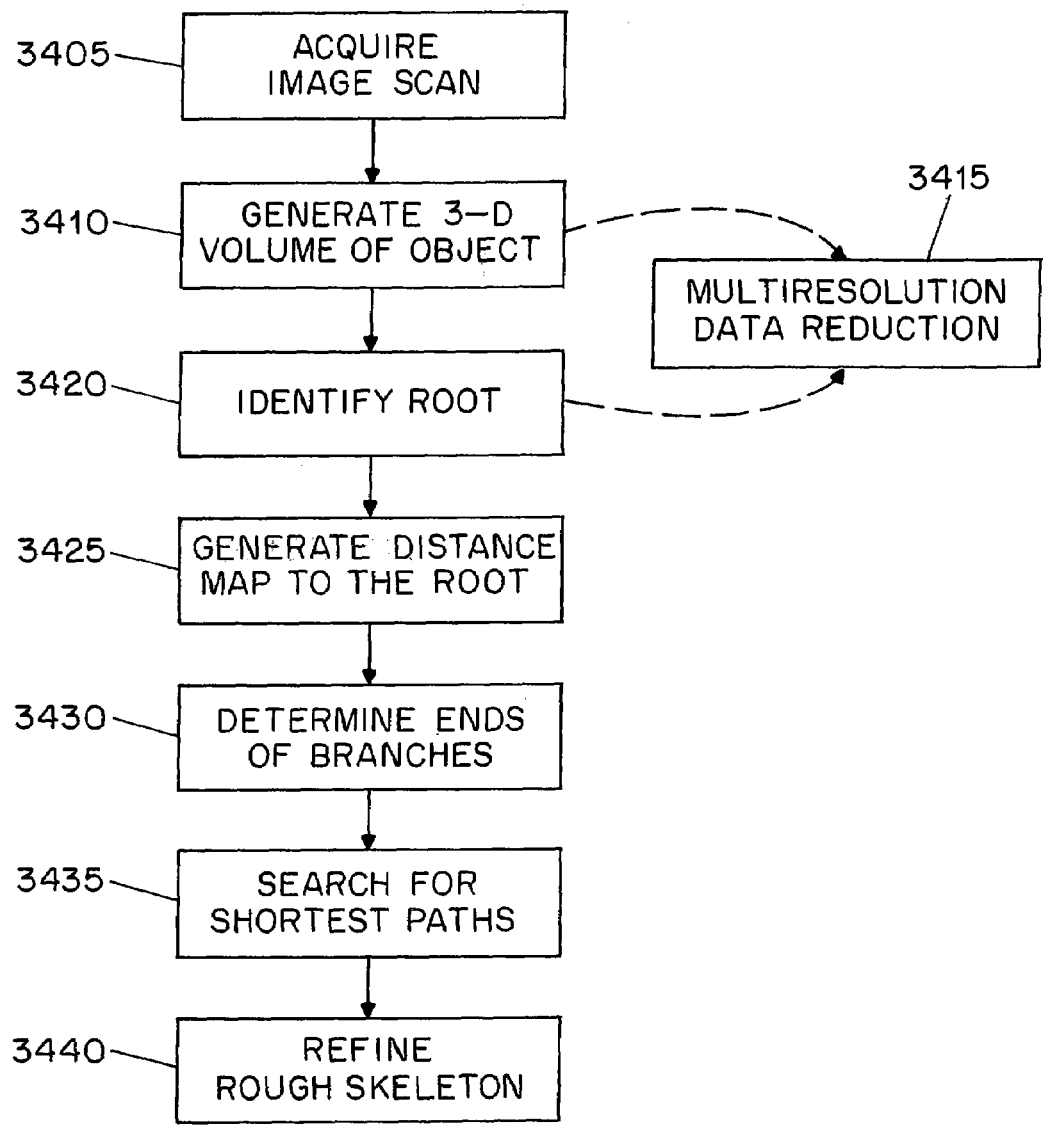
FIG. 34 is a flow chart illustrating a method for generating a skeleton structure of an object.

Referring to FIG. 34, an imaging scan of the region of interest, such as a computed tomography (CT) or Magnetic Resonance Imaging (MRI) scan, is acquired (step 3405). As discussed above, the imaging scan is transformed into a three dimensional volume of the region by stacking the binary images of the imaging scan and defining three dimensional volume units, or voxels, from these stacked images (step 3410). Depending on the volume and complexity of the region of interest, it may be desirable to reduce to size of the dataset of the three dimensional volume prior to generating the skeleton. To this end, a multiresolution data reduction process, which is discussed in more detail below, can be used (step 3415).

The skeleton is a subset of the three dimensional volume. Preferably, the skeleton has the following attributes: 1) It preserves the homotopy of the tree; 2) it is 26-connected; 3) it is one voxel thick; 4) it approximates the central axes of the branches; and 5) it is relatively smooth. The degree of homotopy is somewhat application specific. For example, in generating a skeleton of the colon lumen, the skeleton will generally be a single path from end to end, despite the presence of numerous haustral folds which can be several voxels deep. However, in the cardiovascular system and pulmonary system, a small offshoot from the root which is several voxels deep can represent a legitimate branch in the system.

Returning to FIG. 34, in the volume of interest, a root voxel is identified in the volume (step 3420). In performing virtual endoscopy, this can be performed manually based on an understanding of the geometry of the structure being evaluated.

Figure 35:
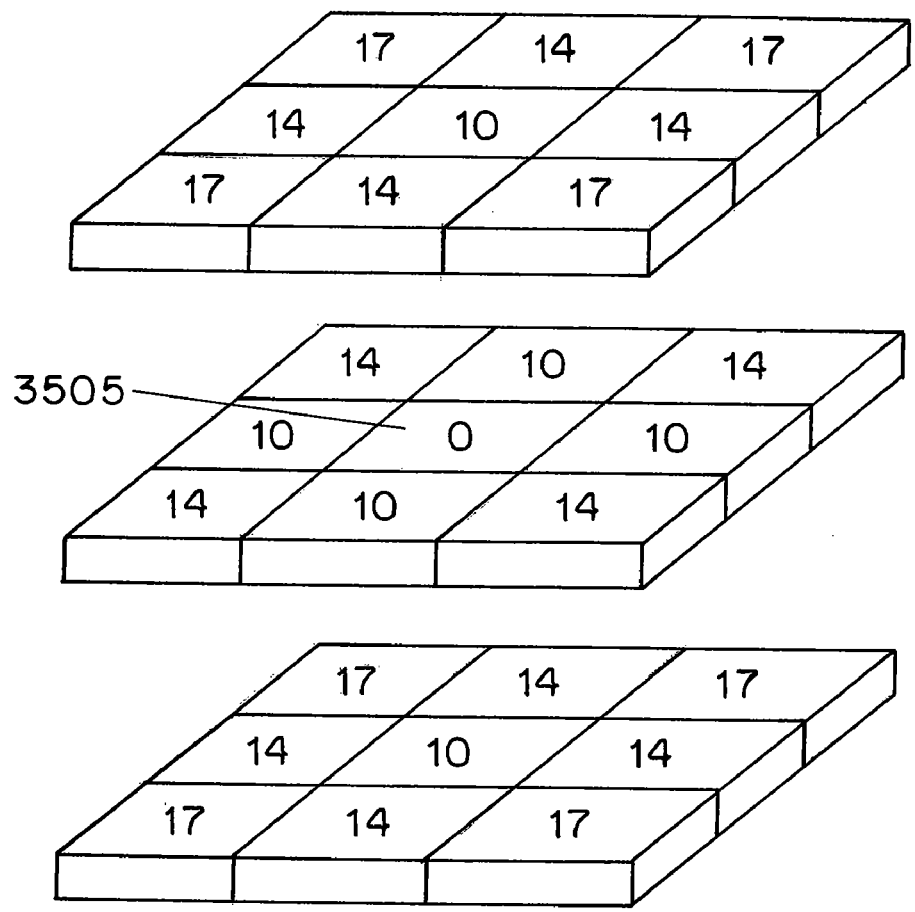
FIG. 35 is a schematic diagram of a 26-connected, Euclidean weighted, cubic distance plate.

A distance map can then be generated to identify the branches in the tree and the distances between the endpoints of the branches and the root voxel (step 3425). A presumption applied in this method is that there exists one unique endpoint on each branch which exhibits the longest distance to the root of the tree. FIG. 35 is a schematic diagram illustrating a 3×3×3 cubic voxel arrangement which is referred to as a 26-connected voxel cubic distance plate. In the center of this arrangement is a seed voxel 3505, which is assigned a distance weight of zero. Around the seed voxel 3505 are 26 connected neighbor voxels which are assigned distance weights based on the respective Euclidean distance between the respective neighbor voxel and the seed. In a cubic arrangement the Euclidian distance can assume a normalized value of 1, $\sqrt{2}$, $\sqrt{3}$ which is approximately equal to 1, 1.4 and 1.7. To simplify processing, the voxels can be assigned integer value weights of 10, 14, and 17 to approximate the relative Euclidian distances.

FIG. 36 is a pseudo-code representation of an algorithm for determining the distance map from a voxel in the volume to the root using the Euclidian weighted distances of the 26-connected cubic distance plate of FIG. 35. From the generated distance map, branches are identified and the endpoints of the branches are determined (step 3430).

Referring to FIG. 36, the root of the volume is labeled with the integer value 0. A processing queue is then formed with the voxels in the volume. The voxels are then labeled in a first-in, first out manner by adding the Euclidian distances between the voxel at the top of the queue and the root voxel. This process is repeated until all of the voxels in the volume are assigned a value in the distance map.

Because the labeling of voxels in the distance map will depend, in part, on the queuing order, the resulting distance map does not provide a unique solution. However, regardless of the queuing order, there is always at least one farthest point for each branch. In addition, for each voxel, other than the root voxel, there is always at least one 26-connected neighbor in the volume which has a shorter distance to the root. Thus, the endpoints of the branches are readily detectable by searching the distance map for local maximum distances (local maxima) (step 3430). The term local maxima is a relative term. In evaluating the volume for local maxima, the volume should be partitioned into various subspaces which are appropriate to the object being evaluated. The expected feature size, branch length, branch diameter, etc. are generally considered in determining the subspace partitions.

Once the endpoints of the branches are determined, the shortest path from the endpoint to the root voxel is determined (step 3435). The shortest paths from the endpoints to the root define the basic structure of the branches of the tree and approximate the centerline of the branches. This is referred to as the rough skeleton of the volume. The shortest paths are preferably generated from the branches at farthest end of the tree and begin from the end of those branches. From the most remote branch endpoint, the first voxel is selected and its 26-connected neighbors are analyzed to determine which voxel is in the minimal distance path from endpoint to root. This process is repeated until a selected voxel meets the root. This results in a one-voxel wide path from the farthest end to the root. Searching for the shortest path for other branches is similar. However, for subsequent branches, the selection process can terminate when the current path reaches a previously assigned path (e.g., the path need not lead all the way to the root). The collection of all of the interconnected shortest paths is the resulting rough skeleton of the object.

Depending on the application of the resulting rough skeleton, it may be desirable to refine the rough skeleton (step 3440). One step of refining the skeleton is to centralize the skeleton within the branches. Centralization preferably takes place branch by branch from the longest branch to the shortest. Starting with the longest branch, a uniform interval is selected, generally in the range of 4–8 voxels, along the branch. For each interval, the tangent direction of the voxel on the rough skeleton is calculated and a plane crossing the voxel perpendicular to the tangent direction is determined. A two dimensional area defined by the intersection of the plane and the volume is created and the center of this intersection can be computed using the known maximum disk technique. The centers of intersection can then be connected using a bi-cubic, B-spline interpolation or other curve fitting method. For the remaining branches, the endpoint which meets another branch or the root must first be adjusted to match the position of the previously centered skeleton branch. Then, centralization can proceed in the same manner as described for the longest branch.

Referring back to step 3415, when a large dataset is involved, it may be required, or at least desirable, to reduce the size of the dataset to speed up processing and reduce processing cost. Noting that the tree structure can be preserved within a range of scales, the large volume can be shrunk to a smaller scale space for structure analysis.

A shrinking method based on multiresolution analysis theory can be used. The input data is the stack of binary images of the same size which can be obtained from the segmentation results of the CT or MRI scan. The x-direction is taken along the slice image width, the y-direction is along the slice image height, and the z-direction is along the direction of slice by slice. The foreground voxels in the tree volume are set to value of 128 (maximum) and the background voxels are set to value 0 (minimum). A Daubechies' bi-orthogonal wavelet transform with all rational coefficients is employed. This one-dimensional (1D) discrete wavelet transformation (DWT) is first applied along to the x-direction row by row. From application of the DWT only the lower frequency components are retained and packed. The computation is preferably implemented in floating points. Noting that the DWT is applied to the binary signal, there are two kinds of nonzero coefficients which result in the lower frequency component. The first is of value 128 and this kind of coefficients are located in the interior of the volume. The second is of a value not equal to 128 and these coefficients locate the boundary of the volume.

The coefficients of the second kind are compared against a predetermined threshold value. If its absolute value is larger than a pre-set threshold Ti, the value of the coefficient is set to 128; otherwise, it is set to 0. This results in a stack of binary images with a row size of half of the original dataset. The same DWT is then applied to the resulting dataset along the y-direction column by column, where the similar thresholding is employed to the lower frequency components. The result is again a stack of binary images, but now with both half row and column size as compared to the original dataset. Finally, the DWT is applied to the last result along the z-direction and the lower frequency components are retained. This step completes the first level decomposition.

The resulting dataset of the first level decomposition is of half size in all three directions as compared to the original dataset. If the shrinking procedure stops at this level, the finial thresholding is applied. It revalues those coefficients of nonzero and non-128 value. If the absolute value of this kind of coefficient is larger than a pre-set threshold T2, it will be revalued as 128; otherwise, it is revalued as 0. If further shrinking is needed, the same thresholding algorithm is applied with the threshold T1. Further shrinking proceeds as previously described, but is applied to the dataset shrunk at the last previous level. The decomposition procedure can be recursively applied until the resulting volume meets the desired reduced data volume. In virtual endoscopy, the slice images are of 512×512 pixel size. The maximum decomposition level is usually three, resulting in a 64×64 reduced pixel size.

The volume is isotropically shrank in all directions with the presented method. The two pre-set thresholds, T1 and T2, are used to control the degree of shrinking. If the volume is significantly over shrunk, connectivity may be lost in the reduced volume. If it is over shrunk to a leaser degree, two separate branches may merge into one branch in the reduced volume dataset. The larger the two threshold values, the thinner the reduced volume is. The range of those two thresholds is [0, r×128], where 0<r<1. Preferably, the range for virtual endoscopy is r∈ (0.08, 0.28) for T1 and r∈ (0.7, 0.98) for T2. The exact determination is dependant on the feature size of the particular application and is selected to achieve reduction while retaining the fidelity of the structure information in the shrunk volume.

After shrinking the original volume, the tree branch searching procedure can be applied to the smaller volume (steps 3420–3440). The resultant skeleton can be mapped back into the original scale space. When scaled to the original space, the image of the smaller scale skeleton no longer remain a connected path in the original scale space. These voxels in the image act as control points for the final skeleton. The control points are centralized using the algorithm as described previously, and then, they are interpolated to form the final skeleton of the object.

Computer Assisted Diagnosis

The virtual examination techniques described herein lend themselves to applications for the computer assisted diagnosis (CAD) of various conditions. For example, as described above, by examining the geometry of an organs tissue for local Gausian curvatures, regions with abnormal geometry, such as polyps inside a colon lumen, can automatically be identified. This technique can be generalized and used in conjunction with texture features to provide CAD functionality for a number of applications.

For example, using the multi-scan imaging of the bladder described above, automated detection or tumors in the bladder wall can be performed. In this case, the degree of tumor invasion within the bladder wall is generally used to define the stage of bladder cancer. Using the multi-scan imaging and image segmentation techniques described above, the region of the bladder wall can be readily delineated. Regions of normal bladder tissue generally exhibit a substantially uniform texture feature. However, if a tumor is present in the region, the uniform texture feature will be interrupted. Thus, using texture analysis to evaluate the wall of the bladder, a region which may exhibit a tumor will present itself as a disturbance, or "noisy region" within the uniform texture.

The texture of a region can be represented by a probability distribution function (PDF) which characterizes the intensity correlation between voxels within a defined range. A two-dimensional PDF can be used to represent a texture feature. Such a PDF characterizes the correlation between two closest voxels along all directions. To estimate the PDF, the intensities of any two closest neighbor voxels in a region of interest can be recorded as a sample vector for the region of interest (e.g., context). Using a number of such sample vectors, a cumulating distribution function (CDF) can be generated which estimates the PDF for that context. For each voxel, sample vectors within a range of its neighbor can also be used to generate a local CDF.

A statistical test, such as a Kolmogorov-Smirnov test, can be applied to the CDF to determine whether the CDF of the context and the local CDF are statistically equivalent, e.g., within a predefined confidence level. If so, the local texture feature around the current voxel is regarded as identical to the context. Otherwise, the current voxel exhibits a different texture feature from that of the context and may be regarded as a potential abnormality, such as a tumor. The level of confidence used to determine whether a voxel is statistically equivalent to the context can be varied to increase or decrease the sensitivity of detection.

In an alternative method of applying the PDF or CDF for texture analyis, each CDF or PDF can be regarded as a point in a functional linear space. The distance between two CDF's or PDF's in that space can be measured, such as in terms of the Skorohold metric. This distance provides a measure of the degree of similarity of PDF's. For example, the distance between a local CDF and the context CDF can be calculated and the resulting distance can be compared to one or more distancing thresholds. If the distance is large, the local texture may be considered different from the context, which can indicate that such a voxel belongs to a region with a potential abnormality or tumor. Preferably, the distancing thresholds are determined based on evaluation of a statistically sufficient known data sets.

The distance calculated above can be used with visualization techniques and volume rendering techniques, such as those described herein. For example, a feature volume dataset having a size comparable to the original dataset can be created. The intensity for each voxel in the new dataset can then be assigned based upon the distance between the local CDF and the CDF of the context. When this three dimensional volume dataset is viewed through volume rendering techniques, the regions which contain suspected tumors will exhibit a higher image intensity than the surrounding area.

As was discussed above in connection with automatic detection of polyps, the surface of a lumen can be represented as a continuously second differentiable surface in three dimensional Euclidean space, such as by using a C-2 smoothness surface model. In such a model, each voxel on the surface of the colon has an associated geometrical feature which has a Gauss curvature, referred to as Gauss curvature fields. For various organs, certain expected local features can be characterized by distinct curvature templates. For example, in the context of the colon, the expected local features include smooth curve surfaces, ring folds, convex hills from a smooth surface and plateaus from a smooth surface. These last two local features may be indicative of a polyp or tumor. Accordingly, by searching the Gauss curvature fields for specific predetermined local feature templates, polyps, tumors and other abnormalities of interest can be automatically detected. This use of surface geometry to perform computer assisted diagnosis can be used alone, or in conjunction with the texture-based CAD techniques described above.

As an alternative to rendering and viewing the entire organ or region of interest, the surface under observation can be partitioned into small areas, or patches, which are defined by the local curvature templates. Each patch should contain voxels which have a common geometry feature, or curvature template. A single viewing point is then determined for the patch which allows all voxels of the patch to be observed. The patches are then assigned a priority score indicating the probability that the patch represents a polyp or other abnormality. The patches can then be observed individually, in priority order, rather than requiring the operator to navigate the entire organ volume to search out suspect areas. Of course, a preferred diagnostic system includes the ability to toggle between views such that an operator can readily change from viewing a patch to viewing the patch in the context of the organ. Alternatively, these two views can be presented simultaneously. Again, the texture based approaches can be used to supplement this approach. By mapping the results of texture analysis onto the patches being observed, the texture information can also be observed and used in diagnoses.

The foregoing merely illustrates the principles of the present imaging and examination systems and methods. It will thus be appreciated that those skilled in the art will be able to devise numerous systems, apparatus and methods which, although not explicitly shown or described herein, embody the principles of the invention and are thus within the spirit and scope of the invention as defined by its claims.

For example, the methods and systems described herein could be applied to virtually examine an animal, fish or inanimate object. Besides the stated uses in the medical field, applications of the technique could be used to detect the contents of sealed objects which cannot be opened. The techniques can also be used inside an architectural structure such as a building or cavern and enable the operator to navigate through the structure.

What is claimed is:

1. A method of performing computed assisted diagnosis of a region of interest, comprising:
   acquiring imaging scan data including at least a portion of the region of interest;
   converting the imaging scan data to a volume representation including a plurality of voxels, at least a portion of the voxels representing a surface of the region of interest;
   analyzing a first portion of voxels representing the surface to determine a context surface texture feature of the region of interest;
   analyzing a second portion of voxels representing the surface to identify a local surface texture feature;
   comparing the local surface texture feature to the context surface texture feature and identifying the local surface texture as indicative of an abnormality if the local surface texture is at least sufficiently different from the context texture feature.

2. The method of performing computed assisted diagnosis according to claim 1, wherein the local surface texture feature is included in a probability density function characterizing a correlation between two voxels of the second portion of voxels.

3. The method of performing computed assisted diagnosis according to claim 2, wherein the two voxels are adjacent voxels.

4. The method of performing computer assisted diagnosis according to claim 2, wherein intensity values of said second portion of voxels are used to generate an estimate of the probability density function.

5. The method of performing computer assisted diagnosis according to claim 4, wherein a plurality of voxel intensity values are used to generate a cumulating distribution function of the region of interest and a local cumulating distribution function, and wherein the local cumulating distribution function is compared against the context cumulating distribution function to identify regions of abnormality.

6. The method of performing computer assisted diagnosis according to claim 5, wherein a distance is determined between said local cumulating distribution function and said context cumulating distribution function, the distance providing a measure of abnormality.

7. The method of performing computer assisted diagnosis according to claim 6, wherein the distance is used to assign intensity values to the voxels representing a surface of the region of interest and wherein said method further comprises displaying said voxels such that variations in intensity represent regions of abnormality.

8. The method of performing computer assisted diagnosis according to claim 7, wherein the region of interest includes the colon and wherein the abnormality includes polyps.

9. The method of performing computer assisted diagnosis according to claim 1, wherein the region of interest includes the aorta and wherein the abnormality includes abdominal aortic aneurysms.

10. A method of performing computed assisted diagnosis of a region of interest, comprising:
acquiring imaging scan data including at least a portion of the region of interest;
converting the imaging scan data to a volume representation including a plurality of voxels, at least a portion of the voxels representing a surface of the region of interest;
analyzing a first portion of voxels representing the surface to determine a context surface texture feature of the region of interest;
analyzing a second portion of voxels representing the surface to identify a local surface texture feature;
comparing the local surface texture feature to the context surface texture feature and identifying regions as indicative of an abnormality if the local surface texture of the region is at least sufficiently different from the context surface texture feature; and
analyzing said identified regions where the local surface texture is indicative of an abnormality for a geometric feature further indicative of an abnormality.

11. The method of performing computed assisted diagnosis according to claim 10, wherein the local surface texture feature is included in a probability density function characterizing a correlation between two voxels of the second portion of voxels.

12. The method of performing computed assisted diagnosis according to claim 11, wherein the two voxels are adjacent voxels.

13. The method of performing computer assisted diagnosis according to claim 12, wherein intensities of said second portion of voxels are used to generate an estimate of the probability density function.

14. The method of performing computer assisted diagnosis according to claim 13, wherein a plurality of voxel intensities are used to generate a cumulating distribution function of the region of interest and a local cumulating distribution function, and wherein the local cumulating distribution function is compared against the context cumulating distribution function to identify regions of abnormality.

15. The method of performing computer assisted diagnosis according to claim 14, wherein a distance is determined between said local cumulating distribution function and said context cumulating distribution function, the distance providing a measure of abnormality.

16. The method of performing computer assisted diagnosis according to claim 15, wherein the distance is used to assign intensity values to the voxels representing a surface of the region of interest and wherein said method further comprises displaying said voxels such that variations in intensity represent regions of abnormality.

17. The method of performing computer assisted diagnosis according to claim 16, wherein the region of interest includes the colon and wherein the abnormality includes polyps.

18. The method of performing computer assisted diagnosis according to claim 10, wherein the region of interest includes the aorta and wherein the abnormality includes abdominal aortic aneurysms.

19. The method of performing computer assisted diagnosis according to claim 10, wherein the surface is represented as a second differentiable surface where each surface volume unit has an associate Gauss curvature and wherein said Gauss curvatures combine to form said geometric features.

20. The method of performing computer assisted diagnosis according to claim 10, wherein a plurality of predetermined geometrical feature templates are defined and wherein the geometric features of said surface are compared to said templates to determine a geometric feature classification.

* * * * *